United States Patent
Tachibana

(10) Patent No.: US 10,857,104 B2
(45) Date of Patent: Dec. 8, 2020

(54) METHOD FOR MANUFACTURING BUBBLES AND BUBBLES

(71) Applicant: SonoCore, Inc., Tokyo (JP)

(72) Inventor: Katsuro Tachibana, Fukuoka (JP)

(73) Assignee: SONOCORE, INC., Tokyo (JP)

( * ) Notice: Subject to any disclaimer, the term of this patent is extended or adjusted under 35 U.S.C. 154(b) by 238 days.

(21) Appl. No.: 15/565,118

(22) PCT Filed: Apr. 7, 2016

(86) PCT No.: PCT/JP2016/061350
§ 371 (c)(1),
(2) Date: Oct. 6, 2017

(87) PCT Pub. No.: WO2016/163439
PCT Pub. Date: Oct. 13, 2016

(65) Prior Publication Data
US 2018/0116971 A1 May 3, 2018

(30) Foreign Application Priority Data

Apr. 8, 2015 (JP) .................................. 2015-079625

(51) Int. Cl.
*B01F 3/04* (2006.01)
*A61K 9/50* (2006.01)
(Continued)

(52) U.S. Cl.
CPC .............. *A61K 9/5089* (2013.01); *A61B 8/06* (2013.01); *A61J 1/14* (2013.01); *A61K 9/5052* (2013.01);
(Continued)

(58) Field of Classification Search
CPC . A61B 8/06; A61J 1/14; A61K 9/5089; A61K 9/5052; A61K 9/10; A61K 9/127;
(Continued)

(56) References Cited

U.S. PATENT DOCUMENTS

| 4,793,714 A | * | 12/1988 | Gruber | ................ B01F 3/04978 261/122.1 |
| 5,585,044 A | * | 12/1996 | Kawakami | .......... B01F 3/04978 261/1 |

(Continued)

FOREIGN PATENT DOCUMENTS

| EP | 0840570 B1 | 8/2003 |
| JP | H10505900 A | 6/1998 |

(Continued)

OTHER PUBLICATIONS

International Bureau of WIPO, International Preliminary Report on Patentability Issued in Application No. PCT/JP2016/061350, dated Oct. 19, 2017, WIPO, 9 pages.

(Continued)

*Primary Examiner* — Charles S Bushey
(74) *Attorney, Agent, or Firm* — McCoy Russell LLP

(57) ABSTRACT

A method for manufacturing bubbles of the present invention includes: injecting an aqueous liquid 10 into a container 20 to a predetermined height; and vibrating the container at the number of revolution of equal to or high than 5,000 rpm such that the aqueous liquid 10 repeatedly collides with an inner surface of the container 20. According to the manufacturing, simply by vibrating the container 20 at a predetermined number of revolution, a large amount of bubbles 1 having a uniform size can be stably generated in the aqueous liquid 10. Furthermore, the vibrating the container 20 is preferably performed in a state where an internal pressure of the container 20 is higher than 1.0 atm.

10 Claims, 27 Drawing Sheets

(51) Int. Cl.

| | |
|---|---|
| *A61B 8/06* | (2006.01) |
| *A61K 49/00* | (2006.01) |
| *B01F 11/00* | (2006.01) |
| *A61J 1/14* | (2006.01) |
| *B65B 3/00* | (2006.01) |
| *B65D 51/00* | (2006.01) |
| *A61K 49/22* | (2006.01) |
| *A61N 7/00* | (2006.01) |
| *A61K 47/02* | (2006.01) |
| *A61K 47/12* | (2006.01) |
| *A61K 47/24* | (2006.01) |
| *A61K 47/26* | (2006.01) |
| *A61K 47/42* | (2017.01) |
| *A61K 9/127* | (2006.01) |
| *A61K 9/10* | (2006.01) |
| *A61K 47/28* | (2006.01) |

(52) U.S. Cl.
CPC .......... *A61K 49/00* (2013.01); *A61K 49/0047* (2013.01); *A61K 49/223* (2013.01); *A61N 7/00* (2013.01); *B01F 3/04* (2013.01); *B01F 11/00* (2013.01); *B65B 3/003* (2013.01); *B65D 51/002* (2013.01); *A61K 9/10* (2013.01); *A61K 9/127* (2013.01); *A61K 47/02* (2013.01); *A61K 47/12* (2013.01); *A61K 47/24* (2013.01); *A61K 47/26* (2013.01); *A61K 47/28* (2013.01); *A61K 47/42* (2013.01); *A61N 2007/0039* (2013.01)

(58) Field of Classification Search
CPC ........ A61K 47/02; A61K 47/12; A61K 47/24; A61K 47/26; A61K 47/28; A61K 47/42; A61K 49/00; A61K 49/0047; A61K 49/223; A61N 7/00; A61N 2007/0039; B01F 3/04; B01F 11/00; B65B 3/003; B65D 51/002
USPC ..................................................... 261/81, 83
See application file for complete search history.

(56) References Cited

U.S. PATENT DOCUMENTS

| | | | | |
|---|---|---|---|---|
| 5,656,211 | A * | 8/1997 | Unger | .................. A61K 9/127 264/4.1 |
| 6,039,309 | A * | 3/2000 | Kuklinski | ........... B01F 3/04241 261/1 |
| 8,205,862 | B2 * | 6/2012 | Goltenboth | ......... B01F 3/04815 261/81 |
| 2011/0044903 | A1 | 2/2011 | Borrelli | |
| 2012/0270177 | A1 | 10/2012 | Nakashima et al. | |
| 2013/0022550 | A1 | 1/2013 | Unger et al. | |
| 2018/0085477 | A1 * | 3/2018 | Tachibana | ................ A61B 8/06 |
| 2018/0104146 | A1 * | 4/2018 | Tachibana | ................ A61B 8/06 |

FOREIGN PATENT DOCUMENTS

| | | | |
|---|---|---|---|
| JP | H11507873 | A | 7/1999 |
| JP | 2002209896 | A | 7/2002 |
| JP | 2005154282 | A | 6/2005 |
| JP | 2005246294 | A | 9/2005 |
| JP | 2008509890 | A | 4/2008 |
| JP | 2014217828 | A | 11/2014 |
| WO | 9740858 | A1 | 11/1997 |

OTHER PUBLICATIONS

ISA Japan Patent Office, International Search Report Issued in Application No. PCT/JP2016/061350, dated Jun. 21, 2016, WIPO, 5 pages.

"Precellys Lysing Kits," Bertin Instruments Website, Available Online at https://www.bertin-instruments.com/wp-content/uploads/secured-file/Precellys-lysing-kits_4P_HD_print.pdf+&cd=2&hl=en&ct=clnk&gl=us, Available as Early as Feb. 2012, 3 pages.

ISA Japan Patent Office, International Search Report Issued in Application No. PCT/JP2016/061294 dated Jun. 21, 2016, WIPO, 5 pages.

Tsuchiya, K., "Application of Nanobubbles to Ultrasound Imaging," Journal of the Japanese Society of Colour Material, vol. 83, No. 2, Available as Early as Jan. 2010, 19 pages.

* cited by examiner

FIG. 2
(a) 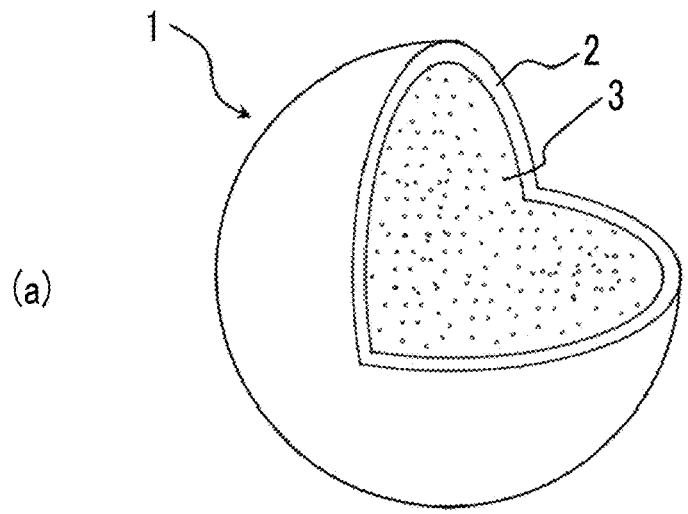
(b) 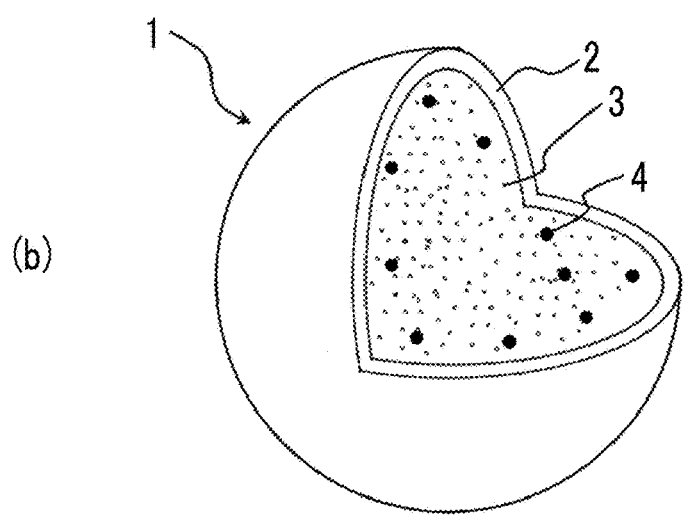
(c) 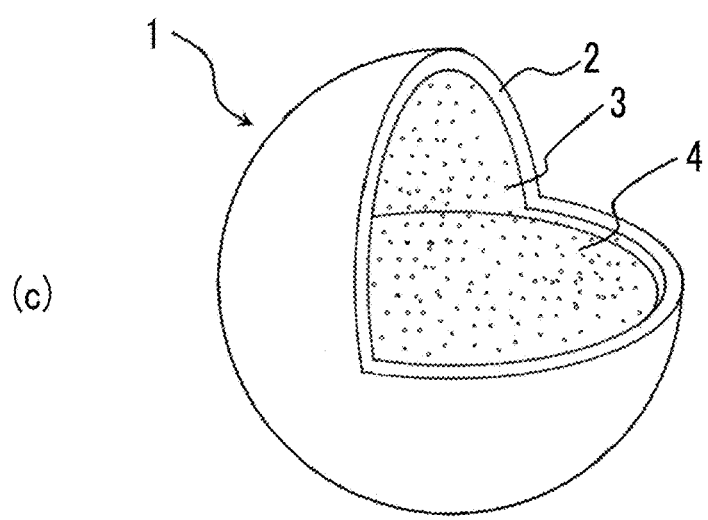

FIG. 18
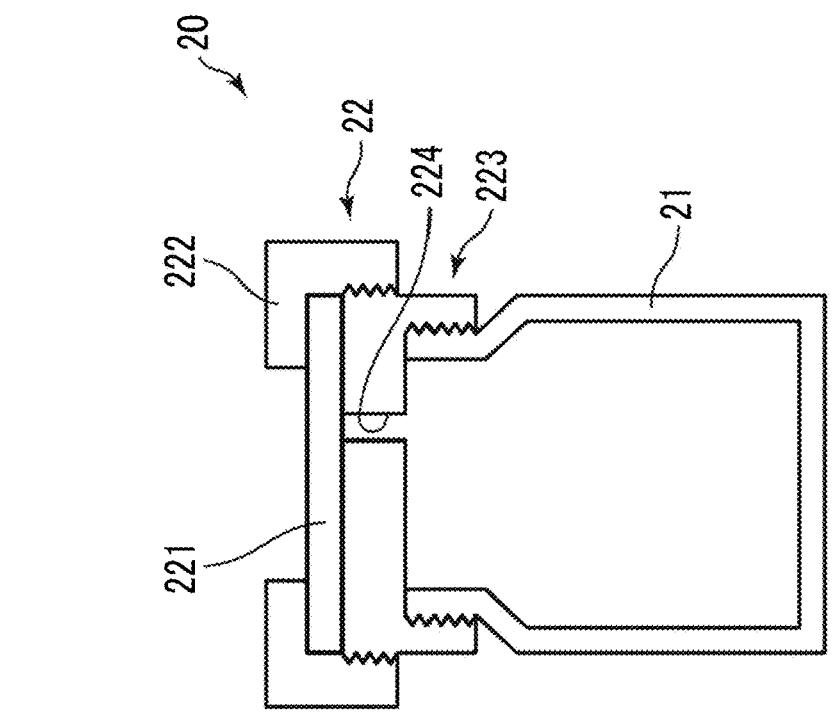
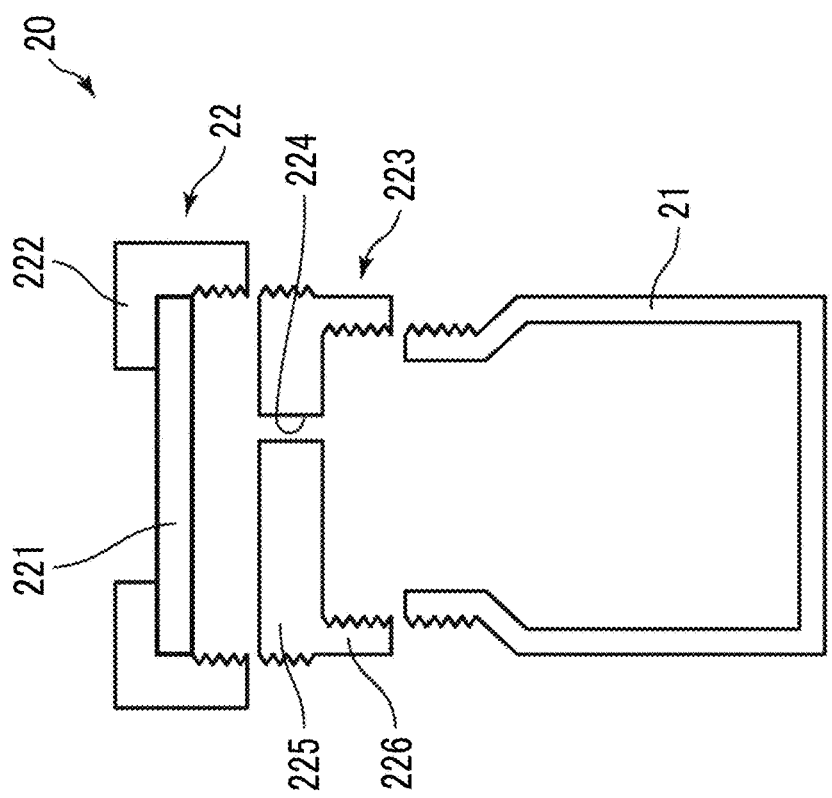

FIG. 23
0.6W/cm² 60sec
(a)
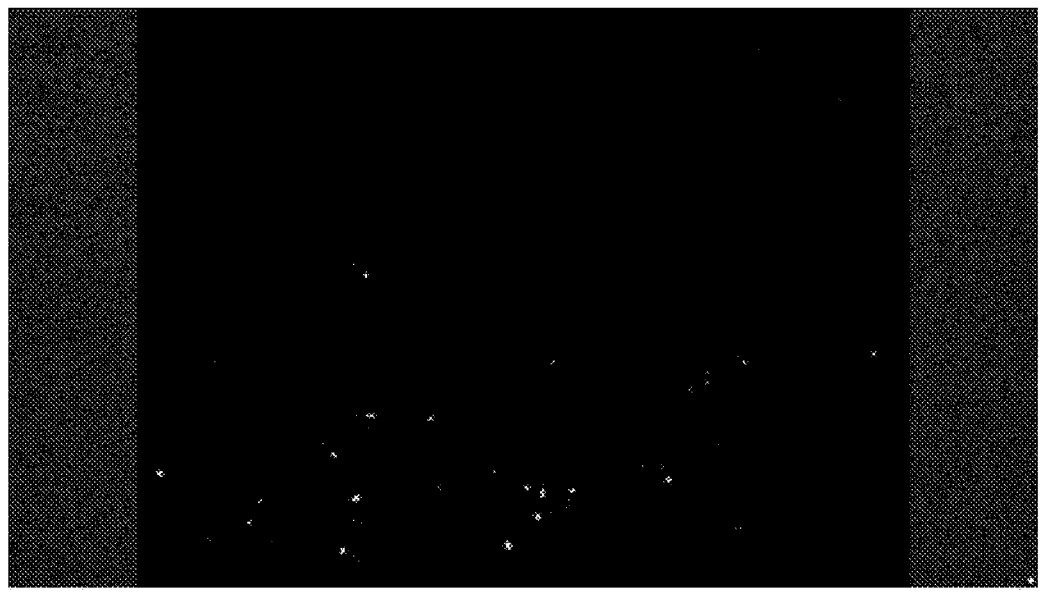
0.8W/cm² 60sec
(b)
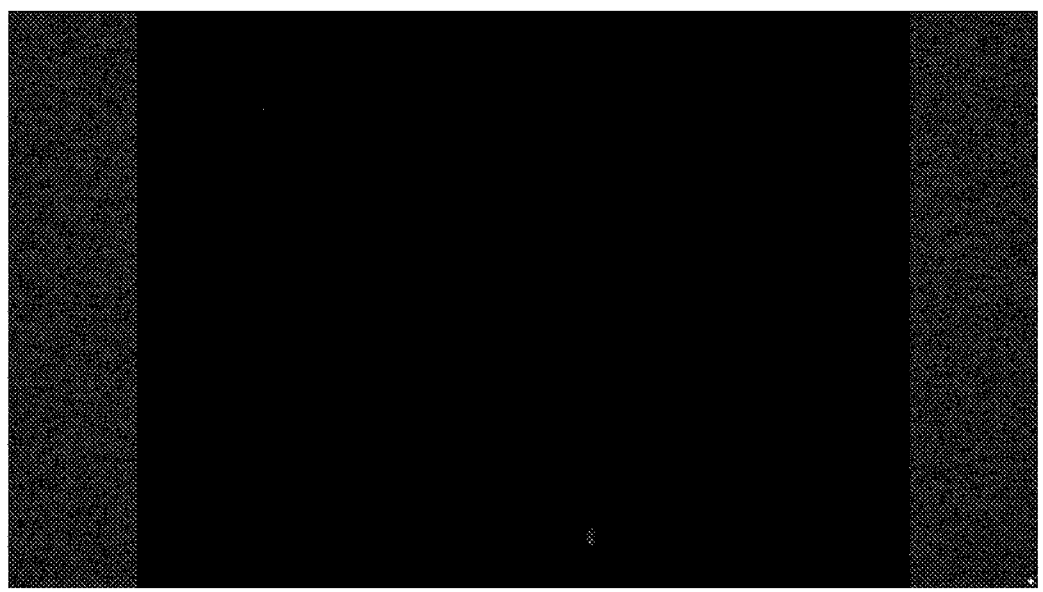

FIG. 24
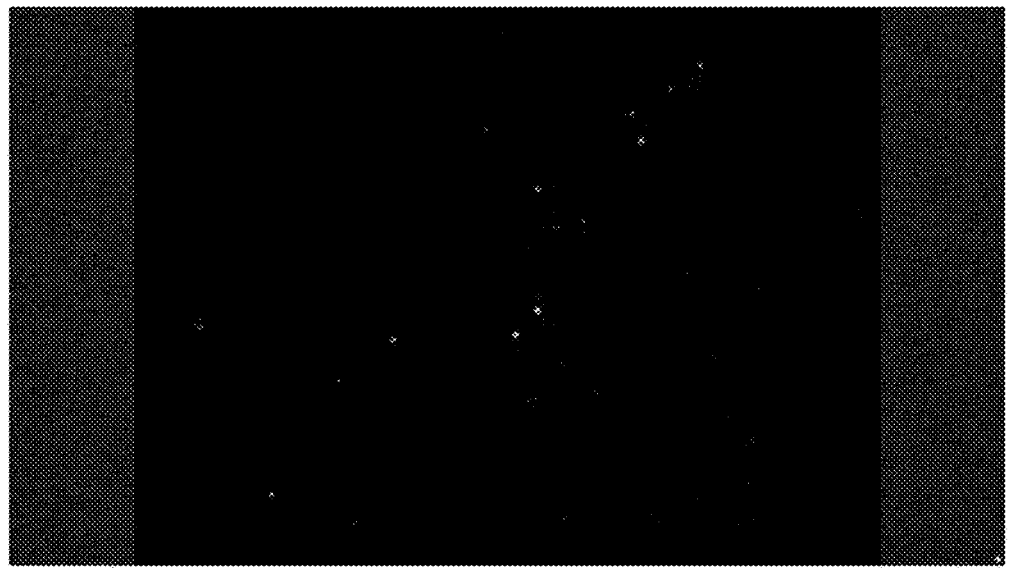
(a) 0.9W/cm² 60sec
(b) 1.0W/cm² 60sec

FIG. 27
(a-1) 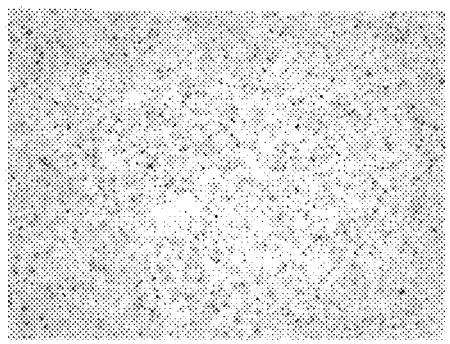 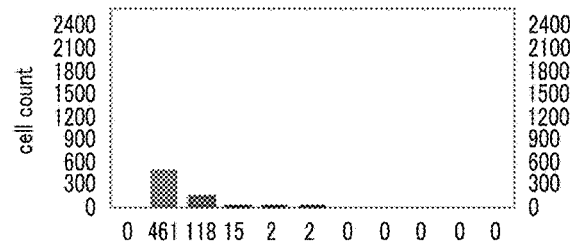
(a-2) 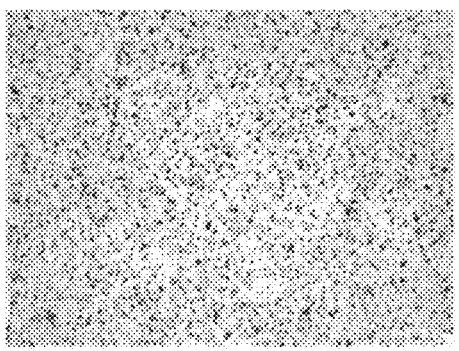 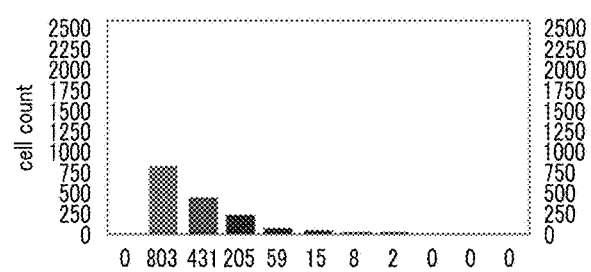
(b-1) 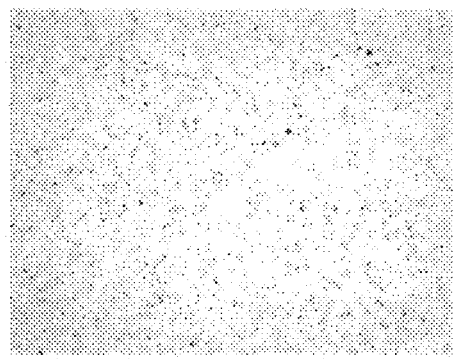 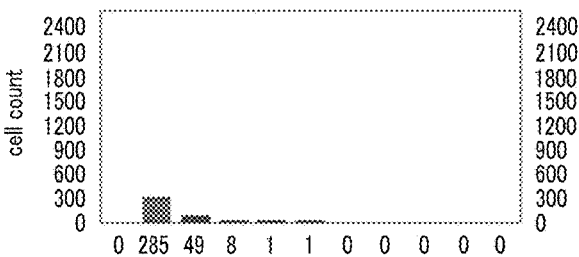
(b-2) 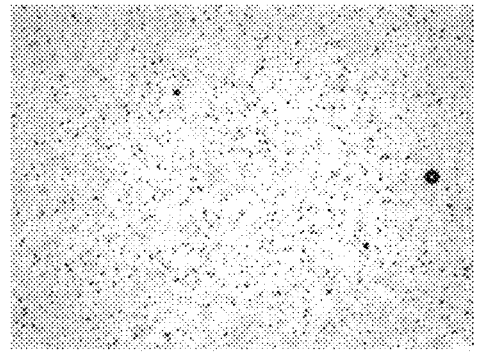 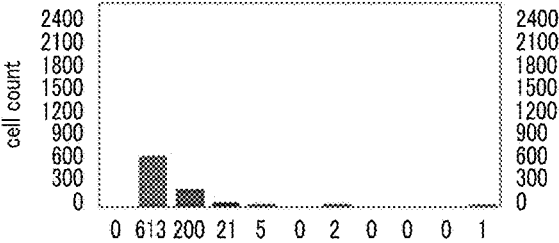

FIG. 28
(c-1) 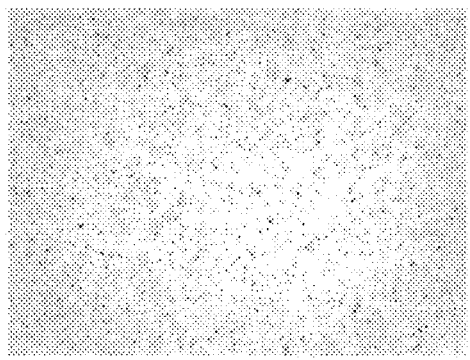 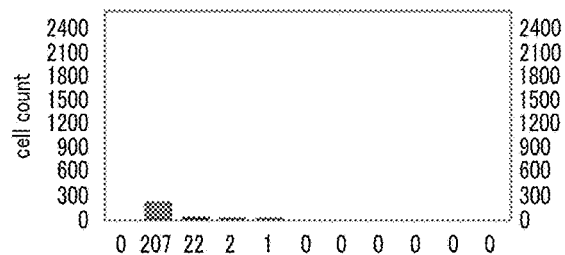
(c-2) 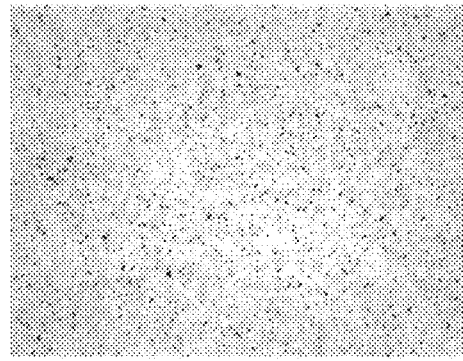 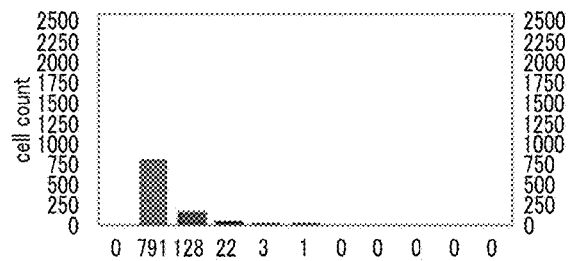

METHOD FOR MANUFACTURING BUBBLES AND BUBBLES

CROSS-REFERENCE TO RELATED APPLICATIONS

The present application is a U.S. National Phase of International Patent Application Serial No. PCT/JP2016/061350, entitled "BUBBLE PRODUCTION METHOD AND BUBBLES," filed on Apr. 7, 2016. International Patent Application Serial No. PCT/JP2016/061350 claims priority to Japanese Patent Application No. 2015-079625, filed on Apr. 8, 2015. The entire contents of each of the above-cited applications are hereby incorporated by reference in their entirety for all purposes.

TECHNICAL FIELD

The present invention relates to a method for manufacturing microbubbles or nanobubbles and to bubbles manufactured by the method for manufacturing microbubbles or nanobubbles. Particularly, the present invention relates to a method for manufacturing microbubbles or nanobubbles used for ultrasonic diagnosis and ultrasound therapy and to bubbles manufactured by the method for manufacturing microbubbles or nanobubbles.

RELATED ART

In recent years, in the various fields such as medical care, food, seafood farming, and waste water treatment, the use of micro-sized (about hundreds of micrometers) or nano-sized (equal to or smaller than hundreds of nanometers) bubbles has been examined. Particularly, in the medical field, a method is known in which an ultrasonic diagnosis is made for chest or abdomen by using the microbubbles as an ultrasound contrast agent.

The ultrasonic diagnosis method is a method of making a diagnosis by injecting an ultrasound contrast agent into the body through a vein or the like, irradiating a diagnosis site with ultrasonic waves, and making reflected waves (reflection echo) from the ultrasound contrast agent into an image. As the ultrasound contrast agent, minute air bubbles (microbubbles) each composed of an outer shell constituted of a protein, a lipid, or the like and a gas sealed in the outer shell are widely used.

In recent years, an ultrasound therapy method using the microbubbles has been examined (for example, PTL 1). More specifically, microbubbles in which a gene or a medical agent (drug) is sealed are injected into the body and transported to an affected site through blood vessels. When the microbubbles reach the vicinity of the affected site, ultrasonic waves are radiated to the microbubbles such that the microbubbles burst. In this way, the drug sealed in the microbubbles can be intensively administered to the affected site.

As methods for manufacturing the microbubbles, a supersaturation bubble generation method and a gas-liquid two-phase flow swirling method are known. The supersaturation bubble generation method is a method in which a gas is dissolved under a high pressure in a mixed liquid containing the constituent materials of the microbubbles and physiological saline, and then the pressure is reduced such that the microbubbles are generated in the mixed liquid. The gas-liquid two-phase flow swirling method is a method in which the aforementioned mixed liquid is stirred at a high speed such that the mixed liquid swirls, a gas is allowed to sufficiently drawn into the swirl, and then the swirl is stopped such that the microbubbles are generated in the mixed liquid.

In the aforementioned methods for manufacturing microbubbles, in order to generate the microbubbles, at least 1 to 10 L of the mixed liquid needs to be prepared. Furthermore, it is difficult to stably generate the microbubbles by using a small amount of mixed liquid (for example, several milliliters of the mixed liquid). In addition, unfortunately, the generated microbubbles vary in size.

CITATION LIST

Patent Literature

[PTL 1] JP-A-2002-209896

SUMMARY OF INVENTION

Technical Problem

The present invention has been made in consideration of the aforementioned problems of the related art, and an object thereof is to provide a method for manufacturing bubbles that can stably manufacture bubbles (microbubbles or nanobubbles) having a uniform size. Another object of the present invention is to provide bubbles having a uniform size.

Solution to Problem

The aforementioned objects are achieved by the present invention described below in (1) to (15).

(1) A method for manufacturing bubbles: including injecting an aqueous liquid into a container in a predetermined height; and vibrating the container at a number of revolution of equal to or higher than 5,000 rpm such that the aqueous liquid repeatedly collides with an inner surface of the container.

(2) The method for manufacturing bubbles described in (1), in which the vibrating the container is performed in a state where an internal pressure of the container is higher than 1.0 atm.

(3) The method for manufacturing bubbles described in (1) or (2), in which the container has a long shape, and the vibrating the container is performed by vibrating the container such that the container reciprocates in a longitudinal direction of the container or rotates mainly in the longitudinal direction.

(4) The method for manufacturing bubbles described in (3), in which provided that the height of the container is X (mm), a vibration width of the container in the longitudinal direction is in the range of 0.7X to 1.5X (mm).

(5) The method for manufacturing bubbles described in any one of (1) to (4), in which the container has a long shape, and the vibrating the container is performed by vibrating the container such that the container reciprocates in a transverse direction of the container or rotates mainly in the transverse direction.

(6) The method for manufacturing bubbles described in (5), in which a vibration width of the container in a horizontal direction is in the range of 0.3X to 0.8X (mm).

(7) The method for manufacturing bubbles described in any one of (1) to (6), further including injecting a predetermined gas into the container in a state where the container is sealed.

(8) The method for manufacturing bubbles described in any one of (1) to (7), in which in a state where the container containing the aqueous liquid is allowed to stand horizontally, provided that a height of the container is X (mm) and a height of a surface of the aqueous liquid in the container is Y (mm), a relationship of $0.2 \leq Y/X \leq 0.7$ is satisfied.

(9) The method for manufacturing bubbles described in any one of (1) to (8), further including vibrating again the container at the number of revolution of equal to or higher than 5,000 rpm after an internal pressure of the container is changed, after the vibrating the container.

(10) The method for manufacturing bubbles described in (9), in which the vibrating again the container is performed such that the internal pressure is 1 to 10 atm higher than the internal pressure in the vibrating the container.

(11) The method for manufacturing bubbles described in (9) or (10), in which the vibrating again the container is performed at a number of revolution different from the number of revolution in the vibrating the container.

(12) Bubbles micro-dispersed in an aqueous liquid, wherein the bubbles have an average diameter of 10 nm to 100 μm.

(13) The bubbles described in (12), in which the aqueous liquid contains at least one kind of component selected from the group consisting of water, sugars, salts, a drug, and an outer shell material constituting an outer shell of the bubbles.

(14) The bubbles described in (13), in which the outer shell is constituted with a micelle which is constituted with a monolayer of a molecule of an amphipathic material or a liposome which is constituted with a bilayer of the molecule of the amphipathic material.

(15) The bubbles described in any one of (12) to (14), further including at least one kind of gas selected from the group consisting of nitrous oxide, oxygen, hydrogen, helium, methane, ethane, propane, butane, pentane, cyclopropane, cyclobutane, cyclopentane, ethylene, propylene, propadiene, butene, acetylene, propyne, perfluoropropane, perfluorobutane, and perfluoropentane.

Advantageous Effects of Invention

According to the present invention, simply by vibrating a container at a predetermined number of revolution, a large amount of bubbles having a uniform size can be stably generated in an aqueous liquid. As a result, it is possible to provide a container containing the large amount of bubbles having the uniform size.

BRIEF DESCRIPTION OF DRAWINGS

FIG. 2 shows perspective views illustrating a state where a portion of an example of bubbles manufactured by the method for manufacturing bubbles of the present invention is cut. FIG. 1(a) shows a state where a portion of a bubble in which a gas is sealed in an outer shell is cut, and FIGS. 1(b) and 1(c) each show a state where a portion of a bubble in which a gas and a drug are sealed in an outer shell is cut.

FIG. 12(a) is a top view of the vicinity of the rubber stopper of the Mininert valve, and FIG. 12(b) is a cross-sectional view of FIG. 12(a) taken along the line X-X.

FIG. 16(a) shows the manufacturing container in a disassembled state, and FIG. 16(b) shows the manufacturing container in an assembled state.

FIG. 18 shows cross-sectional views for illustrating a manufacturing container used in a thirteenth embodiment of the method for manufacturing bubbles of the present invention. FIG. 18(a) shows the manufacturing container in a disassembled state, and FIG. 18(b) shows the manufacturing container in an assembled state.

FIG. 19(a) is a view for illustrating a state where an injection needle of a syringe is not yet pierced into a rubber stopper, and FIG. 19(b) is a view for illustrating a state where a fastening portion is fastened to a bottom plate portion after the injection needle is pulled out of the rubber stopper.

FIG. 23 shows fluorescent micrographs of a culture medium of cerebrovascular pericytes cultured for 48 hours at 37° C. FIG. 23(a) is an image of a sample irradiated with ultrasonic waves at an irradiance of 0.6 W/cm$^2$, and FIG. 23(b) is an image of a sample irradiated with ultrasonic waves at an irradiance of 0.8 W/cm$^2$.

FIG. 24 shows fluorescent micrographs of a culture medium of cerebrovascular pericytes cultured for 48 hours at 37° C. FIG. 24(a) is an image of a sample irradiated with ultrasonic waves at an irradiance of 0.9 W/cm$^2$, and FIG. 24(b) is an image of a sample irradiated with ultrasonic waves at an irradiance of 1.0 W/cm$^2$.

FIG. 27 shows micrographs and bubble diameter distribution graphs of bubbles obtained in Examples 18 and 19.

FIG. 28 shows micrographs and bubble diameter distribution graphs of bubbles obtained in Example 20.

DESCRIPTION OF EMBODIMENTS

Hereinafter, bubbles, a method for manufacturing bubbles, and a bubble manufacturing container of the present invention will be described based on suitable embodiments shown in the attached drawings.

1. Bubbles

First, prior to the description of the method for manufacturing bubbles and a bubble manufacturing container of the present invention, bubbles manufactured by the method for manufacturing bubbles of the present invention (bubbles of the present invention) will be described.

Figure 1:
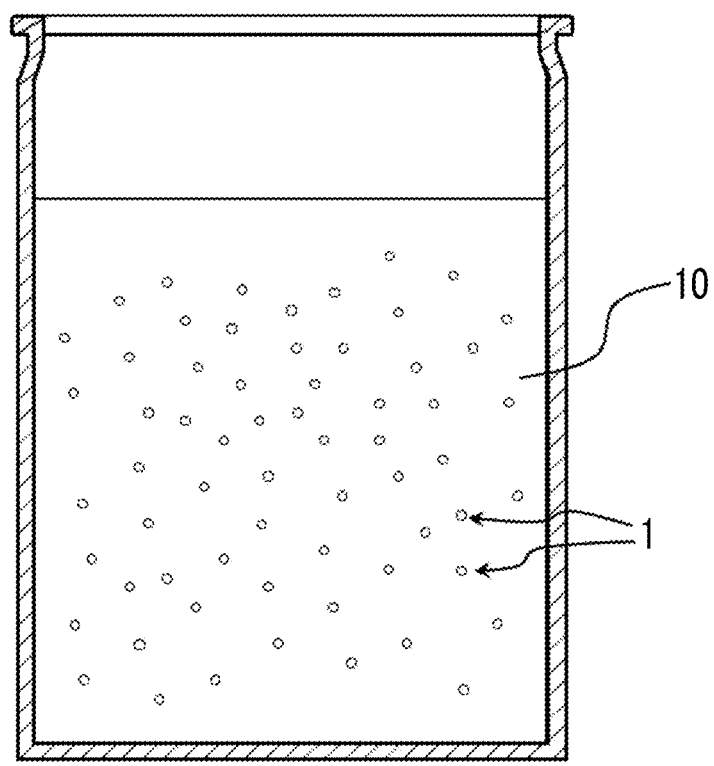
FIG. 1 is a view for illustrating an example of bubbles manufactured by a method for manufacturing bubbles of the present invention.

FIG. 1 is a view for illustrating an example of bubbles manufactured by the method for manufacturing bubbles of the present invention. FIG. 2 shows perspective views illustrating a state where a portion of an example of bubbles manufactured by the method for manufacturing bubbles of the present invention is cut. FIG. 2(a) shows a state where a portion of a bubble in which a gas is sealed in an outer shell is cut, and FIGS. 2(b) and 2(c) show a state where a portion of bubbles in which a gas and a drug are sealed in an outer shell is cut.

<First Constitution Example>

First, the bubbles 1 shown in FIG. 1 will be described.

The bubbles 1 (air bubbles) shown in FIG. 1 are formed by micro-dispersion of a gas 3 in an aqueous liquid 10. The bubbles 1 can be manufactured by first and second embodiments of the method for manufacturing bubbles of the present invention that will be described later. The bubbles 1 can be used in various fields such as medical care, food, seafood farming, and waste water treatment. In the present embodiment, a case where the bubbles 1 are used as an ultrasound contrast agent for ultrasonic diagnosis will be described.

The bubbles 1 constituted as above are formed using an aqueous medium as the aqueous liquid 10. Examples of the aqueous medium include water such as distilled water, pure water, ultrapure water, deionized water, and RO water, physiological saline (saline with a concentration of about 0.9%) such as Saline and phosphate buffered saline (PBS), an aqueous sugar solution obtained by mixing various sugars such as glucose and sucrose with distilled water, and the like. One kind of these can be used singly, or two or more kinds thereof can be used in combination.

The gas 3 is a substance that is in a gaseous state at the temperature (about 20° C.) at the time of manufacturing the bubbles 1. Furthermore, the gas 3 is the substance that is in the gaseous state even in a state where the bubbles 1 are injected into the body, that is, even at the body temperature (about 37° C.).

The gas 3 is not particularly limited, and examples thereof include: an inert gas such as air, nitrogen, nitrous oxide, oxygen, carbon dioxide, hydrogen, helium, argon, xenon, and krypton; sulfur fluoride such as sulfur hexafluoride, disulfur decafluoride, and trifluoromethyl sulfur pentafluoride; low-molecular weight hydrocarbons and halides thereof such as methane, ethane, propane, butane, pentane, cyclopropane, cyclobutane, cyclopentane, ethylene, propylene, propadiene, butene, acetylene, propyne, perfluoropropane, perfluorobutane, and perfluoropentane; ethers such as dimethyl ether; ketones; esters; and the like. Among these, one kind of substance can be used singly, or two or more kinds of substances can be used in combination. Among these substances, sulfur hexafluoride, perfluoropropane, perfluorobutane, and perfluoropentane are particularly preferable. The bubbles 1 in which these gases are sealed exhibit high stability in the body and are more reliably transported to an affected site (target site of treatment) or a target site of diagnosis through blood vessels.

The diameter of the bubbles 1 constituted with the aforementioned components changes with the change of conditions of each step of the method for manufacturing bubbles of the present invention. That is, the bubbles 1 to be manufactured have microsize (about hundreds of micrometers) or nanosize (about hundreds of nanometers).

The average diameter of the bubbles 1 is not particularly limited. However, specifically, the average diameter of the bubbles 1 is preferably about 10 nm to 1,000 μm, more preferably about 10 nm to 100 μm, and even more preferably about 50 nm to 2,000 nm. In a case where the average diameter of the bubbles 1 is within the aforementioned range, because the diameter of the bubbles 1 is small enough, the bubbles 1 can move smoothly in blood vessels due to the blood flow when being injected into the body by intravenous injection. Furthermore, the bubbles having such a diameter exhibit high stability in the blood vessels and are reliably transported to a target site without being destroyed while moving in blood vessels. Particularly, because nanobubbles exhibit high stability in the blood vessels, they are reliably transported to the target site substantially without being destroyed.

Generally, gas-containing bubbles have a property of efficiently reflecting ultrasonic waves from the interface between a liquid and a gas. Therefore, in the bubbles 1 having the average diameter within the aforementioned range, the area of the interface between the liquid (aqueous liquid 10 or blood in a case where the bubbles 1 are injected into the body as an ultrasound contrast agent) and the gas 3 is large enough, and hence the bubbles 1 are effectively used as the ultrasound contrast agent.

The bubbles 1 constituted as above can also be used in the fields other than a medical field, such as food, seafood farming, and waste water treatment. Particularly, the stability of the bubbles 1 having the average diameter within the aforementioned range can be sufficiently improved, and hence it is easy to handle the bubbles 1. Therefore, the bubbles 1 can be used in various fields.

<Second Constitution Example>

Next, the bubble 1 shown in FIG. 2(a) will be described. Herein, the differences between the bubbles 1 of the first constitution example and the bubbles 1 of the second constitution example will be mainly described, and the same details will not be described.

The bubble 1 (air bubble) shown in FIG. 2(a) can be manufactured by third and fifth to thirteenth embodiments of the method for manufacturing bubbles of the present invention that will be described later. The bubble 1 shown in FIG. 2(a) has an outer shell 2 (spherical membrane) constituting a shell of the bubble 1 and the gas 3 sealed in the outer shell 2. Such a bubble 1 can be used in various fields such as medical care, food, seafood farming, and waste water treatment. In the present embodiment, a case where the bubbles 1 are used as an ultrasound contrast agent for ultrasonic diagnosis will be described. Hereinafter, each component constituting the bubbles 1 will be described.

The outer shell 2 functions to retain the gas 3 sealed therein within the bubble 1.

The outer shell 2 is mainly constituted with an amphipathic material (outer shell material) having properties (substituents) of showing both the hydrophobicity and the hydrophilicity in a single molecule. The amphipathic material is not particularly limited, and examples thereof include: a protein such as albumin, a phospholipid such as a polycationic lipid, phosphatidylcholine, phosphatidylserine, phosphatidylethanolamine, and phosphatidalethanolamine; a higher fatty acid such as palmitic acid and stearic acid; sugars such as galactose; sterols such as cholesterol and sitosterol; a surfactant; a natural or synthetic polymer; a fluorescent dye; an antibody; a labeling metal; and the like. Among these, one kind of material can be used singly, or two or more kinds of materials can be used in combination.

The amphipathic material constituting the outer shell 2 is disposed in the form of a sphere in an aqueous medium such that a hydrophobic group becomes inside and a hydrophilic group becomes outside, although such a property is not shown in FIG. 2. Due to this property, the outer shell 2 becomes a micelle constituted with a monolayer of a molecule of the amphipathic material or becomes a liposome (spherical molecular membrane) constituted with a bilayer of the molecule of the amphipathic material.

The diameter of the bubble 1 constituted with the aforementioned components is the same as the diameter of the bubble 1 shown in FIG. 1.

Generally, a bubble containing a gas in an outer shell has a property of efficiently reflecting ultrasonic waves from the interface between the outer shell and the gas. Therefore, in the bubbles 1 having the average diameter with the aforementioned range, the area of the interface between the outer shell 2 and the gas 3 is large enough, and hence the bubbles 1 are effectively used as the ultrasound contrast agent.

<Third Constitution Example>

Next, the bubbles 1 shown in FIGS. 2(b) and 2(c) will be described.

Herein, the differences between the bubbles of the first and second constitution examples and the bubbles of the present embodiment will be mainly described, and the same details will not be described.

The bubbles 1 shown in FIGS. 2(b) and 2(c) can be manufactured by fourth to thirteenth embodiments of the method for manufacturing bubbles of the present invention that will be described later. Such a bubble 1 has the outer shell 2 constituting a shell of the bubble 1 and a gas 3 and a drug 4 sealed in the outer shell 2. The bubble 1 is used for ultrasound therapy and ultrasonic diagnosis. FIG. 2(b) shows the bubble 1 in which the drug 4 is sealed in the outer shell 2 in a gaseous state or a solid state, and FIG. 2(c) shows the bubble 1 in which the drug 4 is sealed in the outer shell 2 in a liquid state.

The outer shell 2 functions to retain the gas 3 or the drug 4 sealed therein within the bubble 1 and to protect the drug 4 until the bubble 1 is transported to an affected site.

In the bubbles 1 shown in FIGS. 2(b) and 2(c), the drug 4 is an active component for treating various diseases such as prostate cancer, uterine myoma, myocardial infarction, and cerebral infraction. The drug 4 is transported to the affected site in a state of being contained in the bubble 1, and the outer shell 2 bursts in the vicinity of the affected site by being irradiated with ultrasonic waves. In this way, the drug 4 is administered to the affected site. The drug 4 may be contained in the outer shell 2 itself or adsorbed onto an outer surface of the outer shell 2, although this constitution is not shown in the drawings.

The drug 4 is not particularly limited as long as it is effective for treating the diseases, and includes a gene, a medical agent, and the like. Specific examples thereof include a peptide, an antibody, oligosaccharide, polysaccharide, a gene, oligonucleotide, antisense oligonucleotide, siRNA, ribozyme, a triple helix molecule, a viral vector, a plasmid, a low-molecular weight organic compound, an anticancer drug, a metal, and the like. Among these, one kind of drug can be used singly, or two or more kinds of drugs can be used in combination.

The volume ratio between the drug 4 and the gas 3 is preferably about 1:99 to 90:10, more preferably about 10:90 to 70:30, and even more preferably about 40:60 to 60:40. In a case where the volume ratio between the drug 4 and the gas 3 is within the aforementioned range, the stability of the bubble 1 can be improved, and hence the bubble 1 can be more reliably transported to the vicinity of the affected site. Furthermore, when the outer shell 2 bursts in the vicinity of the affected site, a sufficient amount of drug can be administered to the affected site. Therefore, the affected site can be more efficiently treated.

Similarly to the bubble 1 shown in FIG. 2(a), the diameter of the bubble 1 constituted with the aforementioned components changes with the change of the conditions of each step of the method for manufacturing bubbles of the present invention.

At an affected site where a cancer cell exists, neovessels having a diameter smaller than that of a normal vessel extend to the cancer cell from the peripheral blood vessels of the affected site. In a case where the bubbles 1 have an average diameter of about 200 to 300 nm, the bubbles 1 can be smoothly transported even in the neovessels and can reach the cancer cell. That is, those bubbles 1 can be suitably used for cancer treatment. Furthermore, it is possible to cause some of the bubbles 1 to pass through the vessel wall and to be incorporated into the cancer cell.

In a case where the bubbles 1 have an average diameter of about 600 to 900 nm, the bubbles 1 can be smoothly transported in blood vessels in the brain, and the position thereof can be clearly specified in an ultrasonic image. Therefore, the bubbles 1 can be suitably used in brain treatment (for example, endovascular treatment of brain).

The average diameter of the bubbles 1 shown in FIG. 1 and FIGS. 2(a) to 2(c) can be measured by observation using, for example, a laser diffraction-scattering method, a nanoparticle tracking analysis method, an electric resistance method, an atomic force microscope (AFM), a laser microscope, and the like. As a device for measuring by AFM, for example, it is possible to use a resonant particle measurement system (trade name: ARCHIMEDES) manufactured by Malvern Instruments Ltd.

The bubbles 1 described above can be manufactured by the method for manufacturing bubbles of the present invention that will be described below. Hereinafter, the method for manufacturing bubbles of the present invention will be specifically described.

2. Method for Manufacturing Bubbles

First Embodiment

Next, a first embodiment of the method for manufacturing bubbles of the present invention will be described. The bubbles 1 shown in FIG. 1 described above can be manufactured by the method for manufacturing bubbles of the present embodiment.

Figure 3:
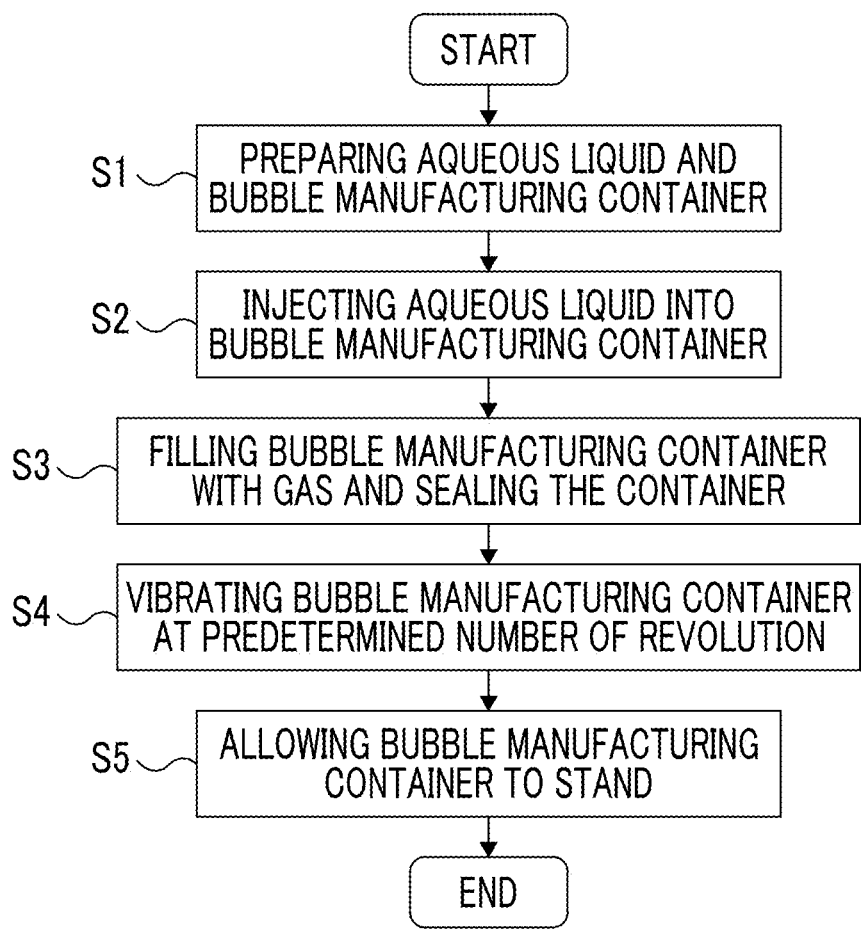
FIG. 3 is a flow chart for illustrating a first embodiment of the method for manufacturing bubbles of the present invention.

FIG. 3 is a flow chart for illustrating the first embodiment of the method for manufacturing bubbles of the present invention. FIGS. 4(a) to 4(d) are cross-sectional views of a manufacturing container for illustrating the first embodiment of the method for manufacturing bubbles of the present invention. FIG. 5 is a partially enlarged view for illustrating a state where an aqueous liquid violently collides with an inner surface (top surface) of a container in a step of vibrating a container shown in FIG. 4(c).

In the following description, the upper side in each of FIGS. 4(a) to 4(d) and FIG. 5 will be referred to as "top", and the lower side in each of FIGS. 4(a) to 4(d) and FIG. 5 will be referred to as "bottom".

As shown in FIG. 3, the method for manufacturing bubbles of the present embodiment includes five steps consisting of Steps (S1) to (S5). Step (S1) is a step of preparing an aqueous liquid and a bubble manufacturing container (hereinafter, simply referred to as "manufacturing container") into which the aqueous liquid is injected. Step (S2) is a step of injecting the aqueous liquid into the manufacturing container to a predetermined height. Step (S3) is a step of sealing the manufacturing container in a state where the manufacturing container is filled with a gas. Step (S4) is a step of vibrating the manufacturing container at a predetermined number of revolution such that the aqueous liquid repeatedly collides with the inner surface of the container. Step (S5) is a step of allowing the manufacturing container to stand. Hereinafter, these steps will be sequentially described.

[S1] Preparation Step

First, the aqueous liquid 10 is prepared.

In the method for manufacturing bubbles of the present embodiment, as the aqueous liquid 10, the aqueous medium described above is used.

The inventor of the present invention found that the higher the concentration water in the aqueous liquid 10 becomes, the smaller the diameter of the bubbles 1 generated becomes, and the greater the amount of the bubbles 1 generated becomes. Accordingly, in a case where water (distilled water) is used as the aqueous liquid 10, it is possible to generate more bubbles 1 having a smaller diameter.

In a case where an aqueous sugar solution is used as the aqueous liquid 10, the lower the concentration of sugar in the aqueous sugar solution becomes, that is, the higher the concentration of water becomes, the smaller the diameter of the bubbles 1 generated becomes, and the greater the amount of the bubbles 1 generated becomes. Accordingly, by appropriately setting the type of the aqueous medium and the condition of Step (S4), it is possible to obtain the bubbles 1 having an intended diameter.

The concentration of sugar in the aforementioned aqueous sugar solution is not particularly limited, but is preferably about 0.01 to 60 wt %, more preferably about 0.1 to 50 wt %, and even more preferably about 5 to 30 wt %. In a case where the aqueous sugar solution in which the concentration of sugar is within the aforementioned range is used, in Step (S4) which will be described later, the stability of the bubbles 1 generated in the aqueous liquid 10 is improved. Therefore, the bubbles 1 are more reliably prevented from accidentally bursting, and temporal stability of the bubbles 1 is improved.

Then, a manufacturing container 20 (first embodiment of the bubble manufacturing container) is prepared.

The manufacturing container 20 includes a container body 21 accommodating the aqueous liquid 10 and having an opening portion, and a lid 22 for sealing the container body 21.

The container body 21 is not particularly limited, but preferably looks like a bottomed cylinder as shown in FIG. 4(a). In the present embodiment, as the container body 21, a vial having a volume of about 0.5 to 20 ml is used. In the method for manufacturing bubbles of the present invention, even in a case where such a vial with a small volume is used as the container body 21, when the container body 21 is sealed with the lid 22, an appropriate pressure is applied to the aqueous liquid 10 within the sealed space in the container body 21. Accordingly, the bubbles 1 having a uniform size can be stably obtained. Particularly, in a case where a vial having a volume of about 0.5 to 1.5 ml is used, in a single manufacturing container 20, a bubble-containing liquid of about 0.3 to 0.6 ml that is a volume necessary for a single session of ultrasonic diagnosis can be manufactured. In this case, at the time of ultrasonic diagnosis, the bubble-containing liquid in a single manufacturing container 20 can be used up. Therefore, it is possible to eliminate a waste of the manufactured bubble-containing liquid.

The vial having such a small volume (volume: about 0.5 to 20 ml) has dimensions in which a length X in a longitudinal direction is about 35 to 60 mm and an outer diameter R is about 10 to 40 mm.

As shown in FIGS. 4(b) to 4(d), the lid 22 includes a disk-like rubber stopper (septum) 221 that adheres to a vial mouth of the container body 21 and a fastening portion 222 that fixes the rubber stopper 221 to the vial mouth of the container body 21.

The rubber stopper 221 is not particularly limited, but for example, a rubber stopper made of silicon can be used.

The fastening portion 222 is constituted such that it covers the edge of the rubber stopper 221. When seen in a plan view, the fastening portion 222 has an opening approximately at the center thereof. On the inner circumferential surface of the fastening portion 222 on the vial mouth side and on the outer circumferential surface of the container body 21 on the vial mouth side, screw grooves that can be screwed with each other are formed (not shown in the drawing). By screwing the screw grooves with each other, the rubber stopper 221 is fixed to the vial mouth of the container body 21 in a state of adhering to the vial mouth. Furthermore, by caulking the vial mouth of the container body 21 with the fastening portion 222, the container body 21 and the fastening portion 222 can be fixed to each other in a state where the rubber stopper 221 adheres to the vial mouth of the container body 21.

[S2] Step of Injecting Aqueous Liquid Into Manufacturing Container

The prepared aqueous liquid 10 is injected into the container body 21 (manufacturing container 20) to a predetermined height. In the present embodiment, as shown in FIG. 4(a), the liquid is injected to Y [mm]. Accordingly, as shown in FIG. 4(a), the container body 21 into which the aqueous liquid 10 is injected has a void portion 11 on the top portion thereof.

In the present embodiment, in a state where the container body 21 (manufacturing container 20) into which the aqueous liquid 10 is injected is allowed to stand horizontally, provided that the height (length in the longitudinal direction) of the container body 21 is X [mm] and the level of the surface of the aqueous liquid 10 in the container body 21 is Y [mm], it is preferable that a relationship of $0.2 \leq Y/X \leq 0.7$ is satisfied. In a case where the aforementioned relationship is satisfied, due to the existence of the void portion 11 that is large enough, in Step (S4), it is possible to make the aqueous liquid 10 more violently collide with the top and bottom surfaces and the lateral surface (particularly, the top and bottom surfaces) of the manufacturing container 20. Due to the collision, shock waves occur in the aqueous liquid 10, and hence the bubbles 1 can be easily formed in the aqueous liquid 10.

The aforementioned X and Y more preferably satisfy a relationship of $0.3 \leq Y/X \leq 0.5$, and even more preferably satisfy a relationship of $0.35 \leq Y/X \leq 0.4$. In this way, in Step (S4), bubbles can be more easily formed in the aqueous liquid 10.

[S3] Step of Sealing Manufacturing Container

Then, the container body 21 is sealed in a state of being filled with the gas 3 (see FIG. 4(b)). Specifically, in the void portion 11 of the container body 21 into which the aqueous liquid 10 is injected, purging is performed using the gas 3, and then the lid 22 is fastened to the opening portion (vial mouth) of the container body 21. In this way, the aqueous liquid 10 and the gas 3 are sealed in the manufacturing container 20.

As a method for performing the purging in the void portion 11 of the container body 21 by using the gas 3, for example, the container body 21 into which the aqueous liquid 10 is injected is moved into a chamber. Thereafter, the air in the chamber is substituted with the gas 3, and then the lid 22 is fastened to the opening portion of the container body 21. In this way, the aqueous liquid 10 and the gas 3 can be sealed in the manufacturing container 20.

As the gas 3, the various gases described above are used.

[S4] Step of Vibrating Manufacturing Container

Then, the manufacturing container 20 is vibrated such that the aqueous liquid 10 repeatedly collides with the top and bottom surfaces and the lateral surface (particularly, the top and bottom surfaces) of the manufacturing container 20. In the present embodiment, as shown in FIG. 4(c), the manufacturing container 20 is vibrated such that the container reciprocates approximately in the longitudinal direction (a vertical direction in FIG. 4(c)) thereof.

In this step, the manufacturing container 20 (lower view in FIG. 4(c)) sealed in Step (S3) is vibrated upwardly (middle view in FIG. 4(c)). As a result, the aqueous liquid 10 moves to the vicinity of the middle of the manufacturing container 20. In a case where the manufacturing container 20 is further vibrated upwardly, the aqueous liquid 10 moves to the top portion of the manufacturing container 20 and collides with the bottom surface (rubber stopper 221) of the lid 22 (upper view in FIG. 4(c)). At this time, as shown in FIG. 5, shock waves occur. Due to the pressure of the shock waves, the gas 3 is micro-dispersed in the aqueous liquid 10, and hence the bubbles 1 are formed. The bubbles 1 contain the gas 3 in which the aqueous liquid 10 is micro-dispersed or dissolved due to vibration.

Meanwhile, the manufacturing container 20 (upper view in FIG. 4(c)) is vibrated downwardly (middle view in FIG. 4(c)). As a result, the aqueous liquid 10 moves to the vicinity of the middle of the manufacturing container 20. In a case where the manufacturing container 20 is further vibrated downwardly, the aqueous liquid 10 moves to the bottom portion of the manufacturing container 20 and collides with the bottom surface of the manufacturing container 20 (lower view in FIG. 4(c)). At this time, as shown in FIG. 5, the shock waves also occur.

When the manufacturing container 20 is vibrated in the vertical direction, the aqueous liquid 10 also collides with the inner lateral surface of the manufacturing container 20. At this time, as shown in FIG. 5, the shock waves also occur.

By repeatedly performing the aforementioned operation, it is possible to stably generate a large amount of bubbles 1 having a uniform size in the aqueous liquid 10.

In the method for manufacturing bubbles of the present invention, in order to obtain the bubbles 1 that are fine enough and have a uniform diameter, the manufacturing container 20 is vibrated at the number of revolution of equal to or higher than 5,000 rpm. As a result, the magnitude (pressure) of the shock waves that occur when the aqueous liquid 10 collides with the manufacturing container 20 becomes high enough, fine bubbles 1 are generated in the aqueous liquid 10, and the diameter of the bubbles can be made uniform. In a case where the number of revolution of the manufacturing container 20 is set to be low within the aforementioned range, the magnitude of the occurring shock waves is reduced, and hence the bubbles 1 having a relatively large diameter can be generated. Furthermore, in a case where the number of revolution is set to be high, the magnitude of the occurring shock waves increases, and hence the bubbles 1 having a relatively small diameter can be generated. In the present specification, "number of revolution" of the manufacturing container 20 refers to the number of times that the manufacturing container 20 travels the whole vibration route thereof per unit time. For example, in a case where the manufacturing container 20 vibrates at 5,000 rpm, it means that the manufacturing container 20 travels (vibrates) in 5,000 times the whole vibration route for 1 minute.

The number of revolution of the manufacturing container 20 is more preferably equal to or higher than 5,500 rpm, and even more preferably 6,000 to 20,000 rpm. In a case where the number of revolution of the manufacturing container 20 is within the aforementioned range, it is possible to more reliably prevent the bubbles 1 generated by vibration from being destroyed due to collision or from coarsening by being combined with each other. As a result, it is possible to generate a large amount of bubbles 1 having a more uniform diameter in the aqueous liquid 10 with reducing the diameter of the bubbles 1.

As a device that can vibrate the manufacturing container 20 at the number of revolution described above, for example, a bead-type high-speed cell disruption system (homogenizer) can be used. Specifically, Precellys manufactured by bertin Technologies and the like can be used.

The pressure of the shock waves that occur when the aqueous liquid 10 collides with the manufacturing container 20 is preferably 40 kPa to 1 GPa. In a case where the pressure of the shock waves that occur at the time of collision between the aqueous liquid 10 and the manufacturing container 20 is within the aforementioned range, the bubbles 1 generated in the aqueous liquid 10 become finer, and the size thereof can be made more uniform. Particularly, the higher the pressure of the shock waves that occur at the time of collision between the aqueous liquid 10 and the manufacturing container 20 is, the finer the generated bubbles 1 can become.

At the time of vibrating the manufacturing container 20, a vibration width of the manufacturing container 20 in the longitudinal direction is preferably about 0.7X to 1.5X [mm], and more preferably about 0.8X to 1X [mm]. In this way, when the manufacturing container 20 vibrates, it is possible to cause the aqueous liquid 10 to reliably collide with the bottom surface of the manufacturing container 20 and the lid 22, and to sufficiently increase the number of times the aqueous liquid 10 collides with the bottom surface of the manufacturing container 20 and the lid 22. Furthermore, in a case where the manufacturing container 20 is vibrated at the sufficient vibration width described above, the speed at which the aqueous liquid 10 moves in the manufacturing container 20 increases. Therefore, the magnitude of the shock waves that occur when the aqueous liquid 10 collides with the bottom surface of the manufacturing container 20 and the lid 22 sufficiently increases. As a result, it is possible to generate a large amount of fine bubbles 1 in the aqueous liquid 10.

When the manufacturing container 20 is reciprocated in the vertical direction, the manufacturing container 20 is preferably vibrated in a transverse direction (horizontal direction) thereof as well. In this way, the aqueous liquid 10 also collides with the inner lateral surface of the manufacturing container 20, and hence more shock waves can be generated in the aqueous liquid 10. The vibration width of the manufacturing container 20 in the transverse direction is preferably about 0.3X to 0.8X [mm], and more preferably about 0.5X to 0.7X [mm]. In this way, the aforementioned effects are more markedly exhibited.

The manufacturing container 20 may be vibrated only in the transverse direction thereof. In this case, the vibration width of the manufacturing container 20 in the transverse direction (horizontal direction) is preferably the same as the vibration width in the aforementioned transverse direction. In a case where the vibration width is the same, the aqueous liquid 10 reliably collides with the inner lateral surface of the manufacturing container 20, and hence more shock waves can occur in the aqueous liquid 10. As a result, a large amount of fine bubbles 1 can be generated in the aqueous liquid 10.

In this step, it is preferable to vibrate the manufacturing container 20 such that an instantaneous relative speed between the manufacturing container 20 and the aqueous liquid 10 in the manufacturing container 20 becomes equal to or higher than 40 km/h when the aqueous liquid 10 collides with the top and bottom surfaces and the lateral surface of the manufacturing container 20. It is more preferable to vibrate the manufacturing container 20 such that the instantaneous relative speed becomes equal to or higher than 50 km/h. In a case where the aforementioned condition is satisfied, it is possible to sufficiently increase the pressure of the shock waves that occur when the aqueous liquid 10 collides with the manufacturing container 20. As a result, the bubbles 1 generated in the aqueous liquid 10 become finer, and the size thereof can be made more uniform.

The period of time for which the manufacturing container 20 is vibrated under the aforementioned condition is preferably about 10 to 120 seconds, and more preferably about 30 to 60 seconds. In a case where the vibration time of the manufacturing container 20 is within the aforementioned range, the number of times that the aqueous liquid 10 collides with the manufacturing container 20 sufficiently increases, and hence a large amount of bubbles 1 can be generated in the aqueous liquid 10. In a case where the vibration time of the manufacturing container 20 is set to be long within the aforementioned range, the amount of bubbles 1 generated in the aqueous liquid 10 can be further increased.

The average diameter of the bubbles 1 generated in the aqueous liquid 10 can be adjusted by changing the number of revolution of the manufacturing container 20 within the aforementioned range. In the present embodiment, by using the aforementioned aqueous medium as the aqueous liquid 10, nanobubbles having a size of about tens of nanometers to hundreds of nanometers can be stably generated.

In the present embodiment, the manufacturing container 20 is vibrated such that the container reciprocates practically in the longitudinal direction thereof, but the method for vibrating the manufacturing container 20 is not limited thereto. For example, the manufacturing container 20 may be vibrated such that the container rotates mainly in the transverse direction and/or the longitudinal direction thereof. Even in this case, the aqueous liquid 10 in the manufacturing container 20 repeatedly collides with the top and bottom surfaces and the lateral surface of the manufacturing container 20, and as a result, the shock waves occur. By using the aforementioned vibrating method, a large amount of bubbles 1 having a uniform size can also be stably generated in the aqueous liquid 10.

[S5] Step of Allowing Manufacturing Container to Stand

After the manufacturing container 20 is vibrated under the aforementioned conditions, the manufacturing container 20 is allowed to stand (see FIG. 4(d)). In this way, the large amount of bubbles 1 having the uniform size (see FIG. 1) can be stably manufactured in the manufacturing container 20. In addition, the manufacturing container 20 containing the large amount of the bubbles 1 having the uniform size is obtained.

It is preferable to perform the aforementioned Step (S2), Step (S3), and Step (S4) by making the temperature of the aqueous liquid 10 remain constant. In this way, the characteristics (viscosity and the like) of the aqueous liquid 10 are stabilized in the manufacturing process of the bubbles, and hence the bubbles 1 having the uniform diameter can be stably generated in the aqueous liquid 10. Examples of the method for making the temperature of the aqueous liquid 10 remain constant include a method of performing each of the aforementioned Steps (S2) to (S4) in a glove box or a thermostatic bath. Particularly, in the present embodiment, the manufacturing container 20 is vibrated at a high speed in Step (S4). Therefore, due to the collision between the aqueous liquid 10 and the inner surface of the manufacturing container 20, the manufacturing container 20 is easily heated. However, by vibrating the manufacturing container 20 in the thermostatic bath, it is possible to reliably prevent the temperature increase of the aqueous liquid 10. As a result, the bubbles 1 having the uniform diameter can be stably generated in the aqueous liquid 10.

Through the aforementioned Steps (S1) to (S5), the bubbles 1 having an average diameter of about 10 nm to 1,000 µm are manufactured. In the present embodiment in which the aqueous medium described above is used as the aqueous liquid 10, it is easy to generate the bubbles 1 having a small average diameter. Particularly, in the present embodiment, a large amount of bubbles 1 having an average diameter of 10 nm to 1,000 nm can be generated.

In the method for manufacturing bubbles of the related art, a large-scale reflux device or various systems (a tube, a nozzle, a compressor, and the like) constituting a bubble manufacturing device are required. Therefore, in a case where bubbles used in the field of food or medical care are manufactured, it is difficult to maintain a clean and sterile environment. In contrast, in the present invention, because the manufacturing container 20 having high airtightness is used for manufacturing the bubbles 1, in a state where the manufacturing container 20 contains the aqueous liquid 10 and the gas 3, a sterilization treatment such as γ-ray sterilization may be performed on the manufacturing container 20. In this way, the interior of the manufacturing container 20 is sterilized, and hence the bubbles 1 can be manufactured in a sterile environment. Accordingly, the bubbles 1 manufactured in this way can be suitably used in the field of food or medical care.

The bubbles 1 obtained as above can stably exist in the aqueous liquid 10. Therefore, the manufacturing container 20 containing the obtained bubbles (hereinafter, simply referred to as "bubble-containing container") can be stored for a long period of time at room temperature. Specifically, the container can be stored for 6 to 24 months. Furthermore, even after the container is stored for such a long period of time, the stability of the bubbles 1 in the aqueous liquid 10 is still high. Consequently, the bubble-containing container does not need to be vibrated again and can be directly used. In addition, because the manufacturing container 20 having a small volume is used as a manufacturing container, the unit cost of the bubble-containing container can be reduced. As a result, the bubble-containing container obtained as above has an advantageous of being easily handled in medical facilities and the like.

[S6] Step of Centrifugation Treatment

In the method for manufacturing bubbles of the present embodiment, after Step (S5), a centrifugation treatment may be performed on the bubble-containing container. By this treatment, the bubbles 1 generated in the manufacturing container 20 can be separated based on the intended size.

Specifically, in a case where the centrifugation treatment is performed on the bubble-containing container, the bubbles 1 having a large diameter tend to move to a top layer of the manufacturing container 20 while the bubbles 1 having a small diameter tend to move to a bottom layer of the manufacturing container 20. Accordingly, in a case where the liquid (supernatant) of the top layer of the manufacturing container 20 is removed using aspiration means (a syringe, a pipette, or the like), the average diameter of the bubbles 1 in the bubble-containing liquid remaining in the manufacturing container 20 becomes smaller than the average diameter of the bubbles 1 in the bubble-containing liquid obtained after Step (S5). Furthermore, the average diameter of the bubbles 1 in the bubble-containing liquid (supernatant) aspirated by the aspiration means becomes larger than the average diameter of the bubbles 1 in the bubble-containing liquid obtained after Step (S5). In this way, by using the centrifugation treatment, the bubbles 1 having a more monodispersed bubble diameter distribution can be obtained.

Furthermore, by adding a substance, having a specific gravity different from that of the aqueous liquid 10, to the bubble-containing liquid and performing the centrifugation treatment, the bubbles 1 having the large diameter easily move to the top layer while the bubbles 1 having the small diameter easily move to the bottom layer. As a result, the bubbles 1 having a more monodispersed bubble diameter distribution can be obtained.

For example, in a case where a bubble-containing liquid containing the bubbles 1 having an average diameter of 600 nm is obtained through Steps (S1) to (S5), by appropriately setting the condition of the centrifugation treatment, it is possible to obtain a bubble-containing liquid containing the bubbles 1 having an average diameter of 200 to 300 nm. In a case where such a bubble-containing liquid is used as the ultrasound contrast agent, because there are no bubbles 1 having a relatively large diameter, it is possible to obtain a better high-definition image having a high resolution.

The condition of the centrifugation treatment is appropriately set according to the average diameter of the bubbles 1 to be separated. For example, the condition is set such that a centrifugal acceleration of about 1×g to 22,000×g is applied to the bubble-containing liquid for about 30 seconds to 24 hours. In a case where the centrifugal acceleration is set to be low (about 1×g to 100×g), by performing the treatment for a long period of time (for about 12 hours to 24 hours), the bubbles 1 having the more monodispersed bubbles diameter distribution can be obtained. In a case where the centrifugal acceleration is set to be high (100×g to 22,000×g), by performing the treatment for a relatively short period of time (for about 30 seconds to 12 hours), the bubbles 1 having the more monodispersed bubbles diameter distribution can be obtained. By performing the centrifugation treatment under the aforementioned condition, the bubbles 1 having an intended average diameter can be efficiently separated.

A centrifuge that can perform the centrifugation treatment on the bubble-containing container at the aforementioned centrifugal acceleration is not particularly limited, and for example, a high-speed refrigerated microcentrifuge such as "TOMY MX-301" (trade name, manufactured by TOMY SEIKO CO., LTD.) can be used. In a case where the high-speed refrigerated microcentrifuge is used, by setting the number of revolution thereof to be about 50 to 2,000 rpm, the centrifugal acceleration (centrifugal force) within the aforementioned range is applied to the bubble-containing liquid.

The centrifugation treatment may be performed once or plural times.

3. How to Use

The bubble-containing container obtained as above is used for making an ultrasonic diagnosis for patients.

Specifically, first, an injection needle of a syringe is pierced into the rubber stopper 221 of the lid 22. Then, the bubble-containing liquid is aspirated from the interior of the bubble-containing container. Thereafter, the injection needle is pulled out of the rubber stopper 221, and a blood vessel (for example, a vein) of a patient is pierced with the injection needle of the syringe into which the bubble-containing liquid is aspirated, such that the bubble-containing liquid is injected into the blood vessel. In this way, the bubbles 1 are transported to an affected site through the blood flow. The lid 22 may be removed from the bubble-containing container (manufacturing container 20), and the bubble-containing liquid may be aspirated from the interior of the bubble-containing container by using a syringe.

During the ultrasonic diagnosis, at the timing when the bubbles 1 reach a target site of diagnosis, the bubbles 1 are irradiated with ultrasonic waves for diagnosis having a frequency and an intensity at which the bubbles 1 may not burst (the ultrasonic waves are radiated to the bubbles 1). Then, the signals (reflection echo) reflected from the target site of diagnosis are received and subjected to data processing, thereby imaging the target site of diagnosis. In this way, an ultrasonic diagnosis can be made.

As a device performing the irradiation of the ultrasonic waves and receiving the reflection waves from the bubbles 1, known ultrasonic probes can be used.

The bubble-containing container obtained as above can be used in various fields, in addition to be used for the ultrasonic diagnosis. For example, the bubbles 1 in the bubble-containing container obtained as above exhibit a germicidal effect with respect to water or food and have an effect of keeping the freshness of food. Furthermore, in a liquid containing the bubbles 1, water, and oil (hydrophobic component), a large amount of oil can be mixed with water. By exploiting such an effect, it is possible to cook with inhibiting the separation of water from oil in food. Accordingly, the obtained bubble-containing liquid can also be used in the field of food.

In the above description, by performing Steps (S1) to (S5), the large amount of the bubbles 1 (see FIG. 1) having the uniform size can be stably manufactured in the manufacturing container 20. However, the method for manufacturing bubbles of the present embodiment is not limited thereto. For example, after Step (S5), Step (S4) and Step (S5) may be repeated at least once or more times. By repeating Step (S4) and Step (S5), the bubbles 1 having the uniform diameter can be more stably generated.

Second Embodiment

Next, a second embodiment of the method for manufacturing bubbles and the bubble manufacturing container of the present invention will be described.

Figure 6:
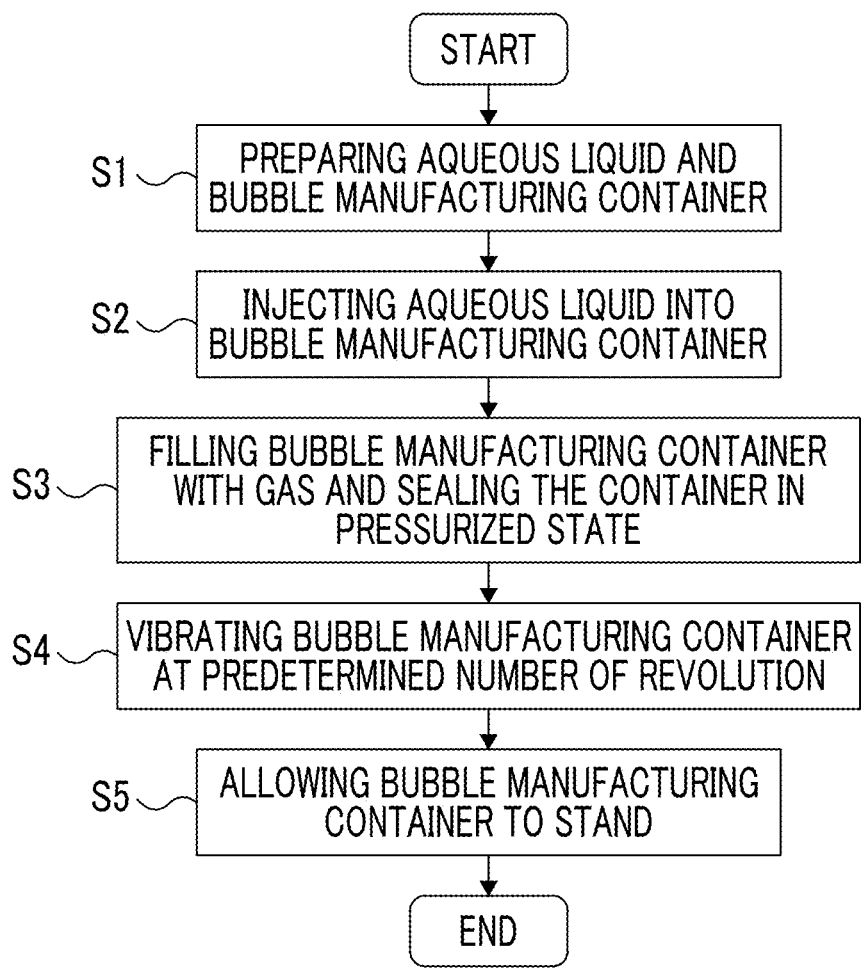
FIG. 6 is a flow chart for illustrating a second embodiment of the method for manufacturing bubbles of the present invention.

FIG. 6 is a flow chart for illustrating the second embodiment of the method for manufacturing bubbles of the present invention. FIGS. 7(a) to 7(d) are cross-sectional views for illustrating the second embodiment of the method for manufacturing bubbles of the present invention.

In the following description, the upper side in each of FIGS. 7(a) to 7(d) will be referred to as "top", and the lower side in each of FIGS. 7(a) to 7(d) will be referred to as "bottom".

Hereinafter, regarding the method for manufacturing bubbles of the second embodiment, the differences between the method for manufacturing bubbles of the first embodiment and the method for manufacturing bubbles of the present embodiment will be mainly described, and the same details will not be described.

The method for manufacturing bubbles of the present embodiment is the same as the method for manufacturing bubbles of the first embodiment described above, except that in Step (S3) of the first embodiment, the manufacturing container is sealed in a state where the interior of the manufacturing container is pressurized as shown in FIG. 6.

[S3] Step of Sealing Manufacturing Container

Figure 7:
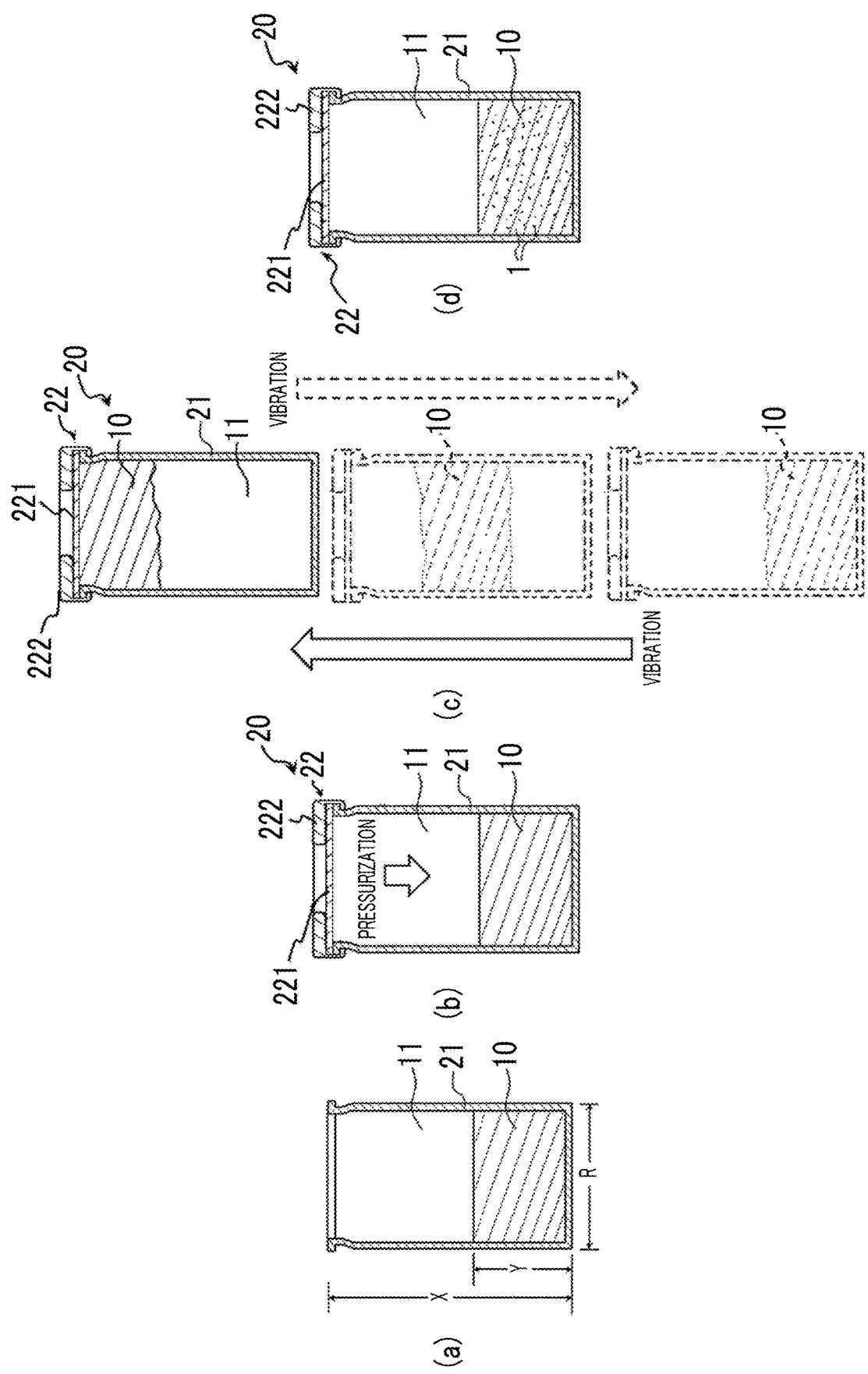
FIG. 7 shows cross-sectional views for illustrating the second embodiment of the method for manufacturing bubbles of the present invention.

In a state where the container body 21 is filled with the gas 3 such that the interior of the manufacturing container 20 is pressurized, the manufacturing container is sealed (see FIG. 7(b)). Specifically, by using the gas 3, purging is performed in the void portion 11 of the container body 21 into which the aqueous liquid 10 is injected, and then the lid 22 is fastened to the opening portion (vial mouth) of the container body 21. In this way, the aqueous liquid 10 and the gas 3 are sealed in the manufacturing container 20.

Then, a syringe filled with the gas 3 is prepared, and an injection needle of the syringe is pierced into the rubber stopper 221. Thereafter, the gas 3 is further added into the manufacturing container 20 from the syringe, thereby pressurizing the interior of the manufacturing container 20. Subsequently, the injection needle is pulled out of the rubber stopper 221. In this way, it is possible to obtain the manufacturing container 20 which is sealed in a state where the interior of the manufacturing container 20 is pressurized due to the gas 3.

In the method for manufacturing bubbles of the present embodiment, the internal pressure of the manufacturing container 20 (pressure of gas 3 with which the void portion 11 is filled) is set to be higher than 1.0 atm. Particularly, the internal pressure of the manufacturing container 20 is preferably 1.5 to 10 atm, and more preferably 2 to 5 atm. In this way, a portion of the gas 3 is micro-dispersed or dissolved in the aqueous liquid 10.

In a case where the gas 3 is micro-dispersed or dissolved in the aqueous liquid 10, when shock waves occur due to the collision between the aqueous liquid 10 and the manufacturing container 20 in Step (S4), bubbles 1 are easily generated. In this way, in Step (S4), more bubbles 1 can be generated in the aqueous liquid 10.

In a case where the internal pressure of the manufacturing container 20 is set to be a certain value higher than 1.0 atm, it is possible to more easily adjust the diameter and content of the bubbles 1 generated in the aqueous liquid 10.

In a case where Step (S4) and Step (S5) or Steps (S4) to (S6) are performed in the same manner as in the first embodiment described above by using the manufacturing container 20 in which the aqueous liquid 10 and the gas 3 are sealed as described above, a large amount of bubbles 1 having a uniform size can be stably manufactured in the manufacturing container 20. In addition, the manufacturing container 20 containing the large amount of bubbles 1 having the uniform size is obtained.

In the method for manufacturing bubbles of the present embodiment, the manufacturing container 20 in which the void portion 11 is pressurized due to the gas 3 is used. Therefore, at the stage in which the manufacturing container 20 is not yet vibrated, the gas 3 is sufficiently micro-dispersed or dissolved in the aqueous liquid 10. Accordingly, when the manufacturing container 20 is vibrated in Step (S4), the bubbles 1 can be easily generated in the aqueous liquid 10, and the large amount of bubbles 1 having the uniform size can be more easily manufactured than in the method for manufacturing bubbles of the first embodiment described above.

The interior of the bubble-containing container (manufacturing container 20) obtained in the present embodiment is pressurized. In a case where the internal pressure of the bubble-containing container is rapidly reduced, the pressure reduction is likely to exert a negative influence such as a change in the particle size of the bubbles 1 in the bubble-containing liquid or a reduction in the content of the bubbles. Therefore, when the bubble-containing liquid is aspirated from the interior of the bubble-containing container, it is preferable to reduce the internal pressure of the bubble-containing container in advance down to the atmospheric pressure.

For example, a syringe (syringe for pressure reduction), which is different from the syringe (syringe for bubble aspiration) for aspirating the bubble-containing liquid from the bubble-containing container, is prepared, and an injection needle of the syringe is pierced into the rubber stopper 221. At this time, an attention needs to be paid to prevent the injection needle of the syringe for pressure reduction from not contacting with the bubble-containing liquid. Then, the gas 3 in the bubble-containing container is aspirated by operating a plunger of the syringe for pressure reduction, thereby reducing the internal pressure of the bubble-containing container down to the atmospheric pressure. Thereafter, an injection needle of the syringe for bubble aspiration is pierced into the rubber stopper 221, and then the bubble-containing liquid is aspirated. At this time, it is preferable to make the plunger of the syringe for pressure reduction in a state of being pulled out of an external cylinder thereof. In this case, the injection needle of the syringe for pressure reduction is opened to the interior and the exterior of the bubble-containing container, and hence the air freely comes into and out of the bubble-containing container from the injection needle. With this constitution, when the bubble-containing liquid is aspirated, the internal pressure of the bubble-containing container is prevented from becoming negative, that is, the internal pressure of the bubble-containing container is kept at the atmospheric pressure, and hence the aforementioned negative influence is not exerted on the generated bubbles 1.

In a state where the internal pressure of the bubble-containing container is reduced down to the atmospheric pressure, the lid 22 may be removed, and the bubble-containing liquid may be aspirated from the interior of the bubble-containing container. In this case, because the internal pressure of the bubble-containing container has been reduced down to the atmospheric pressure, it is possible to reliably prevent the bubble-containing liquid from spurting out of the manufacturing container 20 at the moment when the lid 22 is removed.

With the method for manufacturing bubbles and the bubble manufacturing container of the second embodiment, the same operations and effects as in the method for manufacturing bubbles of the first embodiment are also obtained.

Third Embodiment

Next, a third embodiment of the method for manufacturing bubbles of the present invention will be described. The bubble 1 shown in FIG. 2(*a*) described above can be manufactured by the method for manufacturing bubbles of the present embodiment.

Hereinafter, regarding the method for manufacturing bubbles of the third embodiment, the differences between the methods for manufacturing bubbles of the first and second embodiments and the method for manufacturing bubbles of the present embodiment will be mainly described, and the same details will not be described.

In the present embodiment, the aqueous liquid 10 contains a material (outer shell material), constituting the outer shell 2 of the bubble 1, and an aqueous medium. That is, the method for manufacturing bubbles of the present embodiment is the same as the method for manufacturing bubbles of the second embodiment described above, except that the aqueous liquid 10 prepared in Step (S1) in the second embodiment contains the outer shell material in addition to the aqueous medium.

[S1] Preparation Step

In the present embodiment, the outer shell material, which constitutes the outer shell 2 of the bubble 1, and the aqueous medium are put into an aqueous liquid preparation container (hereinafter, simply referred to as "preparation container"), and the outer shell material is dissolved in the aqueous medium, thereby preparing the aqueous liquid 10. That is, the outer shell material and the aqueous medium are put into the preparation container in a predetermined amount and then stirred such that the outer shell material is dissolved in the aqueous medium. The order of putting the outer shell material and the aqueous medium into the preparation container is not particularly limited. As a method for dissolving the outer shell material in the aqueous medium, for example, stirring using a stirrer, an ultrasonic treatment, and the like can be used.

As the outer shell material, the amphipathic material described above is used. As the aqueous medium, the same aqueous medium as in the first embodiment described above can be used.

In Step (S4), a content of the outer shell material in the aqueous liquid 10 is not particularly limited as long as the bubbles 1 can be formed in the aqueous liquid 10. The preferred content of the outer shell material varies with the combination of the types of the outer shell material and the aqueous medium. It is preferable that the outer shell material is contained in the aqueous liquid 10 such that the concentration of the material becomes equal to or higher than a critical micelle concentration (CMC). Specifically, the content of the outer shell material contained in the aqueous liquid 10 is preferably 0.01 to 50 wt %, and more preferably 0.1 to 20 wt %.

In this way, the concentration of the outer shell material in the aqueous liquid 10 more reliably becomes equal to or higher than the critical micelle concentration, and hence the outer shell 2 (a liposome or a micelle) can be reliably formed in the aqueous liquid 10. Therefore, in Step (S4) which will be described later, the gas 3 is incorporated into the liposome or the micelle in a simple manner, and hence the bubbles 1 having an intended size can be easily generated in the aqueous liquid 10. Due to the existence of the outer shell 2, for a long period of time, the bubbles 1 generated in the present embodiment can prevent the gas 3 in the bubbles 1 from being eluted into the aqueous liquid 10 (aqueous medium). Consequently, the stability of the bubbles 1 is improved, and hence the accidental bursting of the bubbles 1 can be more reliably prevented. Furthermore, the variation in the size of the generated bubbles 1 can be reduced. That is, the bubbles 1 having the uniform size can be generated.

The content of the aqueous medium in the prepared aqueous liquid 10 is preferably 50 to 99.99 wt %, and more preferably 80 to 99.0 wt %. In this way, the outer shell material can be sufficiently dissolved in the aqueous medium, and hence a more homogeneous aqueous liquid 10 can be obtained.

Then, the same manufacturing container 20 as in the first and second embodiments described above is prepared.

The aforementioned preparation container and the manufacturing container 20 may be the same as or different from each other.

In a case where the preparation container and the manufacturing container 20 are different from each other, for example, a container having a relatively large volume can be used as the preparation container, and a container having a relatively small volume can be used as the manufacturing container 20 (container body 21). In this case, by preparing a large amount of aqueous liquid 10 having a uniform composition in the preparation container, and dividing the aqueous liquid 10 into a plurality of manufacturing containers 20, the size (diameter) and amount of the bubbles generated in each of the manufacturing containers 20 can be made uniform.

In a case where the preparation container and the manufacturing container 20 are the same as each other, Step (S2) can be skipped, and this is advantageous because the process can be simplified.

In the present embodiment, as the preparation container, a container different from the manufacturing container 20 is used.

Then, by performing Steps (S2) to (S5) or Steps (S2) to (S6) in the same manner as in the first embodiment described above, the large amount of bubbles 1 having the uniform size can be stably manufactured in the manufacturing container 20. In addition, the manufacturing container 20 containing the large amount of bubbles 1 having the uniform size is obtained.

In the present embodiment, due to the pressure of the shock waves that occur when the aqueous liquid 10 collides with the manufacturing container 20 in Step (S4), the gas 3 is micro-dispersed or dissolved in the aqueous liquid 10, and the outer shell material in the aqueous liquid 10 is changed to the bubble 1. The bubble 1 (outer shell 2) contains the gas 3, which is micro-dispersed or dissolved in the aqueous liquid 10 in Step (S3), and the gas 3 which is micro-dispersed or dissolved in the aqueous liquid 10 due to the vibration of this step.

In Step (S3), the interior of the manufacturing container 20 may not be pressurized (that is, the internal pressure of the manufacturing container 20 is the atmospheric pressure) in the same manner as in the first embodiment or may be pressured in the same manner as in the second embodiment.

With the method for manufacturing bubbles and the bubble manufacturing container of the third embodiment, the same operations and effects as in the methods for manufacturing bubbles of the first and second embodiments are also obtained.

Fourth Embodiment

Next, a fourth embodiment of the method for manufacturing bubbles of the present invention will be described. The bubbles 1 shown in FIGS. 2(*b*) and 2(*c*) described above can be manufactured by the method for manufacturing bubbles of the present embodiment.

Hereinafter, regarding the method for manufacturing bubbles of the fourth embodiment, the differences between the methods for manufacturing bubbles of the first to third embodiments and the method for manufacturing bubbles of the present embodiment will be mainly described, and the same details will not be described.

In the present embodiment, the aqueous liquid 10 contains an aqueous medium, an outer shell material, and a drug (medicine) 4. That is, the method for manufacturing bubbles of the present embodiment is the same as the method for manufacturing bubbles of the third embodiment described above, except that the aqueous liquid 10 prepared in Step (S1) in the third embodiment contains the drug 4 in addition to the outer shell material and the aqueous medium.

[S1] Preparation Step

In the present embodiment, the outer shell material, the drug 4, and the aqueous medium are put into the preparation container, and the outer shell material and the drug 4 are dissolved in the aqueous medium, thereby preparing the aqueous liquid 10. That is, the outer shell material, the drug 4, and the aqueous medium are put into the preparation container in a predetermined amount and then stirred, thereby dissolving the outer shell material and the drug 4 in the aqueous medium. The order of putting the outer shell material, the drug 4, and the aqueous medium into the preparation container is not particularly limited. As a method for dissolving the outer shell material and the drug 4 in the aqueous medium, for example, stirring using a stirrer, an ultrasonic treatment, and the like can be used.

As the drug 4, the gene, the drug, and the like described above are used. A content of the drug 4 contained in the prepared aqueous liquid 10 is preferably 0.1 to 50 wt %, and more preferably 20 to 50 wt %. In this way, a sufficient amount of drug 4 can be incorporated into the manufactured bubbles 1. As a result, it is possible to manufacture the bubbles 1 that are excellently effective for treating an affected site. In a case where the drug 4 constitutes the outer shell 2 instead of the outer shell material, the aqueous liquid 10 may not contain the outer shell material.

In a case where Steps (S2) to (S5) or Steps (S2) to (S6) are performed in the same manner as in the third embodiment described above by using the aqueous liquid 10 prepared as above, the large amount of the bubbles 1 (see FIGS. 2(*b*) and 2(*c*)) having the uniform size can be stably manufactured in the manufacturing container 20. In addition, the manufacturing container 20 containing the large amount of the bubbles 1 having the uniform size is obtained.

In the present embodiment, the bubble 1 (outer shell 2) contains the gas 3 which is micro-dispersed or dissolved in the aqueous liquid 10 in Step (S3), the gas 3 which is micro-dispersed or dissolved in the aqueous liquid 10 due to the vibration in Step (S4), and the drug 4.

As a result, in the generated bubble 1, the drug 4 is sealed in the outer shell 2 together with the gas 3 or incorporated into or adsorbed onto the outer shell 2 itself.

3. How to Use

The bubble-containing container obtained as above is used for ultrasound therapy provided to patients or an ultrasonic diagnosis.

Specifically, first, an injection needle of a syringe is pierced into the rubber stopper 221 of the lid 22. Then, by using the syringe, the bubble-containing liquid is aspirated from the interior of the bubble-containing container. The injection needle of the syringe into which the bubble-containing liquid is aspirated is pierced into a blood vessel (for example, a vein) of a patient, and the bubble-containing liquid is injected into the blood vessel. In this way, the bubbles 1 are transported to an affected site through the blood flow.

At the time of the ultrasound therapy, when the bubbles 1 reach the vicinity of the affected site, the bubbles are irradiated with therapeutic ultrasonic waves having a frequency and an intensity at which the outer shell 2 may burst, thereby bursting the outer shell 2. In this way, by intensively supplying (applying) the drug 4 in the bubbles 1 to the affected site, the affected site can be treated.

In this case, it is also effective to perform the ultrasound therapy and the ultrasonic diagnosis in combination. Specifically, the bubbles 1 in the blood vessel are irradiated with the ultrasonic waves for diagnosis, and the reflection waves are monitored. In this way, the position or the behavior of the bubbles 1 in the blood vessel (body) can be reliably ascertained. When the bubbles 1 reach the vicinity of the affected site of interest, the bubbles are irradiated with the therapeutic ultrasonic waves such that the bubbles 1 (outer shell 2) bursts. In this way, the affected site can be treated by more accurately supplying the drug thereto.

In a case where a component (for example, carbon dioxide) showing high solubility in the aqueous medium described above is used as the gas 3, after an elapse of a predetermined time from the manufacturing of the bubbles 1, the gas 3 in the outer shell 2 is eluted into the aqueous medium. In a case where the gas 3 in the outer shell 2 is then completely eluted into the aqueous medium, the drug 4 becomes the only component sealed in the outer shell 2. That is, in this case, the bubbles 1 become liposomes or micelles in which only the drug 4 is sealed in the outer shell 2. The liposomes or the micelles obtained in this way can be used as a medical agent.

The intensity (power) of the therapeutic ultrasonic waves is preferably about 0.1 to 30 W/cm$^2$, and more preferably about 0.5 to 10 W/cm$^2$. In a case where the intensity of the therapeutic ultrasonic waves is within the aforementioned range, it is possible to more reliably burst the bubbles 1 and to eliminate or reduce the damage of normal cells around the affected site. Furthermore, in a case where the intensity of the therapeutic ultrasonic waves is within the aforementioned range, the irradiation time is preferably about 10 to 120 seconds, and more preferably about 30 to 60 seconds.

The frequency of the ultrasonic waves radiated at the time of the ultrasound therapy is preferably about 100 kHz to 10 MHz, and more preferably about 700 kHz to 1 MHz. In a case where the frequency of the ultrasonic waves radiated is within the aforementioned range, the bubbles can be burst by the ultrasonic waves of lower power.

Even in a case where the method for manufacturing bubbles of the fourth embodiment is used, the same operations and effects as in the methods for manufacturing bubbles of the first to thirds embodiments are obtained.

Fifth Embodiment

Next, a fifth embodiment of the method for manufacturing bubbles of the present invention will be described.

Figure 8:
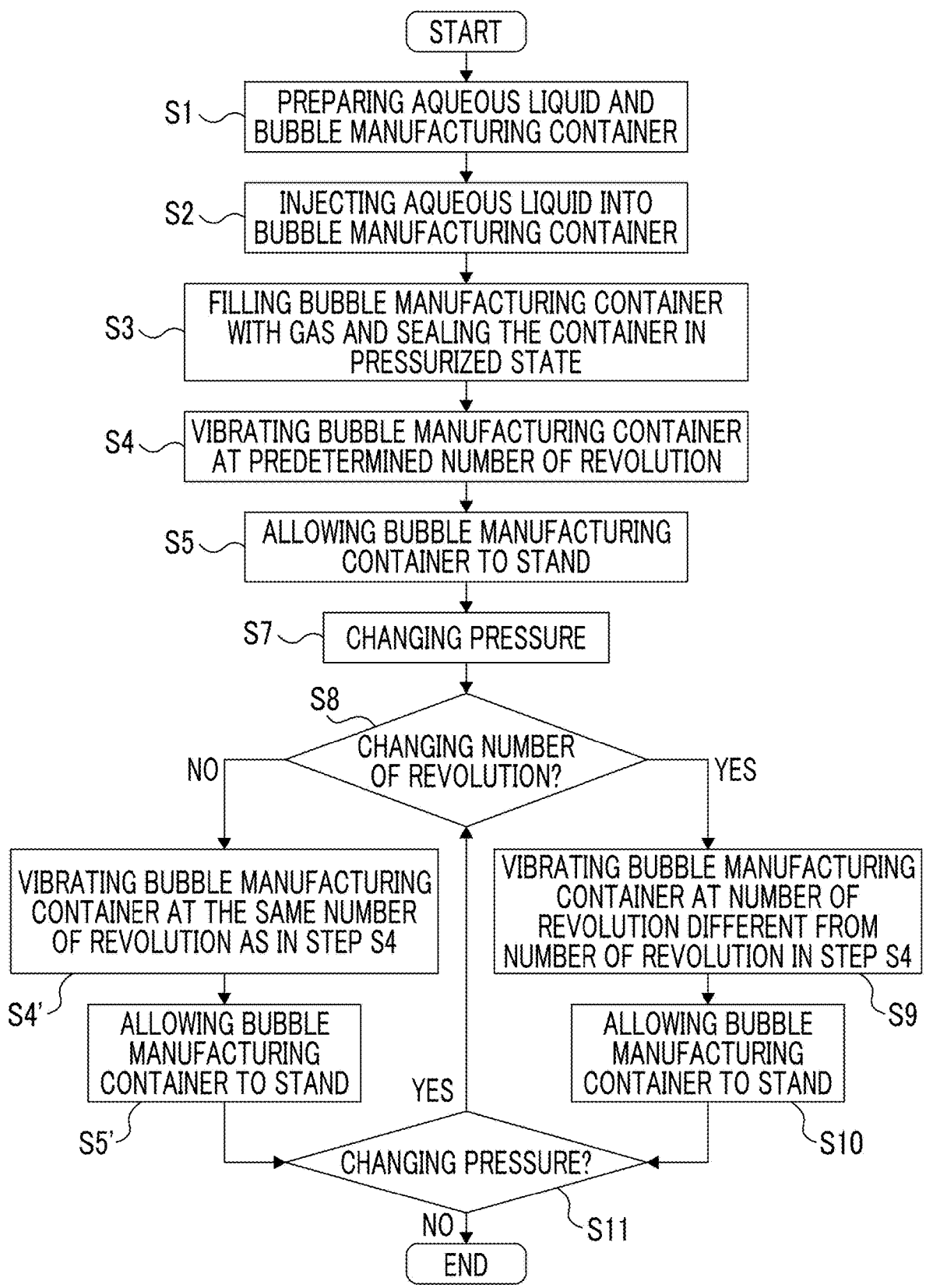
FIG. 8 is a flow chart for illustrating a fifth embodiment of the method for manufacturing bubbles of the present invention.

FIG. 8 is a flow chart for illustrating the fifth embodiment of the method for manufacturing bubbles of the present invention.

Hereinafter, regarding the method for manufacturing bubbles of the fifth embodiment, the differences between the methods for manufacturing bubbles of the first to fourth embodiments and the method for manufacturing bubbles of the present embodiment will be mainly described, and the same details will not be described.

As shown in FIG. 8, the method for manufacturing bubbles of the present embodiment includes Step (S7) and Step (S8) after Steps (S1) to (S5) (or Steps (S1) to (S6)) in the second embodiment described above. Step (S7) is a step of changing the internal pressure of the manufacturing container. Step (S8) is a step of setting the number of revolution at which the manufacturing container is vibrated.

In a case where the number of revolution is not changed in Step (S8) (in a case where "NO" is selected in Step (S8) in FIG. 8), the method for manufacturing bubbles of the present embodiment further includes Step (S4') and Step (S5'). In contrast, in a case where the number of revolution is changed in Step (S8) (in a case where "YES" is selected in Step (S8) in FIG. 8), the method for manufacturing bubbles of the present embodiment further includes Step (S9) and Step (S10). Furthermore, the method for manufacturing bubbles of the present embodiment includes Step (S11) of changing the internal pressure of the manufacturing container. Hereinafter, each step following Step (S7) will be sequentially described.

In the present embodiment, the aqueous liquid 10 may be composed only of the aqueous medium as in the first and second embodiments, may be composed only of the aqueous medium and the outer shell material as in the third embodiment, or may contain the aqueous medium, the outer shell material, and the drug 4 as in the fourth embodiment.

[S7] Step of Changing Internal Pressure of Manufacturing Container

The internal pressure of the bubble-containing container (manufacturing container 20) having undergone Step (S5) in the first embodiment described above is changed.

(1) Case Where Internal Pressure of Manufacturing Container is Made Higher than Pressure in Step (S3)

The interior of the manufacturing container 20 is pressurized in the same manner as in the aforementioned Step (S3). The gas 3 to be injected may be the same as or different from the gas 3 used in Step (S3). However, from the viewpoint of the stability of the finally generated bubbles 1, it is preferable to use the same gas 3.

In such a manufacturing container 20, the interior of the manufacturing container 20 is additionally pressurized by the internal pressure of the manufacturing container 20 in Step (S3). Therefore, the amount of the gas 3 which is micro-dispersed or dissolved in the aqueous liquid 10 becomes larger than the amount of the gas 3 which is micro-dispersed or dissolved in the aqueous liquid 10 in Step (S3). Consequently, when the manufacturing container 20 is vibrated again in Step (S4') or Step (S9) which will be described later, the gas 3 in the aqueous liquid 10 is easily incorporated into the generated bubbles 1, and as a result, the amount of the generated bubbles 1 increases. Furthermore, a pressure higher than the pressure applied to the bubbles 1 generated in Step (S4) is applied to the aqueous liquid 10. As a result, the bubbles 1 in the process generation are compressed under a higher pressure, and hence the diameter of the bubble 1 is easily reduced. Accordingly, it is possible to generate the bubbles 1 having a diameter smaller than that of the bubbles 1 generated in Step (S4).

In this case, the internal pressure of the manufacturing container 20 is higher than the pressure in Step (S3) preferably by 0.5 atm or more, and more preferably by 1 to 10 atm. In this way, it is possible to more reliably generate the bubbles 1 having a diameter smaller than that of the bubbles 1 generated in Step (S4) described above.

(2) Case Where Internal Pressure of Manufacturing Container is Made Higher than 1.0 ATM but Lower than Pressure in Step (S3)

First, an empty syringe is prepared, and then an injection needle of the syringe is pierced into the rubber stopper 221. Thereafter, the gas 3 in the manufacturing container 20 is aspirated into the syringe. In this way, the internal pressure of the manufacturing container 20 is reduced. Then, the injection needle is pulled out of the rubber stopper 221.

In the manufacturing container 20, when the manufacturing container 20 is vibrated again in Step (S4') or Step (S9) which will be described later, the pressure applied to the aqueous liquid 10 is lower than the pressure applied to the aqueous liquid 10 generated in Step (S4). As a result, the bubbles 1 in the process of generation are compressed less, and hence the size of the bubbles 1 easily increases. Therefore, it is possible to generate the bubbles 1 having a diameter larger than that of the bubbles 1 generated in Step (S4).

In this case, the internal pressure of the manufacturing container 20 is appropriately adjusted within such a range that the internal pressure becomes higher than 1.0 atm but is lower than the pressure in Step (S3).

[S8] Step of setting number of revolution at which manufacturing container is vibrated After the internal pressure of the manufacturing container 20 is changed as described above, the number of revolution at which the container is vibrated again is set.

As in Step (S4) described above, the number of revolution at the time of vibrating again the container is set to be equal to or higher than 5,000 rpm.

In Step (S8), in a case where the number of revolution at the time of vibrating again the container is not changed from the number of revolution in Step (S4), that is, in a case where "NO" is selected in Step (S8) in FIG. 8, the following Step (S4') is performed.

On the other hand, in Step (S8), in a case where the number of revolution at the time of vibrating again the container is changed from the number of revolution in Step (S4), that is, in a case where "YES" is selected in Step (S8) in FIG. 8, the following Step (S9) is performed.

[S4'] Step of Vibrating Again Manufacturing Container

In the manner described above, the manufacturing container 20 whose internal pressure is changed is vibrated again at the same number of revolution as in Step (S4) described above. In this way, the bubbles 1 having a diameter different from that of the bubbles 1 generated in Step (S4) are generated in the aqueous liquid 10.

In this step, the manufacturing container 20 is vibrated again at the same number of revolution as in Step (S4). Therefore, the diameter of the bubbles 1 newly generated in the present embodiment changes according to the pressure changed in Step (S7). That is, by changing the pressure, the diameter of the bubbles 1 can be adjusted, and hence the bubbles 1 having different intended diameters (average diameters) can be manufactured with excellent reproducibility. Furthermore, because the setting of a device vibrating the manufacturing container 20 does not need to be changed, the bubbles 1 having the different diameters can be manufactured in a simpler manner.

[S5'] Step of Allowing Manufacturing Container to Stand

After the manufacturing container 20 is vibrated under the aforementioned condition, the manufacturing container 20 is allowed to stand in the same manner as in Step (S5). In this way, the large amount of bubbles 1 having the different sizes can be stably manufactured in the manufacturing container 20. In addition, the manufacturing container 20 (bubble-containing container) containing the large amount of bubbles 1 described above is obtained.

After the container is allowed to stand, Step (S11) is performed.

[S9] Step of Vibrating Again Manufacturing Container

The manufacturing container 20 whose internal pressure is changed is vibrated again at the number of revolution different from that in Step (S4) described above. In this way, the bubbles 1 having a diameter different from that of the bubbles 1 generated in Step (S4) are generated in the aqueous liquid 10.

(1) Case Where Manufacturing Container is Vibrated Again at Number of Revolution Higher than that in Step (S4)

The manufacturing container 20 is vibrated again in the same manner as in Step (S4) described above, except that the number of revolution at which the manufacturing container 20 is vibrated is made higher than the number of revolution in Step (S4).

In this case, the number of revolution of the manufacturing container 20 is not particularly limited as long as it is higher than the number of revolution in Step (S4). The number of revolution in this case is preferably 6,000 to 20,000 rpm, and more preferably 7,000 to 20,000 rpm. In this way, because the manufacturing container 20 is vibrated at the number of revolution higher than that in Step (S4), it is possible to generate the bubbles 1 having a diameter smaller than that of the bubbles 1 generated in Step (S4). Furthermore, by setting the number of revolution of the manufacturing container 20 within the aforementioned range, it is possible to more reliably prevent the bubbles 1 generated in Step (S4) and the present step from being destroyed due to collision or from coarsening by being combined with each other. As a result, it is possible to manufacture the bubbles 1 generated in Step (S4) and the bubbles 1 having a diameter smaller than that of the bubbles 1 generated in Step (S4).

(2) Case Where Manufacturing Container is Vibrated Again at Number of Revolution Lower than that in Step (S4)

The manufacturing container 20 is vibrated again in the same manner as in Step (S4), except that the number of revolution at which the manufacturing container 20 is vibrated is made lower than that in Step (S4).

In this case, the number of revolution of the manufacturing container 20 is not particularly limited as long as it is lower than the number of revolution in Step (S4). The number of revolution in this case is preferably 5,000 to 9,000 rpm, and more preferably 5,500 to 7,500 rpm. In this way, the manufacturing container 20 is vibrated at the number of revolution lower than that in Step (S4), and hence the bubbles 1 having a diameter larger than that of the bubbles 1 generated in Step (S4) can be generated. Furthermore, by setting the number of revolution of the manufacturing container 20 to be within the aforementioned range, it is possible to more reliably prevent the bubbles 1 generated in Step (S4) and the present step from being destroyed due to the collision or from coarsening by being combined with each other. As a result, it is possible to manufacture the bubbles 1 generated in Step (S4) and the bubbles 1 having a diameter larger than that of the bubbles 1 generated in Step (S4).

In this step, the manufacturing container 20 is vibrated again at the number of revolution different from that in Step (S4). Therefore, the diameter of the bubbles 1 newly generated in the present embodiment changes according to the change of the internal pressure of the manufacturing container 20 and to the number of revolution at the time of vibrating again the container. In this way, by changing both the internal pressure of the manufacturing container 20 and the number of revolution at the time of vibrating again the container, it is possible to generate the bubbles 1 having a diameter greatly different from the diameter obtained in the first embodiment described above. Accordingly, in a case where the bubbles 1 that greatly differ from each other in terms of the average diameter are manufactured, the present step is advantageous.

[S10] Step of Allowing Manufacturing Container to Stand

After the manufacturing container 20 is vibrated in Step (S9), the manufacturing container 20 is allowed to stand in the same manner as in Step (S5). In this way, the bubbles 1 having the different diameters can be stably manufactured in the manufacturing container 20. In addition, the manufacturing container 20 (bubble-containing container) containing the large amount of bubbles 1 described above is obtained.

After the container is allowed to stand, Step (S11) is performed.

[S11] Step of Changing Again Internal Pressure of Manufacturing Container

In a case where the internal pressure of the manufacturing container 20 is not changed, that is, in a case where "NO" is selected in Step (S11) in FIG. 8, the method for manufacturing bubbles of the present embodiment is finished. In this way, first bubbles 1 and second bubbles 1 having different average diameters within a range of 10 nm to 1,000 μm are manufactured.

In contrast, in a case where the internal pressure of the manufacturing container 20 is changed, that is, in a case where "YES" is selected in Step (S11) in FIG. 8, Step (S8) is performed. Then, Steps (S4'), (S5'), and (S11) described above or Steps (S9), (S10), and (S11) are repeated. In this way, it is possible to manufacture the bubbles 1 having a plurality of different average diameters within a range of 10 nm to 1,000 μm.

In a case where the pressure is repeatedly changed in Step (S11), it is possible to manufacture the bubbles 1 having the plurality of different average diameters according to the number of times the pressure is changed.

The bubble-containing container obtained as above contains the bubbles 1 having the different diameters in the aqueous liquid 10. The ease of passing the bubbles 1 in blood vessels and the site to which the bubbles are transported vary with the difference in the size (for example, the smaller the size of the bubbles 1 is, the farther the bubbles 1 can be transported toward the end of a capillary). Therefore, the bubble-containing liquid obtained as above can be used in many ways according to the purpose of the ultrasound therapy.

With the method for manufacturing bubbles of the fifth embodiment, the same operations and effects as in the methods for manufacturing bubbles of the first to fourth embodiments are also obtained.

Sixth Embodiment

Next, a sixth embodiment of the method for manufacturing bubbles of the present invention will be described.

Figure 9:
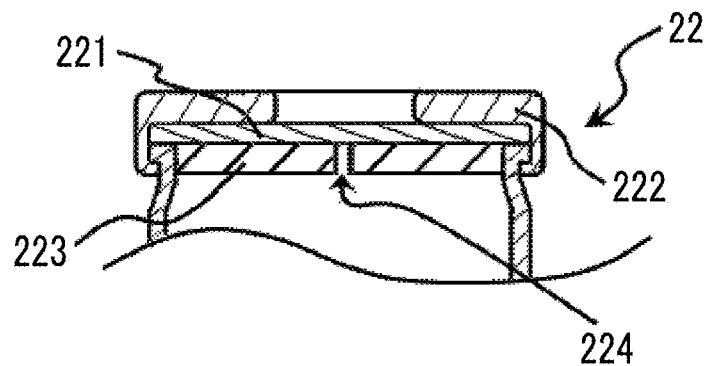
FIG. 9 is a partial cross-sectional view showing the vicinity of a lid of a manufacturing container used in a sixth embodiment of the method for manufacturing bubbles of the present invention.

FIG. 9 is a partial cross-sectional view showing the vicinity of a lid of a manufacturing container used in the sixth embodiment of the method for manufacturing bubbles of the present invention.

In the following description, the upper side in FIG. 9 will be referred to as "top", and the lower side in FIG. 9 will be referred to as "bottom".

Hereinafter, regarding the method for manufacturing bubbles of the sixth embodiment, the differences between the methods for manufacturing bubbles of the first to fifth embodiments and the method for manufacturing bubbles of the present embodiment will be mainly described, and the same details will not be described.

The method for manufacturing bubbles of the present embodiment is the same as the methods for manufacturing bubbles of the first to fifth embodiments described above, except that the constitution of the lid 22 of the manufacturing container 20 (the second embodiment of the bubble manufacturing container) is different.

The lid 22 shown in FIG. 9 includes, in addition to the rubber stopper 221 and the fastening portion 222 described above, a bottom plate portion 223 which adheres to the bottom surface of the rubber stopper 221 through an adhesive or the like. In other words, the bottom plate portion 223 is provided in the opening portion of the container body 21 in a state of adhering to the rubber stopper 221. Because the manufacturing container 20 of the present embodiment includes the bottom plate portion 223, the mass of the lid 22 of the present embodiment becomes larger than that of the lid 22 of the manufacturing container 20 of the first embodiment described above. That is, the bottom plate portion 22 becomes a weight portion that increases the mass of the manufacturing container 20.

The bottom plate portion 223 is a disk-like member having a diameter smaller than that of the rubber stopper 221. Furthermore, when seen in a plan view, a through hole 224, into which an injection needle of a syringe is inserted, is formed approximately at the center of the bottom plate portion 223 so as to correspond to the opening of the fastening portion 222. The size of the through hole 224 is not particularly limited. In a case where the through hole 224 has the same size as the rubber stopper 221 exposed from the fastening portion 222, in Step (S3), the injection needle can be pierced into anywhere within a region of the rubber stopper 221 exposed from the fastening portion 222. Furthermore, as shown in FIG. 9, the through hole 224 may have a size that enables the injection needle to be inserted thereinto. In this case, a mark (not shown in the drawing) may be made on the top surface of the rubber stopper 221 in a position corresponding to the through hole 224, and the injection needle may be pierced into the rubber stopper 221 in the marked position.

The bottom plate portion 223 may be provided with a plurality of through holes 224. For example, the bottom plate portion 223 may be provided with two through holes 224 including a through hole into which an injection needle of a syringe filled with the gas 3 and an injection needle of the aforementioned pressure reduction syringe are inserted and a through hole into which an injection needle of a bubble aspirating syringe is inserted. In this constitution, by using the pressure reduction syringe, in a state where the internal pressure of the bubble-containing container is set to be atmospheric pressure, the bubbles 1 can be aspirated into the bubble aspirating syringe. Therefore, it is possible to more reliably prevent the occurrence of negative influences such as the change in the particle size of the bubbles 1 in the aspirated bubble-containing liquid or the reduction of the content. Furthermore, the bottom plate portion 223 may be provided with three through holes 224 into which the injection needle of each of the syringes is inserted. In addition, on the top surface of the rubber stopper 221, a mark at which the injection needle of each of the syringes is pierced may be made in a position corresponding to each through hole 224.

Examples of a material constituting the bottom plate portion 223 include various ceramic materials and metal materials. Among these, the material having a density (equal to or higher than 2,000 kg/m$^3$) equal to or higher than the density of glass is preferable. Examples of such a material include stainless steel such as cast iron (density: about 7,000 to 7,700 kg/m$^3$), 18/8 chromium nickel steel (density: about 7,900 kg/m$^3$), and V2A steel (density: about 7,900 kg/m$^3$), aluminum (density: about 2,700 kg/m$^3$), duralumin (density: about 2,700 kg/m$^3$), lead (density: about 11,340 kg/m$^3$), iron (density: about 7,870 kg/m$^3$), copper (density: about 8,900 kg/m$^3$), brass (density: about 8,250 to 8,500 kg/m$^3$), nickel (density: about 8,350 kg/m$^3$), cast iron (density: about 7,000 to 7,700 kg/m$^3$), zinc (density: about 7,130 kg/m$^3$), tin (density: about 7,280 kg/m$^3$), and the like. Among these, one kind of material can be used singly, or two or more kinds of materials may be used in combination. Among these materials, iron or an iron alloy such as stainless steel is particularly preferably used, because these materials have high specific gravity and exhibit high corrosion resistance with respect to the components constituting the aqueous liquid 10.

The mass of the bottom plate portion 223 constituted with the aforementioned material is greater than the mass of a member formed of a material having low specific gravity (density) such as synthetic rubber or a resin. By increasing the mass of the bottom plate portion 223, in Step (S4), it is possible to further increase the magnitude of the shock waves which occur when the aqueous liquid 10 collies with the top surface (bottom plate portion 223) of the manufacturing container 20. As a result, fine bubbles 1 can be more easily and stably generated in the aqueous liquid 10.

In a case where the lid 22 is used, in Step (S3), the injection needle of the syringe filled with the gas 3 is pierced into the rubber stopper 221 such that the needle is inserted into the through hole 224 of the bottom plate portion 223. Then, by further adding the gas 3 into the manufacturing container 20 from the syringe in the same manner as in the second embodiment described above, the interior of the manufacturing container 20 is pressurized. Thereafter, by pulling the injection needle out of the lid 22 (rubber stopper 221), it is possible to obtain the manufacturing container 20 sealed in a state where the interior of the manufacturing container 20 is pressurized due to the gas 3.

By using the manufacturing container 20 (a bubble manufacturing container of the present embodiment) constituted as above, a bubble-containing container can be obtained through the same steps as in the method for manufacturing bubbles of the first to fifth embodiments described above.

With the method for manufacturing bubbles of the sixth embodiment, the same operations and effects as in the methods for manufacturing bubbles of the first to fifth embodiments are also obtained.

Seventh Embodiment

Next, a seventh embodiment of the method for manufacturing bubbles of the present invention will be described.

FIGS. 10(a) to 10(f) are cross-sectional views schematically showing containers used in the seventh embodiment of the method for manufacturing bubbles of the present invention.

In the following description, the upper side in each of FIGS. 10(a) to 10(f) will be referred to as "top", and the lower side in each of FIGS. 10(a) to 10(f) will be referred to as "bottom".

Hereinafter, regarding the method for manufacturing bubbles of the seventh embodiment, the differences between the methods for manufacturing bubbles of the first to sixth embodiments and the method for manufacturing bubbles of the present embodiment will be mainly described, and the same details will not be described.

The method for manufacturing bubbles of the present embodiment is the same as the methods for manufacturing bubbles of the first to sixth embodiments described above, except that the container (manufacturing container) has a different shape.

In the present embodiment, the manufacturing container 20 (the third embodiment of the bubble manufacturing container) includes the container body 21 having various shapes shown in FIGS. 10(a) to 10(d) and a lid (not shown in the drawings) matching with the shape of the top surface of each container body 21. As shown in FIGS. 10(a) to 10(d), the inner surface of the container body 21 includes at least one of a convex surface, a concave surface, and a corrugated surface.

Figure 10:
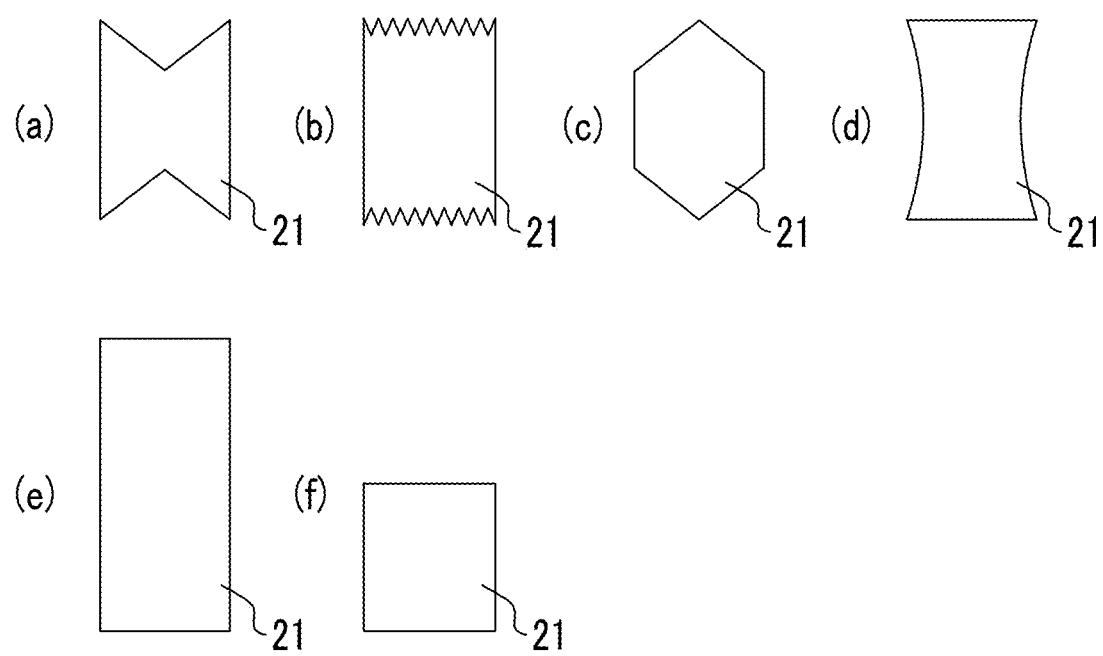
FIG. 10 shows cross-sectional views schematically showing containers used in a seventh embodiment of the method for manufacturing bubbles of the present invention.

The container body 21 shown in FIG. 10(a) is a container in which the top and bottom surfaces thereof are in the form of the convex surface projected toward the inside. The manufacturing container 20 shown in FIG. 10(b) is a container in which the top and bottom surfaces thereof are in the form of the corrugated surface. The manufacturing container 20 shown in FIG. 10(c) is a container in which the top and bottom surfaces thereof are in the form of the concave surface projected toward the outside. The manufacturing container shown in FIG. 10(d) is a container in which the lateral surface thereof is in the form of the convex surface curving toward the inside of the manufacturing container 20.

These surfaces (the concave surface, the convex surface, and the corrugated surface) have a large surface area compared to a flat surface. Therefore, in Step (S4) described above, the area in which the aqueous liquid 10 can collide with the inner surface of the manufacturing container increases, and hence more shock waves can occur. Furthermore, the magnitude of the pressure of the occurring shock waves varies with the shape of such surfaces. As a result, a large amount of bubbles 1 having different diameters can be generated in the aqueous liquid 10.

As shown in FIG. 10(e), the height of the container body 21 can be made greater than the height of the container body 21 of the first to sixth embodiments described above. In a case where such a container body 21 is used, when the manufacturing container is vibrated in Steps (S4), (S4'), and (S9), the aqueous liquid 10 moves a long distance, and hence the magnitude of the shock waves that occur at the time of collision can be increased. As a result, the size of the bubbles 1 manufactured in the aqueous liquid 10 can be further reduced.

In contrast, as shown in FIG. 10(f), the height of the container body 21 can be made smaller than the height of the container body 21 of the first to sixth embodiments described above. In a case where such a container body 21 is used, when the manufacturing container is vibrated in Steps (S4), (S4'), and (S9), the aqueous liquid 10 moves a short distance, and hence the number of times the aqueous liquid 10 collides with the inner surface of the manufacturing container can be increased. Therefore, the pressure, resulting from the shock waves and applied to the aqueous liquid 10, can be further increased. As a result, more bubbles 1 can be manufactured in the aqueous liquid 10.

With the method for manufacturing bubbles of the seventh embodiment, the same operations and effects as in the methods for manufacturing bubbles of the first to sixth embodiments are also obtained.

Eighth Embodiment

Next, an eighth embodiment of the method for manufacturing bubbles of the present invention will be described.

Figure 11:
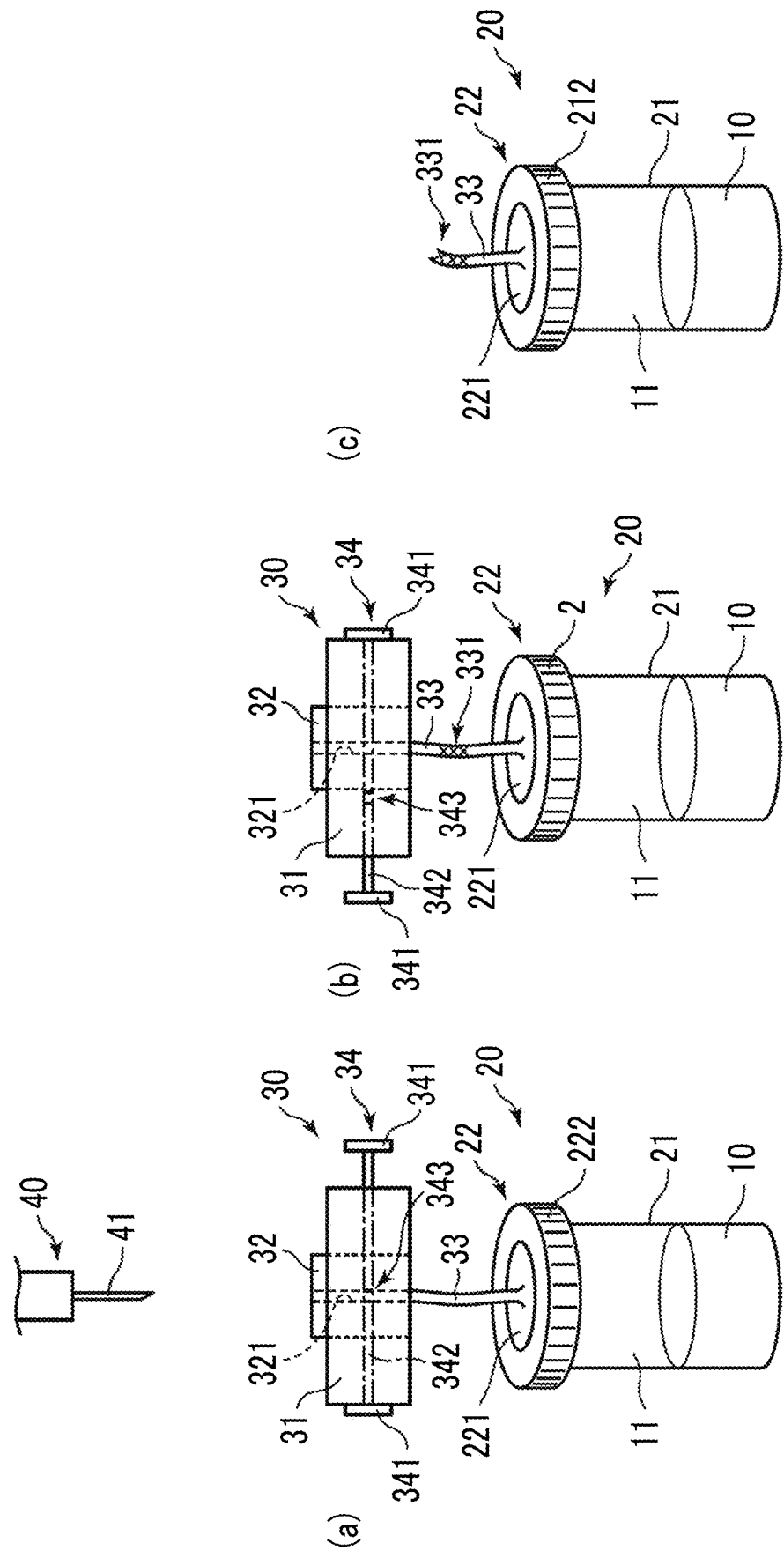
FIG. 11 shows perspective views for illustrating an eighth embodiment of the method for manufacturing bubbles of the present invention.
Figure 12:
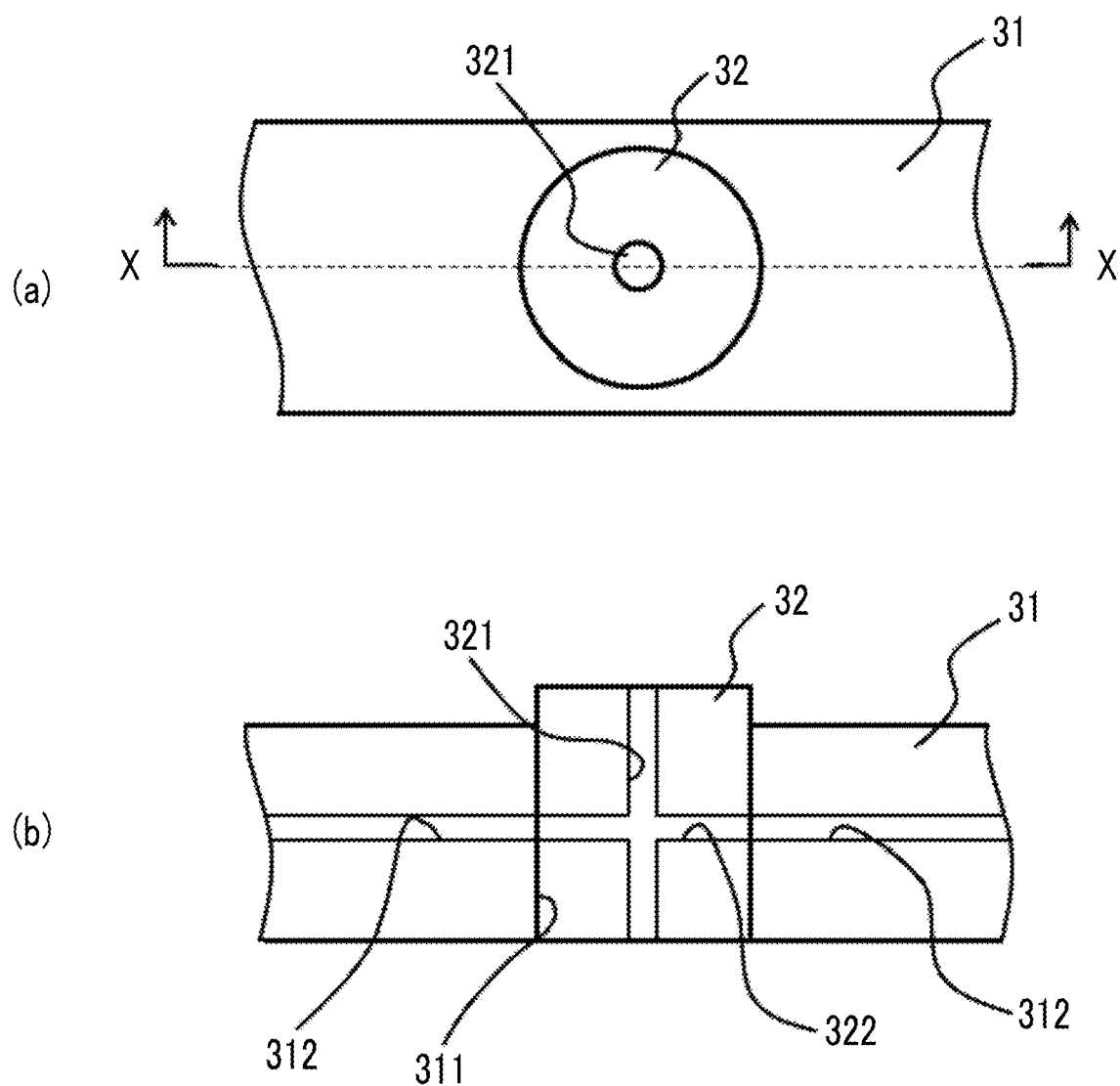
FIG. 12 shows views for illustrating the constitution (a handle is now shown) of the vicinity of a rubber stopper of a Mininert valve shown in FIG. 11(a).
Figure 13:
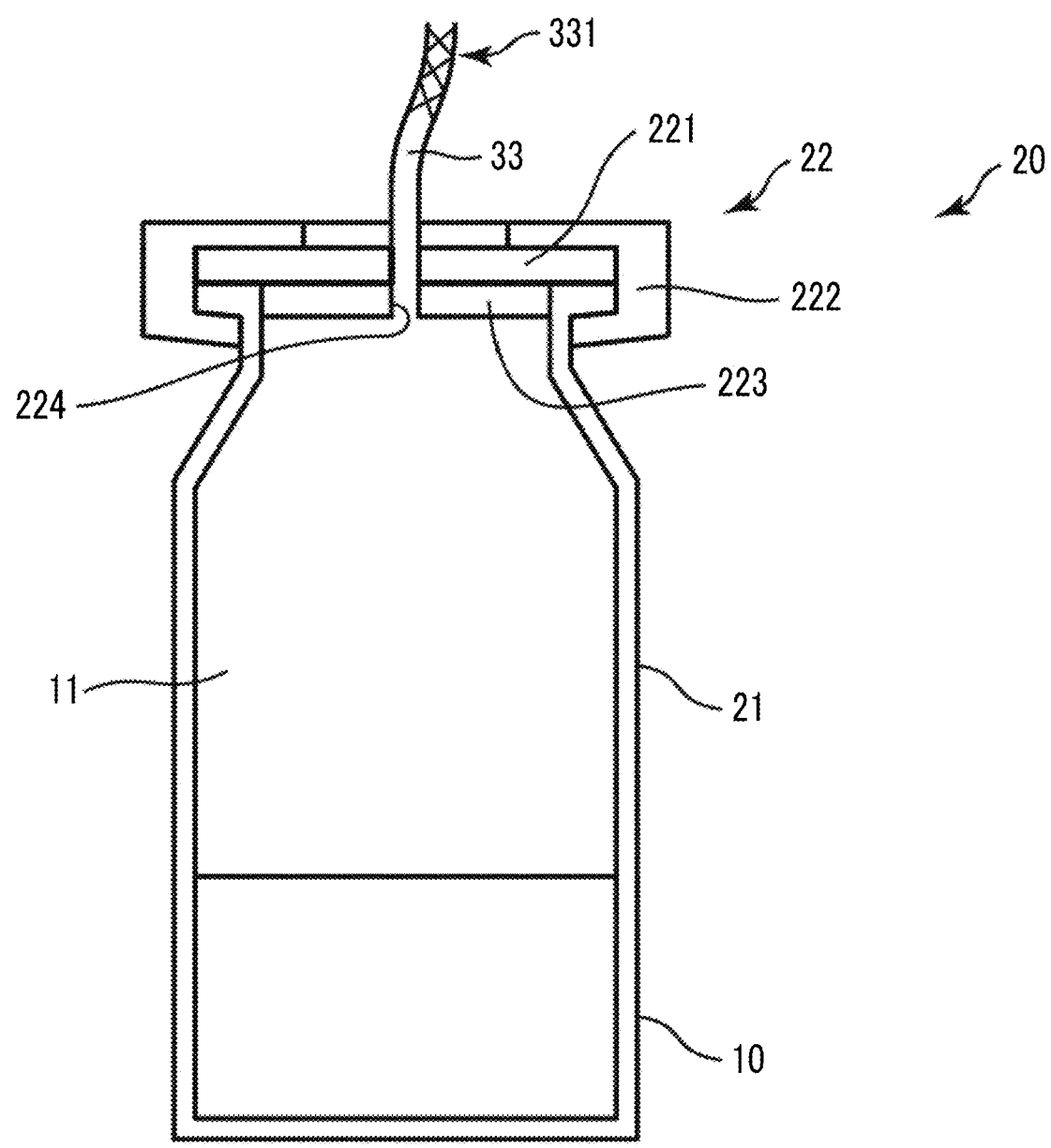
FIG. 13 is a cross-sectional view of a bubble-containing container shown in FIG. 11(c).

FIGS. 11(a) to (c) are perspective views for illustrating the eighth embodiment of the method for manufacturing bubbles of the present invention. FIG. 12 shows views for illustrating the constitution of the vicinity of a rubber stopper of a Mininert valve shown in FIG. 11(a) (a handle is not shown). FIG. 12(a) is a top view of the vicinity of the rubber stopper of the Mininert valve. FIG. 12(b) is a cross-sectional view of FIG. 12(a) taken along the line X-X. FIG. 13 is a cross-sectional view of a bubble-containing container shown in FIG. 11(c).

In the following description, the upper side in each of FIGS. 11(a) to 11(c), FIG. 12(b), and FIG. 13 as well as the front side in FIG. 12(a) based on the paper surface will be referred to as "top", and the lower side in each of FIGS. 11(a) to (c), FIG. 12(b), and FIG. 13 as well as the back side in FIG. 12(a) based on the paper surface will be referred to as "bottom". Furthermore, the left side in each of FIGS. 11(a) to 11(c) will be referred to as "left", and the right side in each of FIGS. 11(a) to 11(c) will be referred to as "right".

Hereinafter, regarding the method for manufacturing bubbles of the eighth embodiment, the differences between the methods for manufacturing bubbles of the first to seventh embodiments and the method for manufacturing bubbles of the present embodiment will be mainly described, and the same details will not be described.

The method for manufacturing bubbles of the present embodiment is the same as the methods for manufacturing bubbles of the first to fifth embodiments described above, except that the manufacturing container has a different constitution.

[S1] Preparation Step

The manufacturing container 20 (the fourth embodiment of the bubble manufacturing container) shown in FIG. 11(a) is prepared.

In the present embodiment, the manufacturing container 20 includes the container body 21 and the lid 22, similarly to the manufacturing container 20 of the first embodiment described above. As shown in FIG. 11(a), the lid 22 includes a Mininert valve 30 on the upper side thereof and a tube 33 connecting the rubber stopper 221 to the Mininert valve 30.

The Mininert valve 30 includes a valve body 31 having a through hole 311, a rubber stopper 32 in which a duct 321, being buried in the through hole 311 and penetrating the valve body 31 in a thickness direction (vertical direction), is formed, and a handle (an opening and closing mechanism) 34 which controls the opening and closing of the duct 321.

The valve body 31 has approximately a cuboid shape. In the vicinity of the center of the valve body 31 in the longitudinal direction thereof, the through hole 311 that penetrates the valve body 31 in the thickness direction (vertical direction) is formed (see FIGS. 12(a) and 12(b)). Furthermore, as shown in FIG. 12(b), in the valve body 31, a through hole 312 that penetrates the valve body 31 in the longitudinal direction thereof is formed.

The rubber stopper 32 has approximately a cylindrical shape, and is constituted with, for example, silicon rubber. The rubber stopper 32 is inserted into the through hole 311 of the valve body 31 and fixed to (buried in) the valve body 31. Approximately at the center of the rubber stopper 32, the duct 321 is formed into which an injection needle 41 of a syringe 40 can be inserted. Furthermore, in the rubber stopper 32, a through hole 322 is formed which is orthogonal to the duct 321 and penetrates the rubber stopper 32 in a width direction (horizontal direction) thereof (see FIG. 12(b)). The through hole 322 of the rubber stopper 32 and the through hole 312 of the valve body 31 are in communication with each other, and a shaft 342 of a handle 34, which will be described later, are slidably inserted into the through hole 322 and the through hole 312.

The handle 34 includes a pair of knobs 341 which is provided at both end sides of the valve body 31 in the longitudinal direction (horizontal direction) thereof, and a shaft 342 which is connected to each of the knobs 341 and slidably inserted into the through hole 322 of the rubber stopper 32 and the through hole 312 of the valve body 31. In a portion of the shaft 342, a through hole 343 penetrating the portion in the thickness direction (vertical direction in FIG. 11(a)) is formed.

The tube 33 is not particularly limited, and constituted with, for example, a tube made of silicon. The top end portion of the tube 33 is in communication with the duct 321 of the rubber stopper 32, and the bottom end portion of the tube 33 is in communication with the interior space (void portion 11) of the container body 21 through the rubber stopper 221. In other words, the duct 321 and the interior space of the container body 21 are in communication with each other through the tube 33.

In the manufacturing container 20 of the present embodiment, as shown in FIG. 11(a), the knob 341 on the left side is pushed to the right side such that the knob 341 on the left side contacts a left end portion of the valve body 31. In this way, when seen in a plan view (top view), a through hole 343 of the shaft 342 is superposed on (in communication with) the duct 321. As a result, the duct 321 is opened, and hence the duct 321, the tube 33, and the interior space of the container body 21 become in communication with each other (see FIGS. 11(a) and 12(b)). In contrast, as shown in FIG. 11(b), the knob 341 on the right side is pushed to the left such that the knob 341 on the right side contacts a right end portion of the valve body 31. In this way, when seen in the plan view (top view), a position of the through hole 343 of the shaft 342 deviates from a position of the duct 321. As a result, the duct 321 is closed, and the interior of the manufacturing container 20 is sealed.

In the present embodiment, similarly to the lid 22 shown in FIG. 9, the lid 22 includes the rubber stopper 221, the fastening portion 222, and the bottom plate portion 223 (see FIG. 13). As shown in FIG. 13, a bottom end portion (end portion on the side connected to the rubber stopper 221) of the tube 33 is disposed in a position corresponding to the through hole 224 of the bottom plate portion 223. Therefore, the tube 33 is in communication with the interior of the container body 21.

[S3] Step of Sealing Manufacturing Container

By using the gas 3, purging is performed in the void portion 11 of the container body 21 into which the aqueous liquid 10 is injected, and then the lid 22 is inserted into the opening portion (vial mouth) of the container body 21. As a result, the aqueous liquid 10 and the gas 3 are sealed in the manufacturing container 20.

Then, the syringe 40 filled with the gas 3 is prepared. As shown in FIG. 11(a), the knob 341 on the left side of the handle 34 is pushed to the right side, such that the duct 321 is opened and becomes in communication with the tube 33. Thereafter, the injection needle 41 of the syringe 40 is inserted into the duct 321, and then through the Mininert valve 30 and the tube 33, the gas 3 is further added into the manufacturing container 20 from the syringe 40. In this way, the interior of the manufacturing container 20 is pressurized.

Thereafter, the injection needle 41 is pulled out of the duct 321, and the knob 341 on the right side of the handle 34 is pushed to the left side such that the duct 321 is closed, and in this way, the duct 321 and the tube 33 are not in communication with each other.

Then, a thermal treatment is performed on a portion of the tube 33, thereby forming a sealing portion 331 in which the interior space of the tube 33 is closed (see FIG. 11(b)).

Subsequently, by cutting the tube 33 at the Mininert valve 30 side (upper side in the drawing) of the sealing portion 331, the manufacturing container 20 can be obtained which is sealed in a state where the interior of the manufacturing container 20 is pressurized due to the gas 3 (see FIG. 11(c)).

By performing the following steps in the same manner as in the first to fifth embodiments described above, a large amount of bubbles 1 having a uniform size can be stably manufactured in the manufacturing container 20. In addition, the manufacturing container (sealed container) 20 (bubble-containing container) containing the large amount of bubbles 1 having the uniform size is obtained.

In the present embodiment, in Step (S3), the interior of the manufacturing container 20 can be pressurized without directly piercing the injection needle 41 into the rubber stopper 221 of the lid 22. That is, in the present embodiment, because there is no through hole in the lid 22 and the tube 33 (the region from the rubber stopper 221 to the sealing portion 331), the sealing property of the interior of the manufacturing container 20 can be improved. By improving the sealing property of the interior of the manufacturing container 20, in the finally obtained bubble-containing container, the bubbles 1 can more stably exist in the aqueous liquid 10. That is, the long-term storability of the bubble-containing container is further improved.

With the method for manufacturing bubbles of the eighth embodiment, the same operations and effects as in the methods for manufacturing bubbles of the first to seventh embodiments are also obtained.

Ninth Embodiment

Next, a ninth embodiment of the method for manufacturing bubbles of the present invention will be described.

Figure 14:
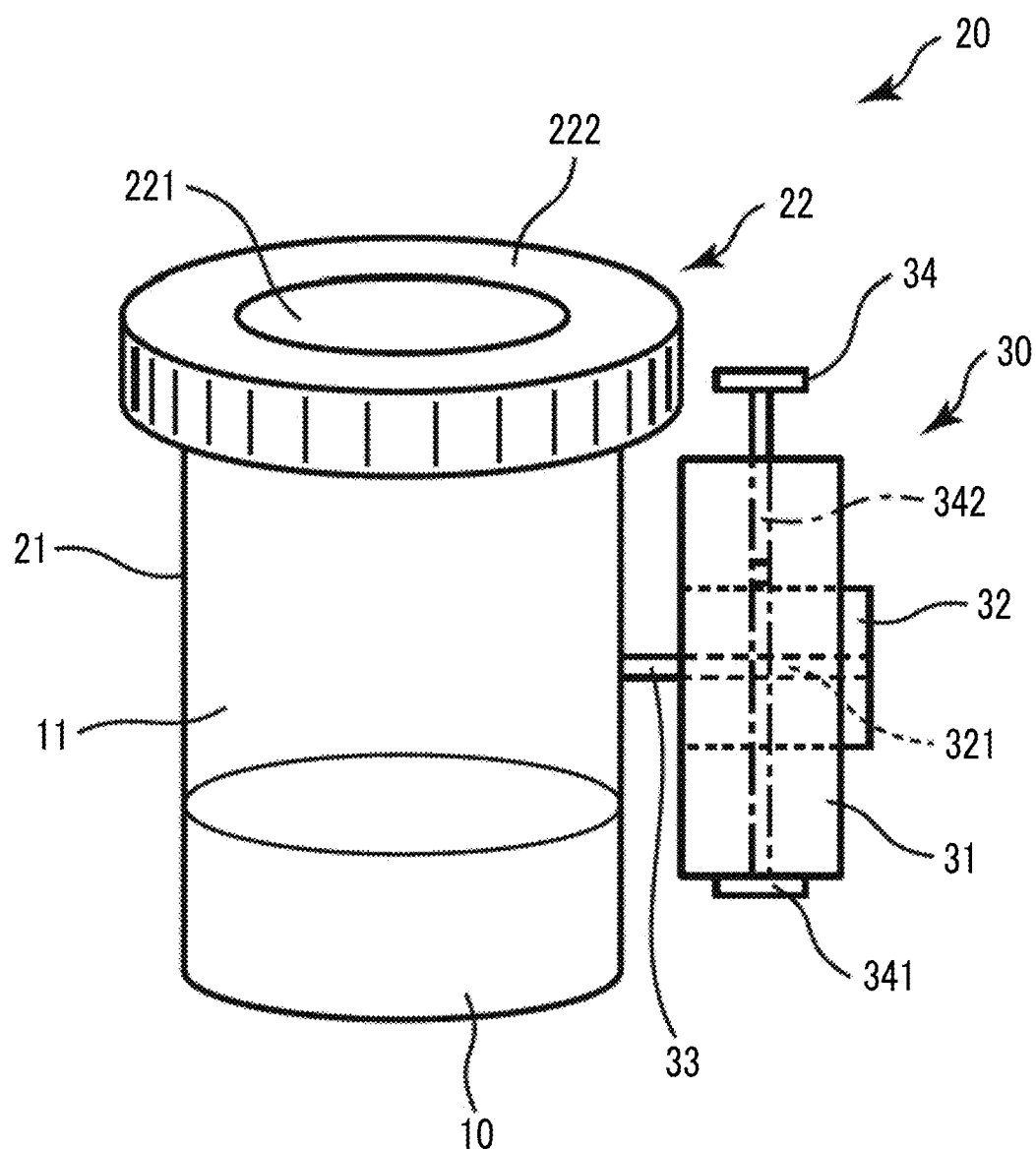
FIG. 14 is a perspective view for illustrating a manufacturing container used in a ninth embodiment of the method for manufacturing bubbles of the present invention.

FIG. 14 is a perspective view for illustrating a manufacturing container used in the ninth embodiment of the method for manufacturing bubbles of the present invention.

In the following description, the upper side in FIG. 14 will be referred to as "top", and the lower side in FIG. 14 will be referred to as "bottom". Furthermore, the left side in FIG. 14 will be referred to as "left", and the right side in FIG. 14 will be referred to as "right".

Hereinafter, regarding the method for manufacturing bubbles of the ninth embodiment, the differences between the methods for manufacturing bubbles of the first to eighth embodiments and the method for manufacturing bubbles of the present embodiment will be mainly described, and the same details will not be described.

The method for manufacturing bubbles of the present embodiment is different from the method for manufacturing bubbles of the eighth embodiment described above in that the Mininert valve 30 is is provided on the lateral surface of the container body 21.

As shown in FIG. 14, the manufacturing container 20 (the fifth embodiment of the bubble manufacturing container) used in the present embodiment includes the container body 21, the lid 22, the Mininert valve 30, and the tube 33 which connects the container body 21 to the Mininert valve 30, which are used in the method for manufacturing bubbles of the eighth embodiment described above. Furthermore, in the manufacturing container 20 of the present embodiment, the Mininert valve 30 is provided on the lid 22 side (upper side in the drawing) above the surface of the aqueous liquid 10.

The tube 33 is constituted with a tube (pipe) made of glass and integrally formed with the container body 21 (vial).

As shown in FIG. 14, a left end portion of the tube 33 is in communication with the interior space (void portion 11) of the container body 21, and a right end portion of the tube 33 is in communication with the duct 321 of the rubber stopper 32. Accordingly, in the present embodiment, the duct 321 and the interior space of the container body 21 are also in communication with each other through the tube 33.

By using the manufacturing container 20 constituted as above, a bubble-containing container can be obtained through the same steps as in the method for manufacturing bubbles of the eighth embodiment described above.

With the method for manufacturing bubbles of the ninth embodiment, the same operations and effects as in the methods for manufacturing bubbles of the first to eighth embodiments are also obtained.

Tenth Embodiment

Next, a tenth embodiment of the method for manufacturing bubbles of the present invention will be described.

Figure 15:
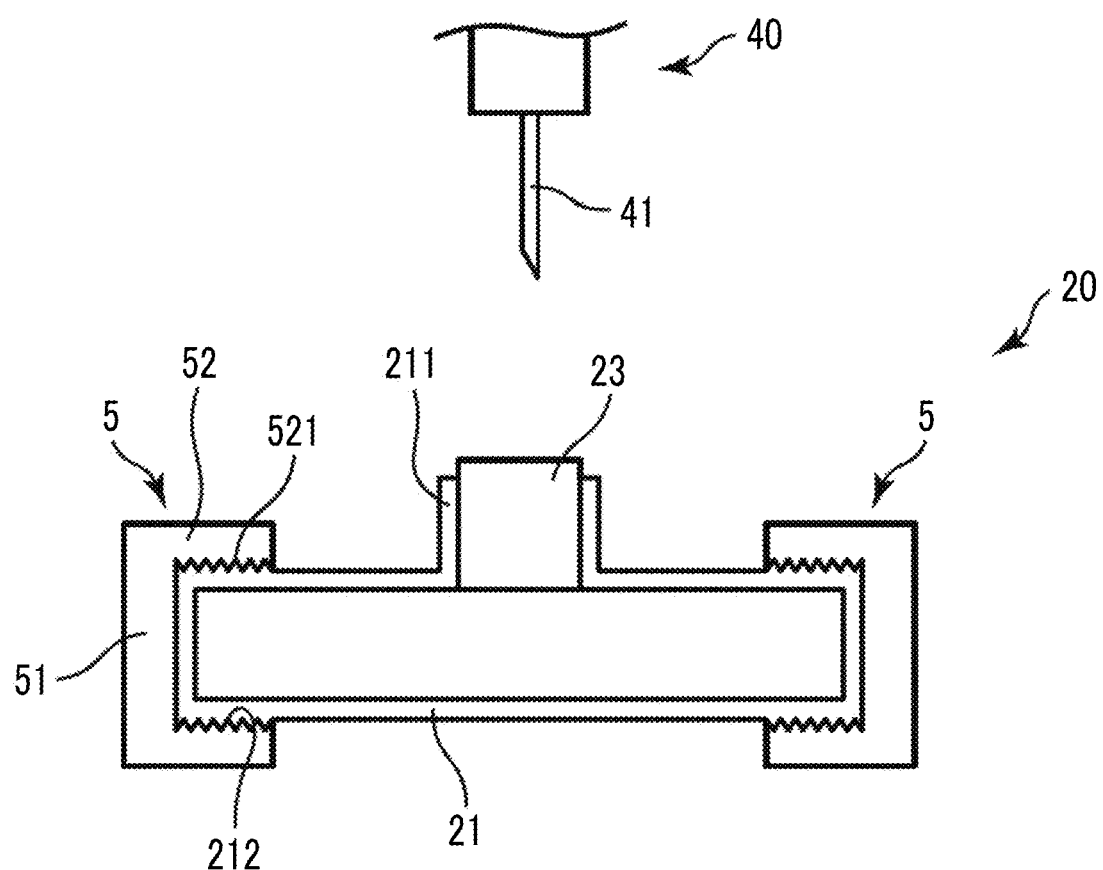
FIG. 15 is a cross-sectional view for illustrating a manufacturing container used in a tenth embodiment of the method for manufacturing bubbles of the present invention.

FIG. 15 is a cross-sectional view for illustrating a manufacturing container used in the tenth embodiment of the method for manufacturing bubbles of the present invention.

In the following description, the upper side in FIG. 15 will be referred to as "top", and the lower side in FIG. 15 will be referred to as "bottom". Furthermore, the left side in FIG. 15 will be referred to as "left", and the right side in FIG. 15 will be referred to as "right".

Hereinafter, regarding the method for manufacturing bubbles of the tenth embodiment, the differences between the methods for manufacturing bubbles of the first to ninth embodiments and the method for manufacturing bubbles of the present embodiment will be mainly described, and the same details will not be described.

The bubble manufacturing container of the present embodiment is constituted such that the longitudinal direction thereof becomes substantially a horizontal direction (in the first to ninth embodiments described above, the longitudinal direction of the manufacturing container 20 is a vertical direction). In Step (S4), the manufacturing container is vibrated in the horizontal direction. In this respect, the method for manufacturing bubbles of the present embodiment is different from the methods for manufacturing bubbles of the first to ninth embodiments described above. Specifically, in Step (S4), the manufacturing container 20 shown in FIG. 15 is vibrated such that it reciprocates substantially in the horizontal direction thereof.

[S1] Preparation Step

The manufacturing container 20 (the sixth embodiment of the bubble manufacturing container) shown in FIG. 15 is prepared.

The manufacturing container 20 of the present embodiment includes the container body 21 having a cylindrical portion 211 on the top portion thereof, a rubber stopper 23 sealing an opening of the cylindrical portion 211, and two weight portions 5 fixed to both end portions of the container body 21.

The container body 21 has an approximately cylindrical shape that is long in the horizontal direction (right and left direction in FIG. 15). Approximately at the center of the container body 21, the cylindrical portion (projection portion) 211 is formed which projects in the vertical direction from the top surface of the container body 21. In the container body 21 of the present embodiment, only the opening of the cylindrical portion 211 is opened to the outside. At both end sides of the container body 21, a screw groove 212 is formed.

The rubber stopper 23 is not particularly limited, and for example, a rubber stopper made of silicon can be used.

The weight portions 5 each have a disk-like flat plate portion 51 and a cylindrical portion 52 that stands on the edge of the flat plate portion 51. When seen in a cross-sectional view, each of the weight portions 5 looks like an approximately C-shaped member. On the inner circumferential side of the cylindrical portion 52, the screw groove 521 is formed which can be screwed with the screw groove 212 of the container body 21. By screwing the screw groove 521 of the weight portions 5 with the screw groove 212 of the container body 21, the weight portions 5 are mounted on (fixed to) the container body 21 in a state where the flat plate portion 51 adheres to each of the end portions of the container body 21.

Similarly to the bottom plate portion 223 of the lid 22 shown in FIG. 9 described above, the weight portions 5 are each constituted with a material having a relatively high specific gravity, such as a ceramic material and a metal material. Therefore, by mounting the weight portions 5 on the container body 21, the masses of both end portions of the container body 21 can be increased. In this way, in Step (S4), it is possible to further increase the magnitude of the shock waves that occur when the aqueous liquid 10 collides with the portion (particularly, both end portions) of the container body 21 fixed to the weight portions 5. As a result, fine bubbles 1 can be more easily and stably generated in the aqueous liquid 10.

As the material constituting the weight portions 5, among metal materials, iron or an iron alloy such as stainless steel is particularly preferable, because these materials have high specific gravity and exhibit high corrosion resistance with respect to the components constituting the aqueous liquid 10.

The weight portions 5 can be easily detached from and attached to the container body 21. By changing the constituent materials and/or the size of the weight portions 5, the masses of the weight portions 5 can be appropriately adjusted. By adjusting the masses of the weight portions 5, in Step (S4), the size and amount of the bubbles 1 generated in the aqueous liquid 10 can be adjusted. That is, in the method for manufacturing bubbles of the present embodiment, the bubbles 1 of various sizes and contents can be manufactured using the same manufacturing container 20. Therefore, it is not necessary to prepare plural kinds of manufacturing containers 20 of different sizes according to the bubbles 1 of intended sizes and contents, and hence the productivity of the bubble-containing container is improved.

[S3] Step of Sealing Manufacturing Container

By using the gas 3, purging is performed in the container body 21 into which the aqueous liquid 10 is injected. Then, the rubber stopper 23 is inserted into the opening of the cylindrical portion 211 of the container body 21. In this way, the aqueous liquid 10 and the gas 3 are sealed in the manufacturing container 20.

Then, the syringe 40 filled with the gas 3 is prepared, and the injection needle 41 of the syringe 40 is pierced into the rubber stopper 23. Thereafter, the gas 3 is further added into the manufacturing container 20 from the syringe 40. In this way, the interior of the manufacturing container 20 is pressurized. Then, by pulling the injection needle out of the rubber stopper 23, it is possible to obtain the manufacturing container 20 which is sealed in a state where the interior of the manufacturing container 20 is pressurized due to the gas 3.

[S4] Step of Vibrating Manufacturing Container

Then, the manufacturing container 20 is vibrated such that the aqueous liquid 10 repeatedly collides with the both end portions and the later surface (particularly, the both end portions) of the manufacturing container 20. In the present embodiment, the manufacturing container 20 is vibrated such that it substantially reciprocates in the horizontal direction (longitudinal direction) of the manufacturing container 20.

In the present embodiment, the manufacturing container 20 can be vibrated under the same condition as in Step (S4) in the first embodiment described above.

By performing the following steps in the same manner as in the first to fifth embodiments described above, a large amount of bubbles 1 having a uniform size can be stably manufactured in the manufacturing container 20. In addition, the manufacturing container (sealed container) 20 (bubble-containing container) containing the large amount of bubbles 1 having the uniform size is obtained.

With the method for manufacturing bubbles of the tenth embodiment, the same operations and effects as in the methods for manufacturing bubbles of the first to ninth embodiments are also obtained.

Eleventh Embodiment

Next, an eleventh embodiment of the method for manufacturing bubbles of the present invention will be described.

Figure 16:
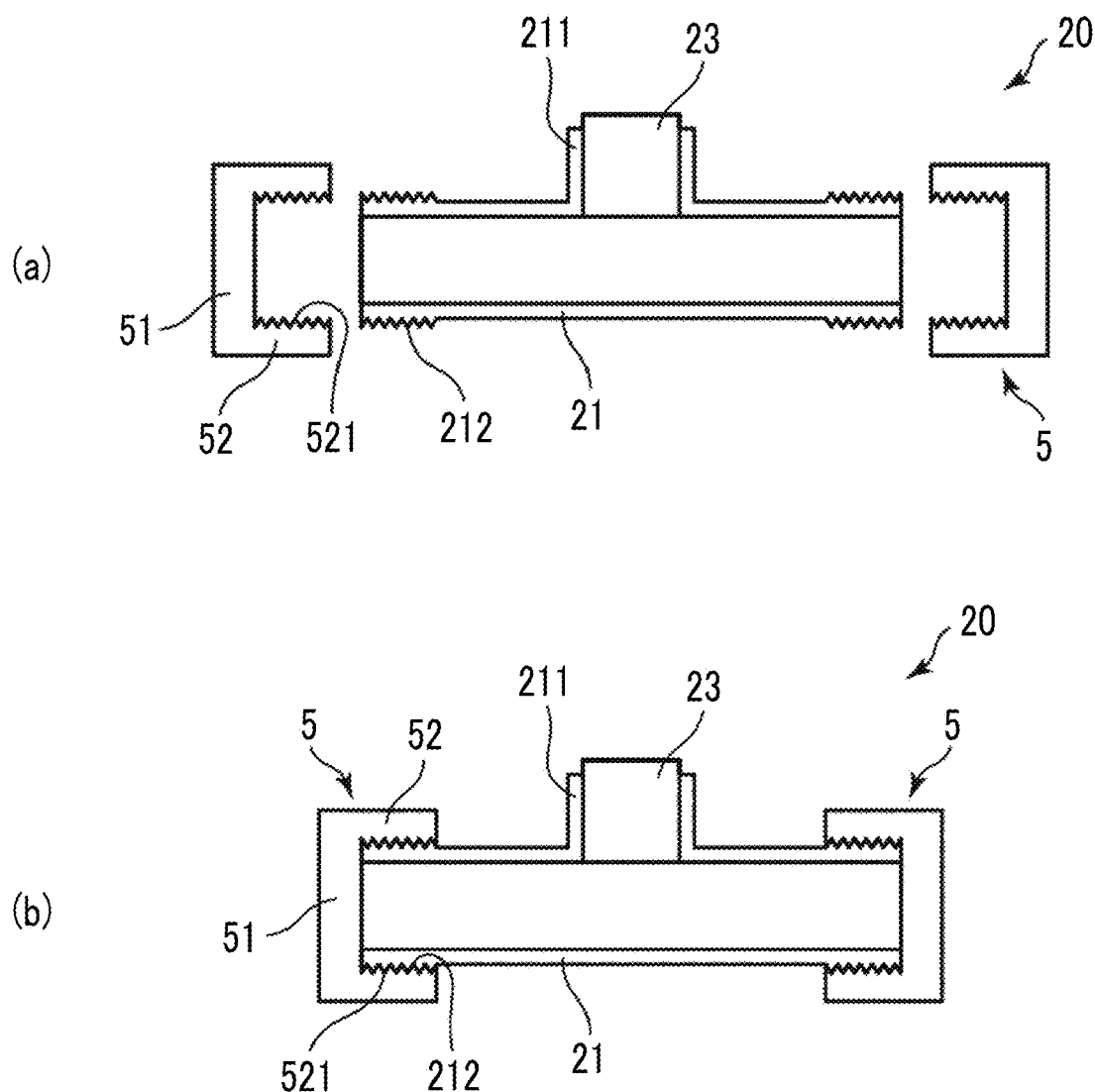
FIG. 16 shows cross-sectional views for illustrating a manufacturing container used in an eleventh embodiment of the method for manufacturing bubbles of the present invention.

FIG. 16 shows cross-sectional views for illustrating a manufacturing container used in the eleventh embodiment of the method for manufacturing bubbles of the present invention. FIG. 16(*a*) shows the manufacturing container in a disassembled state, and FIG. 16(*b*) shows the manufacturing container in an assembled state.

In the following description, the upper side in each of FIGS. 16(*a*) and 16(*b*) will be referred to as "top", and the lower side in each of FIGS. 16(*a*) and 16(*b*) will be referred to as "bottom". Furthermore, the left side in each of FIGS. 16(*a*) and 16(*b*) will be referred to as "left", and the right side in each of FIGS. 16(*a*) and 16(*b*) will be referred to as "right".

Hereinafter, regarding the method for manufacturing bubbles of the eleventh embodiment, the differences between the methods for manufacturing bubbles of the first to tenth embodiments and the method for manufacturing bubbles of the present embodiment will be mainly described, and the same details will not be described.

The method for manufacturing bubbles of the present embodiment is the same as the method for manufacturing bubbles of the tenth embodiment described above in which the manufacturing container 20 shown in FIG. 15 is used, except that both ends of the container body 21 of the manufacturing container 20 (the seventh embodiment of the bubble manufacturing container) are opened to the outside as shown in FIGS. 16(*a*) and 16(*b*). That is, the container body 21 is constituted with a cylindrical member whose both ends are opened to the outside.

In a case where the manufacturing container 20 constituted as above is used, first, by screwing the screw grooves 521 of the weight portions 5 with the screw grooves 212 of the container body 21, the weight portions 5 are mounted on the container body 21. As shown in FIG. 16(*b*), in a state where the weight portions 5 are mounted on the container body 21, the flat plate portion 51 adheres to each of the end portions of the container body 21.

Between the flat plate portion 51 and each of the both end portions of the container body 21, a packing for improving the adhesion between the weight portions 5 and the container body 21 may be disposed, although this constitution is not shown in the drawing. In this way, the sealing property of the manufacturing container 20 can be improved.

Then, through the same steps as in the method for manufacturing bubbles of the present embodiment described above, a bubble-containing container can be obtained.

By piercing an injection needle of a syringe into the rubber stopper 23 and then aspirating the bubble-containing liquid, the bubble-containing container obtained as above can be used. In this constitution, by detaching the weight portions 5 from the container body 21, it is possible to directly take the bubble-containing liquid out of the bubble-containing container without using the syringe.

With the method for manufacturing bubbles of the eleventh embodiment, the same operations and effects as in the methods for manufacturing bubbles of the first to tenth embodiments are also obtained.

Twelfth Embodiment

Next, a twelfth embodiment of the method for manufacturing bubbles of the present invention will be described.

Figure 17:
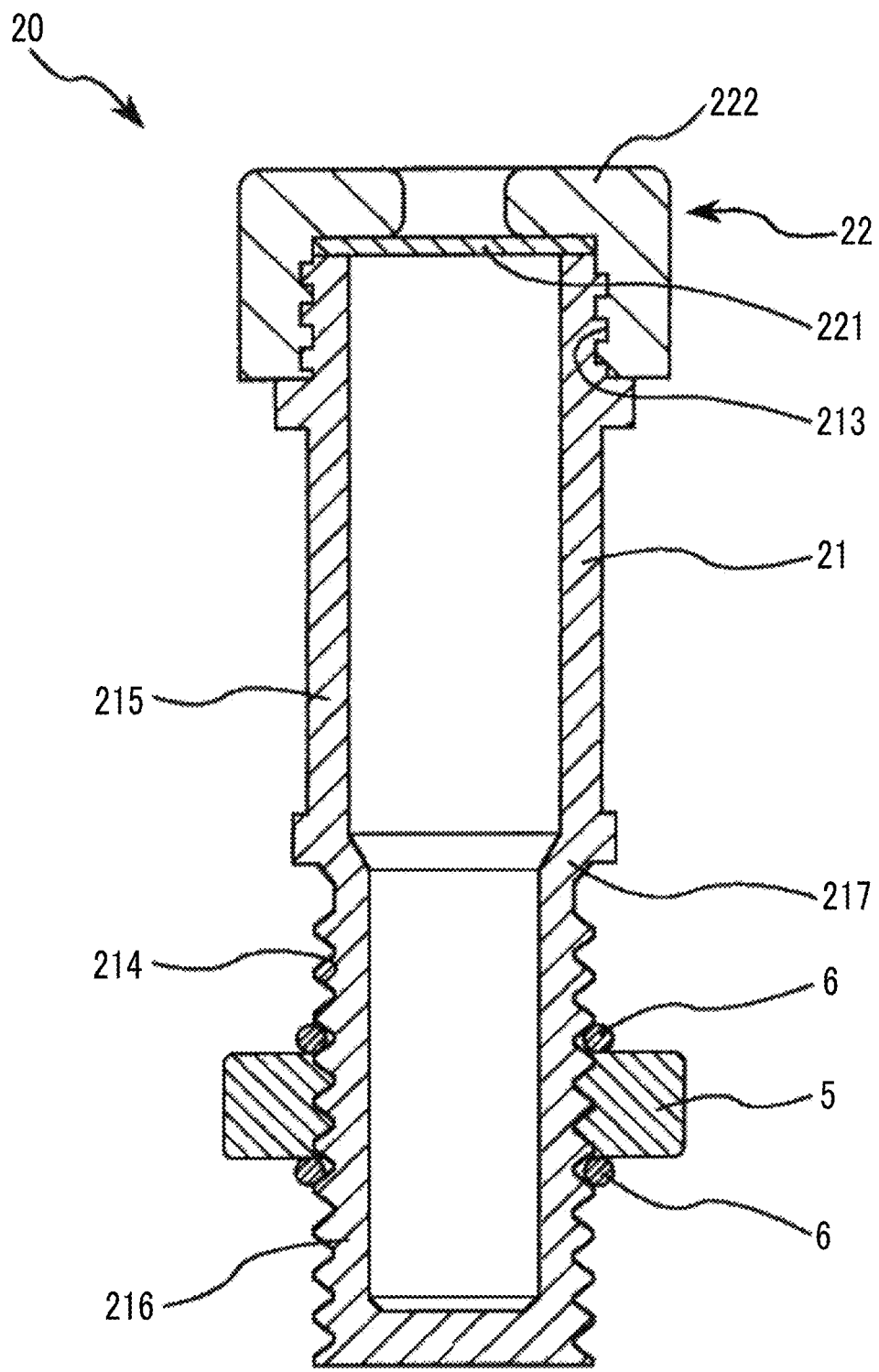
FIG. 17 is a cross-sectional view for illustrating a manufacturing container used in a twelfth embodiment of the method for manufacturing bubbles of the present invention.

FIG. 17 is a cross-sectional view for illustrating a manufacturing container used in the twelfth embodiment of the method for manufacturing bubbles of the present invention.

In the following description, the upper side in FIG. 17 will be referred to as "top", and the lower side in FIG. 17 will be referred to as "bottom".

Hereinafter, regarding the method for manufacturing bubbles of the twelfth embodiment, the differences between the methods for manufacturing bubbles of the first to eleventh embodiments and the method for manufacturing bubbles of the present embodiment will be mainly described, and the same details will not be described.

The method for manufacturing bubbles of the present embodiment is the same as the methods for manufacturing bubbles of the first to fifth embodiments described above, except that the manufacturing container has a different constitution.

[S1] Preparation Step

The manufacturing container 20 (the eighth embodiment of the bubble manufacturing container) shown in FIG. 17 is prepared.

The manufacturing container 20 of the present embodiment includes the container body 21, the lid 22 sealing the container body 21, the weight portion 5 provided on the other end side of the container body 21 such that the weight portion 5 can move in the longitudinal direction of the container body 21, and a pair of O-rings 6 fixing the weight portion 5. The lid 22 has the same constitution as the lid 22 of the manufacturing container 20 of the first embodiment described above.

The container body 21 has an approximately bottomed cylindrical shape. The container body 21 includes a top body portion 215 on which the lid 22 is mounted and a bottom body portion 216 on which the weight portion 5 is mounted and which has an inner diameter smaller than that of the top body portion 215. As shown in FIG. 17, the top body portion 215 has, on the bottom end portion thereof, a diameter-reduced portion 217 reduced so as to become the same as the inner diameter of the bottom body portion 216. On an outer circumferential surface of one end side (top end side) of the top body portion 215, a screw groove 213 which can be screwed with the fastening portion 222 (inner circumferential surface of the fastening portion 222) of the lid 22 is formed. Furthermore, on the entirety of the outer circumferential surface of the bottom body portion 216, a screw groove 214 which can be screwed with the weight portion 5 (inner circumferential surface of the weight portion 5) is formed.

The material constituting the container body 21 is not particularly limited, and various ceramic materials such as glass, a resin material, and the like can be used.

The length of the top body portion 215 in the longitudinal direction is not particularly limited, but is preferably about 10 to 60 mm and more preferably about 15 to 30 mm. The inner diameter of the top body portion 215 is preferably about 5 to 20 mm, and more preferably about 8 to 15 mm. The length of the bottom body portion 216 in the longitudinal direction is not particularly limited, but is preferably about 10 to 35 mm and more preferably about 13 to 23 mm. The inner diameter of the bottom body portion 216 is not particularly limited as long as it is smaller than the inner diameter of the top body portion 215. The inner diameter of the bottom body portion 216 is preferably about 2 to 15 mm, and more preferably about 3 to 8 mm.

In a case where the container body 21 having such dimensions is used, an appropriate pressure is applied to the aqueous liquid 10 in the sealed space within the container body 21. Therefore, the bubbles 1 having the uniform size can be stably obtained. Furthermore, in this case, at the time of the ultrasonic diagnosis, since the bubble-containing liquid in a single manufacturing container 20 can be used up, it is possible to eliminate a waste of the manufactured bubble-containing liquid.

In a case where the inner diameter of the top body portion 215 and the inner diameter of the bottom body portion 216 are within the aforementioned range, a big difference occurs between the inner diameter of the top body portion 215 and the inner diameter of the bottom body portion 216, and the size of the diameter-reduced portion 217 increases. Accordingly, in Step (S4), when moving to the bottom body portion 216 side from the top body portion 215, the aqueous liquid 10 collides with the diameter-reduced portion 217, and hence shock waves occur. In this way, due to the existence of the diameter-reduced portion 217, the shock waves can more frequently occur in the manufacturing container 20, compared to a case where a container having the same inner diameter is used.

Furthermore, in the step of vibrating the manufacturing container 20, the aqueous liquid 10 moves to the bottom body portion 216 from the top body portion 215, and hence the movement speed of the aqueous liquid 10 increases. Accordingly, due to a cavitation effect, the bubbles are more easily generated in the aqueous liquid 10 within the bottom body portion 216. Due to this synergistic effect, the bubbles 1 having the uniform particle size can be more efficiently generated in a shorter period of time.

The screw groove 214 is formed on the entirety of an outer circumferential surface of the bottom body portion 216. Therefore, as long as the length thereof in the longitudinal direction is within the aforementioned range, the weight portion 5 can be moved to the vicinity of the center from the bottom end of the container body 21.

In a case where the weight portion 5 is provided in the vicinity of the bottom end of the container body 21, the weight of the bottom end portion of the container body 21 increases. Therefore, as in the tenth embodiment described above, in Step (S4), it is possible to increase the magnitude of the shock waves that occur when the aqueous liquid 10 collides with the bottom end portion of the container body 21.

In contrast, in a case where the weight portion 5 is positioned in the vicinity of the center of the container body 21, the weight of the diameter-reduced portion 217 increases. Accordingly, in Step (S4), it is possible to increase the magnitude of the shock waves that occur when the aqueous liquid 10 collides with the diameter-reduced portion 217.

The closer the position of the weight portion 5 is to the bottom end portion of the container body 21, the stronger the shock waves that occur when the aqueous liquid 10 collides with the bottom end portion of the container body 21. That is, in the present embodiment, by adjusting the position of the weight portion 5 to be provided in the bottom body portion 216, the magnitude of the shock waves occurring in the manufacturing container 20 can be controlled, and hence the bubbles 1 having an intended size can be stably generated.

The total length of the container body 21 in the longitudinal direction is not particularly limited, but is preferably about 20 to 85 mm and more preferably about 30 to 53 mm.

The weight portion 5 is a ring-shaped member. By rotating the weight portion 5 in a state where the weight portion 5 is screwed with the screw groove 214 of the bottom body portion 216, the weight portion 5 moves in the region of the bottom body portion 216, in which the screw groove 214 is formed, in the longitudinal direction (vertical direction in FIG. 17).

As described above, in the method for manufacturing bubbles of the present embodiment, by setting the position in which the weight portion 5 is provided in the container body 21, the magnitude of the shock waves occurring in the manufacturing container 20 can be controlled. In this way, the size and content of the obtained bubbles 1 can be adjusted.

The mass of the weight portion 5 is not particularly limited, but is preferably about 3 to 30 g and more preferably about 5 to 20 g for the container body 21 having the aforementioned dimensions. In a case where the mass of the weight portion 5 is within the aforementioned range, the size and content of the obtained bubbles 1 can be more efficiently adjusted.

The O-rings 6 are provided on the upper side and the lower side of the weight portion 5 as if sandwiching the weight portion 5 therebetween. The O-rings 6 are members that prevent the weight portion 5 from moving due to the vibration of the manufacturing container 20 or the like. As the O-rings 6, O-rings made of silicon can be used.

The weight portion 5 and the O-rings 6 can be mounted on the container body 21 in the following manner. First, one of the O-rings 6 is put on the container body 21 from the bottom end side of the bottom body portion 216 and then stopped in a predetermined position. Then, the weight portion 5 is mounted on the bottom end portion of the bottom body portion 216 and moved until the weight portion 5 contacts with the O-ring 6 mounted. Then, the other O-ring 6 is put on the container body 21 from the bottom end side of the bottom body portion 216 and moved until the O-ring 6 contacts with the weight portion 5, and in this way, the weight portion 5 is fixed by the two O-rings 6.

By performing the following steps in the same manner as in the first to fifth embodiments described above, the large amount of bubbles 1 having the uniform size can be stably manufactured in the manufacturing container 20. In addition, the manufacturing container (sealed container) 20 (bubble-containing container) containing the large amount of bubbles 1 having the uniform size is obtained.

With the method for manufacturing bubbles of the twelfth embodiment, the same operations and effects as in the methods for manufacturing bubbles of the first to eleventh embodiments are also obtained.

Thirteenth Embodiment

Next, a thirteenth embodiment of the method for manufacturing bubbles of the present invention will be described.

Figure 19:
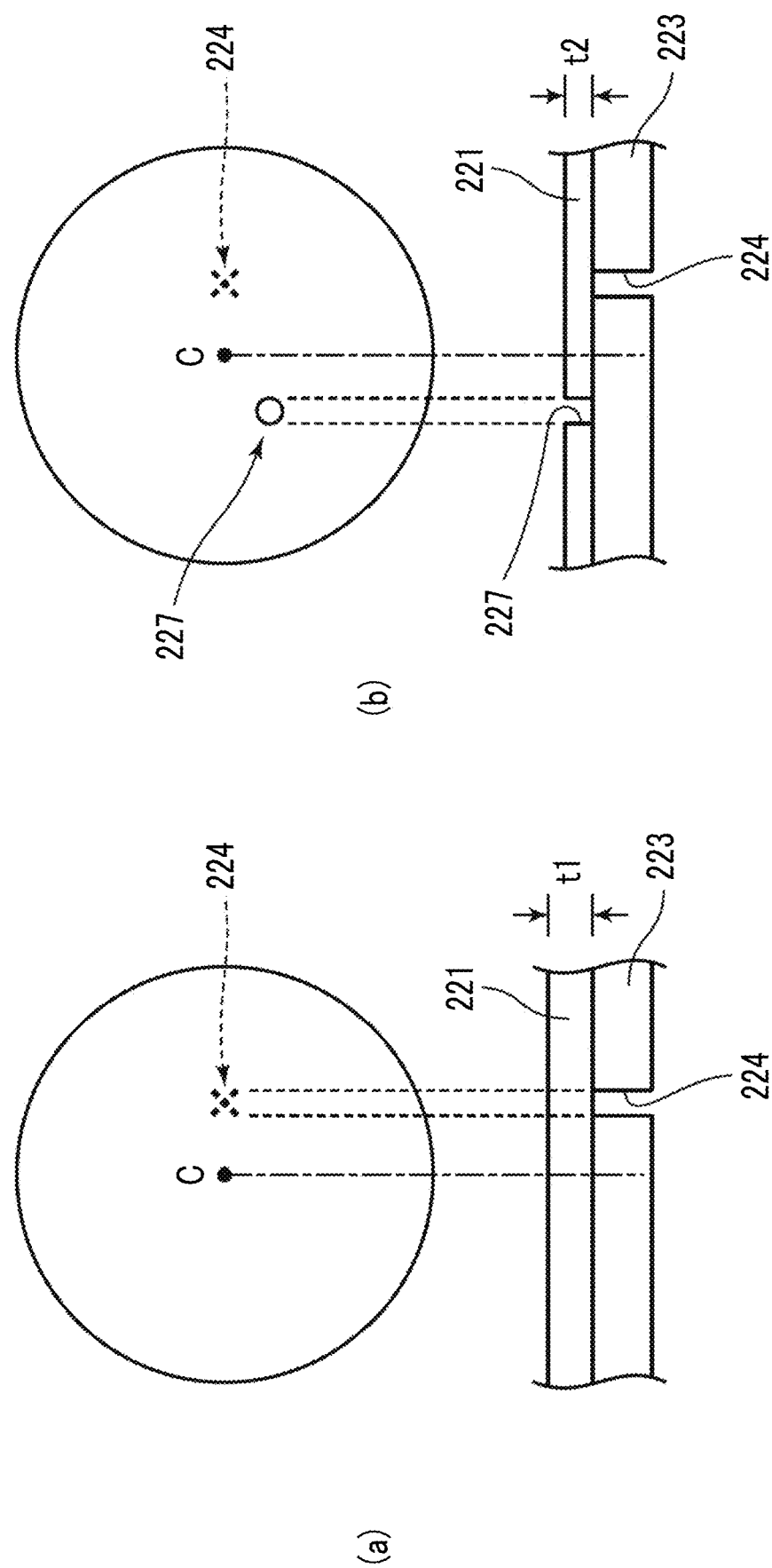
FIG. 19 shows views for illustrating positions of an opening portion formed in a lid of the manufacturing container shown in FIG. 18(b).

FIG. 18 shows cross-sectional views for illustrating a manufacturing container used in the thirteenth embodiment of the method for manufacturing bubbles of the present invention. FIG. 18(a) shows the manufacturing container in a disassembled state, and FIG. 18(b) shows the manufacturing container in an assembled state. FIG. 19 shows views for illustrating positions of an opening portion formed in a lid of the manufacturing container shown in FIG. 18(b). FIG. 19(a) is a view for illustrating a state where an injection needle of a syringe is not yet pierced into a rubber stopper, and FIG. 19(b) is a view for illustrating a state where a fastening portion is fastened to a bottom plate portion after the injection needle is pulled out of the rubber stopper.

In the following description, the upper side in each of FIGS. 18(a) and 18(b) will be referred to as "top", and the lower side in each of FIGS. 18(a) and 18(b) will be referred to as "bottom". Furthermore, the left side in each of FIGS. 18(a) and 18(b) will be referred to as "left", and the right side in each of FIGS. 18(a) and 18(b) will be referred to as "right".

Hereinafter, regarding the method for manufacturing bubbles of the thirteenth embodiment, the differences between the methods for manufacturing bubbles of the first to twelfth embodiments and the method for manufacturing bubbles of the present embodiment will be mainly described, and the same details will not be described.

The method for manufacturing bubbles of the present embodiment is the same as the methods for manufacturing bubbles of the first to fifth embodiments described above, except that the lid of the manufacturing container has a different constitution.

[S1] Preparation Step

The manufacturing container 20 (the ninth embodiment of the bubble manufacturing container) shown in FIG. 18(b) is prepared.

The manufacturing container 20 of the present embodiment includes the same container body 21 as that of the manufacturing container 20 of the first embodiment described above, and the lid 22.

In the present embodiment, the lid 22 includes the bottom plate portion 223 fixed to the vial mouth of the container body 21, the rubber stopper 221 disposed on the bottom plate portion 223 on the side opposite to the container body 21, and the fastening portion 222 fixing the rubber stopper 221 to the bottom plate portion 223.

The bottom plate portion 223 includes a disk-like flat plate portion 225 and a cylindrical portion 226 that stands on the edge of the flat plate portion 225. When seen in a cross-sectional view, the bottom plate portion 223 looks like an approximately C-shaped member. In the present embodiment, when seen in a plan view (top view), the shape of the bottom plate portion 223 (flat plate portion 225) is practically the same as the shape of the rubber stopper 221, and the diameter of the bottom plate portion 223 is practically the same as that of the rubber stopper 221. Furthermore, on the inner circumferential surface of the cylindrical portion 226 and the outer circumferential surface of the container body 21 on the vial mouth side, screw grooves which can be screwed with each other are formed. By screwing these grooves with each other, the bottom plate portion 223 (flat plate portion 225) is fixed to the vial mouth of the container body 21 in a state of adhering to the vial mouth.

When seen in a plan view (top view), in the bottom plate portion 223, a through hole 224, having a size that allows an injection needle of a syringe to be inserted thereinto, is formed in a position separated from the center of the bottom plate portion 223 by a predetermined distance. That is, as shown in FIG. 19(a), when seen in the plan view, in the lid 22, the center C of the rubber stopper 221 deviates from the through hole 224 of the bottom plate portion 223.

Similarly to the bottom plate portion 223 of the lid 22 shown in FIG. 9 described above, the aforementioned bottom plate portion 223 is constituted with a material having a high specific gravity, such as a ceramic material and a metal material. By increasing the mass of the bottom plate portion 223, in Step (S4), it is possible to further increase the magnitude of the shock waves that occur when the aqueous liquid 10 collides with the top surface (bottom plate portion 223) of the manufacturing container 20. As a result, fine bubbles 1 can be more easily and stably generated in the aqueous liquid 10.

As the rubber stopper 221, it is possible to use the same rubber stopper as the rubber stopper 221 used in the method for manufacturing bubbles of the first embodiment described above. On the surface of the rubber stopper 221, in a state where the lid 22 is mounted on the container body 21, a mark X is made which is for piercing an injection needle in a position corresponding to the through hole 224 of the bottom plate portion 223 (see FIG. 19(a)).

The fastening portion 222 is constituted such that it covers the edge of the rubber stopper 221. Furthermore, on the outer circumferential surface of the fastening portion 222 and the bottom plate portion 223 (flat plate portion 225), screw grooves that can be screwed with each other are formed. By screwing the grooves with each other, the rubber stopper 221 is fixed to the bottom plate portion 223 (flat plate portion 225) in a state of adhering to the bottom plate portion 223.

[S3] Step of Sealing Manufacturing Container

First, by using the gas 3, purging is performed in the void portion 11 of the container body 21 into which the aqueous liquid 10 is injected. Then, the lid 22 is inserted into the opening portion (vial mouth) of the container body 21 (the state shown in FIG. 19(a)). In this way, the aqueous liquid 10 and the gas 3 are sealed in the manufacturing container 20.

In the state shown in FIG. 19(a), an injection needle of a syringe filled with the gas 3 is pierced into the rubber stopper 221 at the mark X and inserted into the through hole 224 of the bottom plate portion 223. Then, the gas 3 is further added into the manufacturing container 20 from the syringe such that the interior of the manufacturing container 20 is pressurized, and the injection needle is pulled out of the rubber stopper 221.

Thereafter, by turning the fastening portion 222, the fastening portion 222 is fastened to the bottom plate portion 223 (the state shown in FIG. 19(b)). By fastening the fastening portion 222 to the bottom plate portion 223, the rubber stopper 221 is compressed toward the bottom plate portion 223 side while rotating (for example, rotating 180°) with respect to the bottom plate portion 223. Accordingly, when seen in a plan view, a position of a through hole 227 formed in the rubber stopper 221 due to the injection needle pierced into the stopper deviates from the position of the through hole 224 of the bottom plate portion 223 (see FIG. 19(b)). As a result, the through hole 224 of the bottom plate portion 223 is closed due to the rubber stopper 221, and it is possible to obtain the manufacturing container 20 which is sealed in a state where the interior of the manufacturing container 20 is pressurized due to the gas 3.

In the present embodiment, there is no portion that makes the interior of the manufacturing container 20 communicate with the outside, and hence the sealing property of the interior of the manufacturing container 20 can be improved. Due to the improvement of the sealing property of the interior of the manufacturing container 20, the bubbles 1 can more stably exist in the aqueous liquid 10 within the finally obtained bubble-containing container. That is, the long-term storability of the bubble-containing container is further improved.

As described above, by fastening the fastening portion 222 to the bottom plate portion 223, the rubber stopper 221 is compressed toward the bottom plate portion 223 side. Provided that a thickness of the rubber stopper 221 in a state where the fastening portion 222 is not yet fastened to the bottom plate portion 223 is $t_1$ (mm), and that a thickness of the rubber stopper 221 in a state where the fastening portion 222 is fastened to the bottom plate portion 223 is $t_2$ (mm), a compression rate (($t_1-t_2$)/$t_1$×100) of the rubber stopper 221 is preferably 5% to 60%, and more preferably 10% to 30%. In a case where the compression rate is as described above, it is possible to further improve the adhesion between the rubber stopper 221 and the bottom plate portion 223 while suppressing the load imposed on the rubber stopper 221 due to the fastening of the fastening portion 222. As a result, the sealing property of the interior of the manufacturing container 20 can be further improved.

In the present embodiment, the large amount of bubbles 1 having the uniform size can also be stably manufactured in the manufacturing container 20. In addition, the manufacturing container 20 (bubble-containing container) containing the large amount of bubbles 1 having the uniform size is obtained.

With the method for manufacturing bubbles of the thirteenth embodiment, the same operations and effects as in the methods for manufacturing bubbles of the first to twelfth embodiments are also obtained.

Hitherto, the method for manufacturing bubbles and the bubble manufacturing container of the present invention have been described based on the embodiments illustrated in drawings. However, the present invention is not limited thereto, and each step can be substituted with any step that can perform the same function.

For example, certain constitutions of the first to thirteenth embodiments can be combined with each other.

EXAMPLES

In order to explain the influence of the volume of the gas 3 sealed in the manufacturing container 20 and the number of revolution of the manufacturing container 20 on the diameter and content of the bubble 1 generated in the aqueous liquid 10, the following experiments were performed.

Example 1

First, relationships between the number of revolution of the manufacturing container 20 and the diameter and content of the bubbles 1 generated in the aqueous liquid 10 were investigated.

(Method for Manufacturing Bubbles)

[Preparation Step]

First, 120 µl of an albumin solution (ALBUMINAR 25% manufactured by CSL Behring) containing albumin at 250 mg/ml and 12 ml of 25% phosphate-buffered saline (PBS) were prepared. Furthermore, a 15 ml vial (height X: 50 mm, outer diameter R: 25 mm) was prepared. The vial had the same shape as that of the manufacturing container 20 shown in FIG. 4.

[Step of Injecting Aqueous Liquid into Container]

The entireties of the albumin solution and the 25% phosphate-buffered saline were injected into the prepared vial. Here, a height Y of a surface of an aqueous liquid obtained by mixing the albumin solution with the 25% phosphate-buffered saline was 25 mm.

[Step of Sealing Container]

Figure 4:
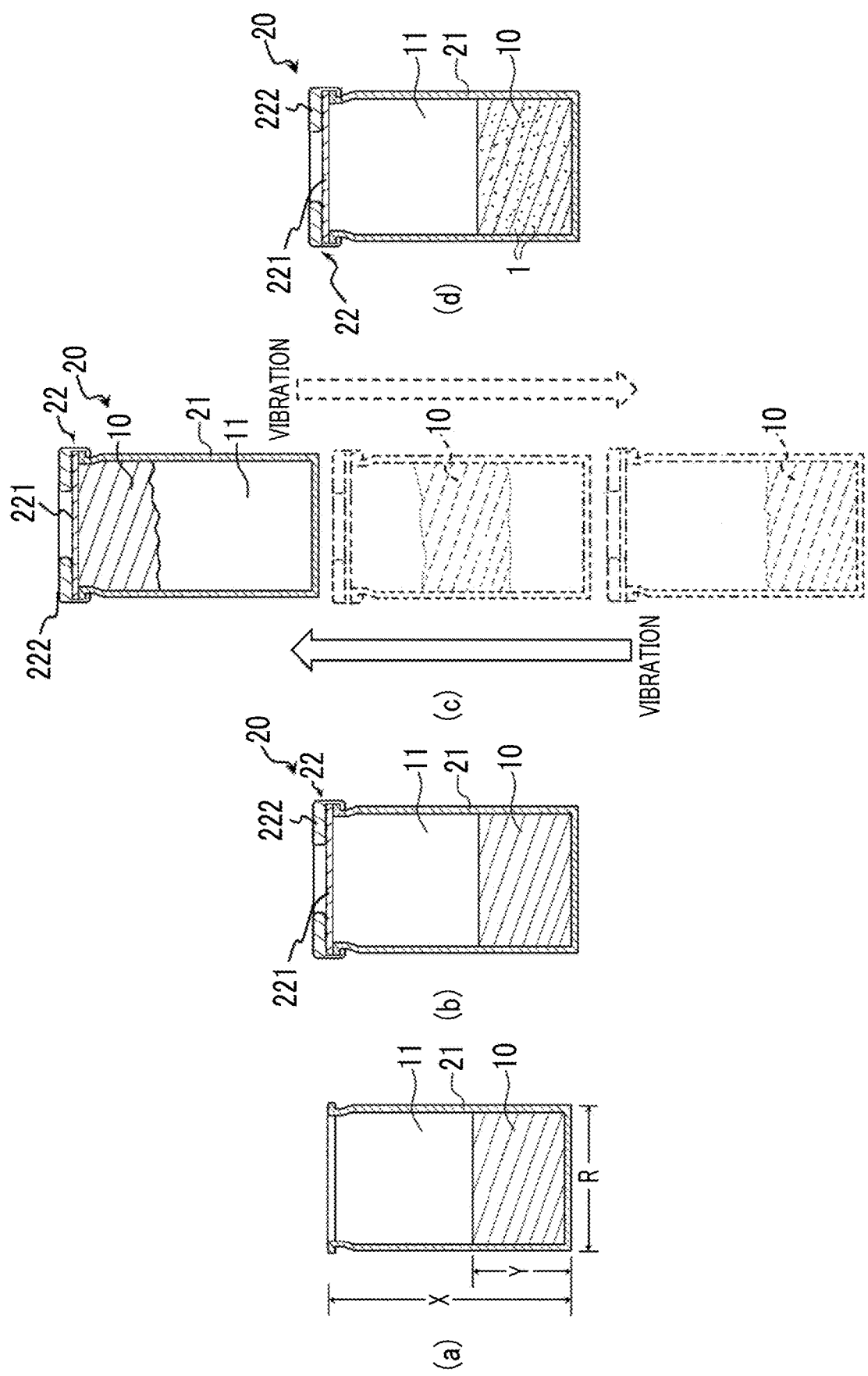
FIG. 4 shows cross-sectional views for illustrating the first embodiment of the method for manufacturing bubbles of the present invention.
Figure 5:
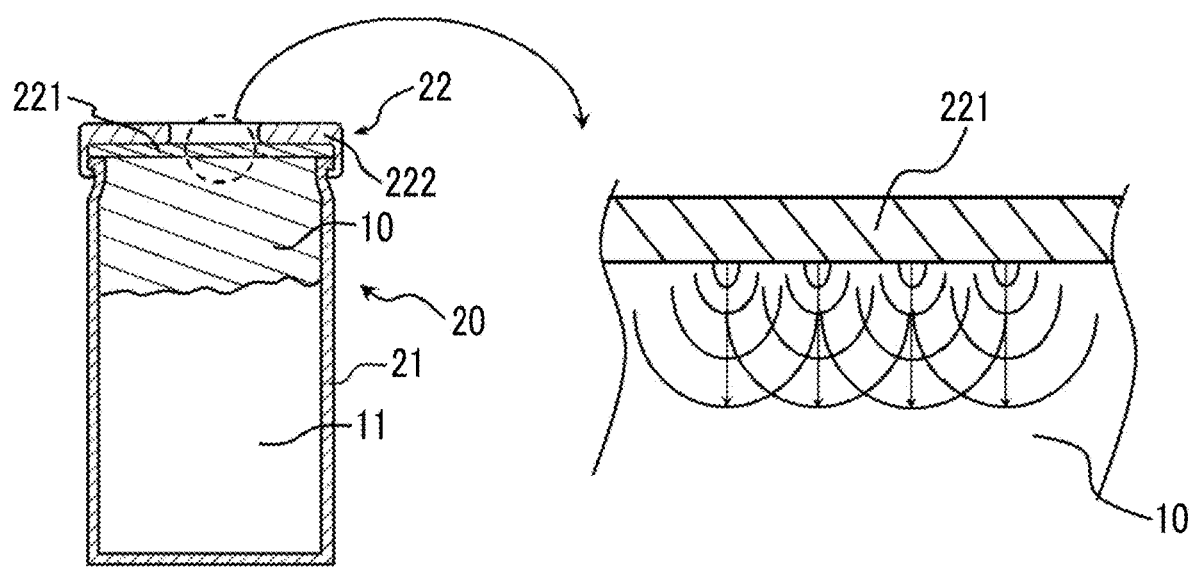
FIG. 5 is a partially enlarged view for illustrating a state where an aqueous liquid violently collides with an inner surface (top surface) of a container in a step of vibrating a container shown in FIG. 4(c).

Then, by using perfluorobutane, purging was performed in the void in the vial into which the aqueous liquid was injected, and then a lid having the same shape as that of the lid 22 shown in FIG. 4 was inserted into the mouth of the vial. Thereafter, a syringe filled with perfluorobutane was prepared. An injection needle of the syringe was pierced into the rubber stopper of the lid, and 2 ml of perfluorobutane was further added into the vial from the syringe. In this way, a sealed vial having an internal pressure of 2 atm was obtained.

[Step of Vibrating Container]

Then, two sealed vials obtained as above were prepared. By using Precellys (high-speed cell disruption system) manufactured by bertin Technologies, one of the sealed vials was vibrated for 30 seconds at the number of revolution of 5,000 rpm, and the other vial was vibrated for 30 seconds at the number of revolution of 6,500 rpm. At this time, the sealed vials were caused to reciprocate in a vertical direction, and it was confirmed that the aqueous liquid repeatedly collided with the top and bottom surfaces of the vial. When the sealed vials were vibrated, a vibration width of the sealed vials was 40 mm in the longitudinal direction (vertical direction) and 20 mm in the transverse direction (horizontal direction). The conditions were set as described above such that an instantaneous relative speed between each vial and the aqueous liquid became equal to or higher than 40 km/h in any of the vials.

[Step of Allowing Container to Stand]

After being vibrated, the sealed vials were allowed to stand, thereby obtaining bubble-containing containers.

(Measurement of Bubble Diameter Distribution)

From each of the bubble-containing containers obtained as above, the aqueous liquid containing bubbles (bubble-containing liquid) was taken using a syringe. Then, by using a bubble measurement device (nanoparticle analysis system nanosight), a bubble diameter distribution of the bubbles contained in the aqueous liquid was measured. The results are shown in FIG. 20.

Figure 20:
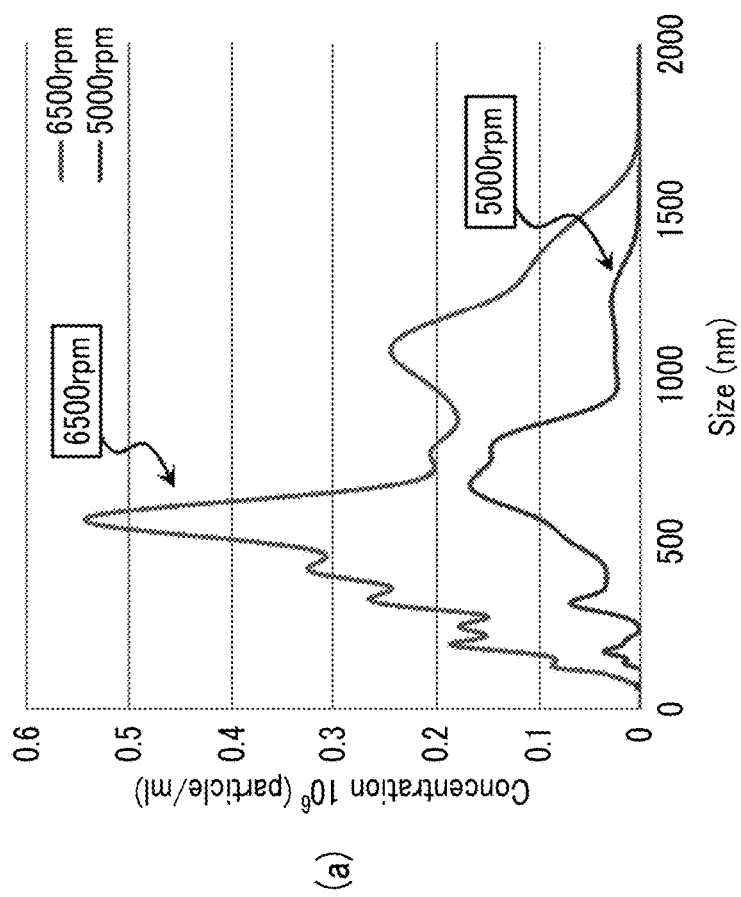
FIG. 20(a) is a graph showing a bubble diameter distribution of bubbles obtained when the bubbles are manufactured at the number of revolution of each of 5,000 rpm and 6,500 rpm.
FIG. 20(b) is a partially enlarged view obtained by setting the range of the abscissa axis in the graph shown in FIG. 20(a) to be 0 to 700 nm.

FIG. 20($a$) is a graph showing a bubble diameter distribution of bubbles manufactured at the number of revolution of each of 5,000 rpm and 6,500 rpm. FIG. 20($b$) is a partially enlarged view obtained by setting the range of the abscissa axis in the graph shown in FIG. 20($a$) to be 0 to 700 nm.

As shown in FIG. 20($a$), in a case where the sealed vial was vibrated at 6,500 rpm, the content of the bubbles in the aqueous liquid can be further increased greatly than in a case where the sealed vial was vibrated at 5,000 rpm. Particularly, the content of bubbles having a smaller diameter than about 600 nm was greater in a case where the sealed vial was vibrated at 6,500 rpm than in a case where the sealed vial was vibrated at 5,000 rpm, in more than 3 to 5 times.

In a case where the number of revolution of the sealed vial was 5,000 rpm, by lengthening the vibration time, the content of the bubbles in the aqueous liquid can be increased to some extent. However, the content of the bubbles obtained in this aqueous liquid was smaller than the content of the bubbles obtained in a case where the number of revolution was 6,500 rpm.

As shown in FIG. 20($b$), in a case where the sealed vial was vibrated at 6,500 rpm, a large amount of extremely small bubbles having a diameter of about 100 to 150 nm could be generated.

The above results are considered to be yielded by the following operations and effects. That is, according to the number of revolution of the sealed vial, the magnitude of the pressure of the shock waves that occur when the aqueous liquid collides with the vial changes. The magnitude of the pressure of the shock waves is an important factor that determines the diameter and the content of the bubbles generated in the aqueous liquid. In a case where the vial is stirred using a general stirrer or vibrated at the number of revolution lower than 5,000 rpm, such shock waves do not occur, or even though the shock waves occur, the amount of the occurring shock waves is small. Therefore, unlike in the invention of the present application, the bubbles having a sufficiently small diameter cannot be generated in the aqueous liquid at a high content.

Figure 21:
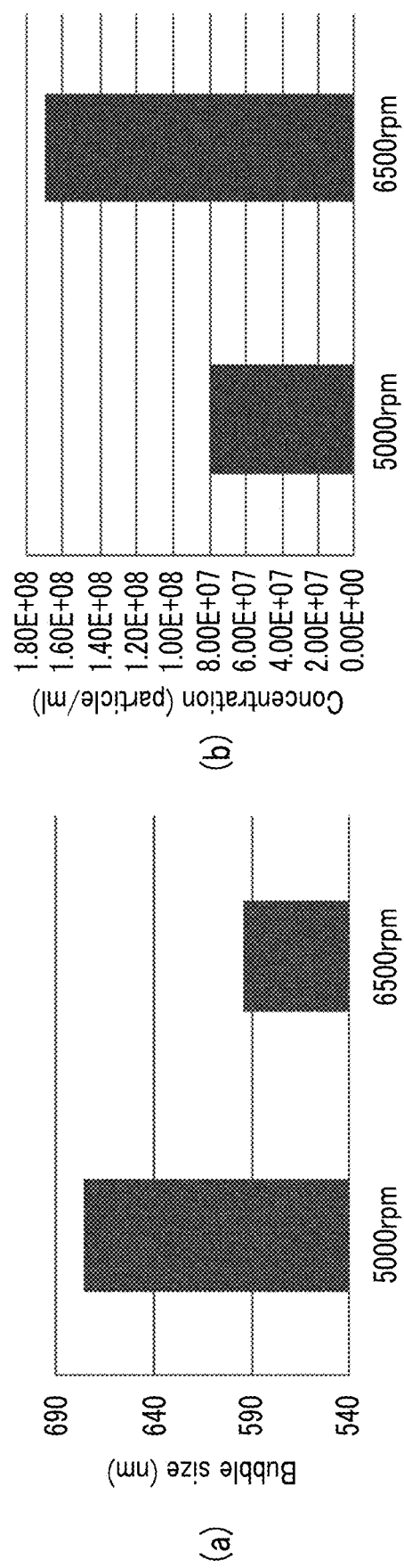
FIG. 21(a) is a graph showing a relationship between the number of revolution of a sealed vial and an average bubble diameter.
FIG. 21(b) is a graph showing the relationship between the number of revolution of a sealed vial and a content of bubbles.

FIG. 21 shows results obtained by analyzing a graph of a bubble diameter distribution shown in FIG. 20($a$). FIG. 21($a$) is a graph showing a relationship between the number of revolution of a sealed vial and an average bubble diameter. FIG. 21($b$) is a graph showing the relationship between the number of revolution of a sealed vial and a content of bubbles.

As shown in FIG. 21($a$), in a case where the sealed vial was vibrated at 6,500 rpm, an average diameter of the generated bubbles was smaller than in a case where the sealed vial was vibrated at 5,000 rpm, by about 80 nm. Furthermore, as shown in FIG. 21($b$), in a case where the sealed vial was vibrated at 6,500 rpm, a content of the generated bubbles was smaller than in a case where the sealed vial was vibrated at 5,000 rpm, by about $9 \times 10^7$ (particle)/ml. From these results, it was also understood that in a case where the sealed vial is vibrated at 6,500 rpm, more bubbles having a small diameter could be generated as compared with a case where the sealed vial is vibrated at 5,000 rpm.

Example 2

Then, relationships between the volume of the gas 3 sealed in the manufacturing container 20 and the diameter and content of the bubbles 1 generated in the aqueous liquid 10 were investigated.

(Method for Manufacturing Bubbles)

A bubble-containing container was obtained in the same manner as in Example 1, except that in Step of sealing container in Example 1, four sealed vials were prepared, which were obtained by changing the volume of perfluorobutane sealed in the vial into 0.5 ml, 1 ml, 1.5 ml, and 2 ml, respectively.

Regarding each of the sealed vials, the following Table 1 shows the volume (ml) of the gas (perfluorobutane) sealed therein, the internal pressure (atm) of the sealed vial, and the number of revolution (rpm) of the sealed vial in Step of vibrating container.

TABLE 1

| Volume of gas to be sealed (ml) | Internal pressure of sealed vial (atm) | Number of revolution (rpm) |
| --- | --- | --- |
| 0.5 | 1.2 | 6,500 |
| 1 | 1.3 | 6,500 |
| 1.5 | 1.5 | 6,500 |
| 2 | 2 | 6,500 |

(Measurement of Bubble Diameter Distribution)

Figure 22:
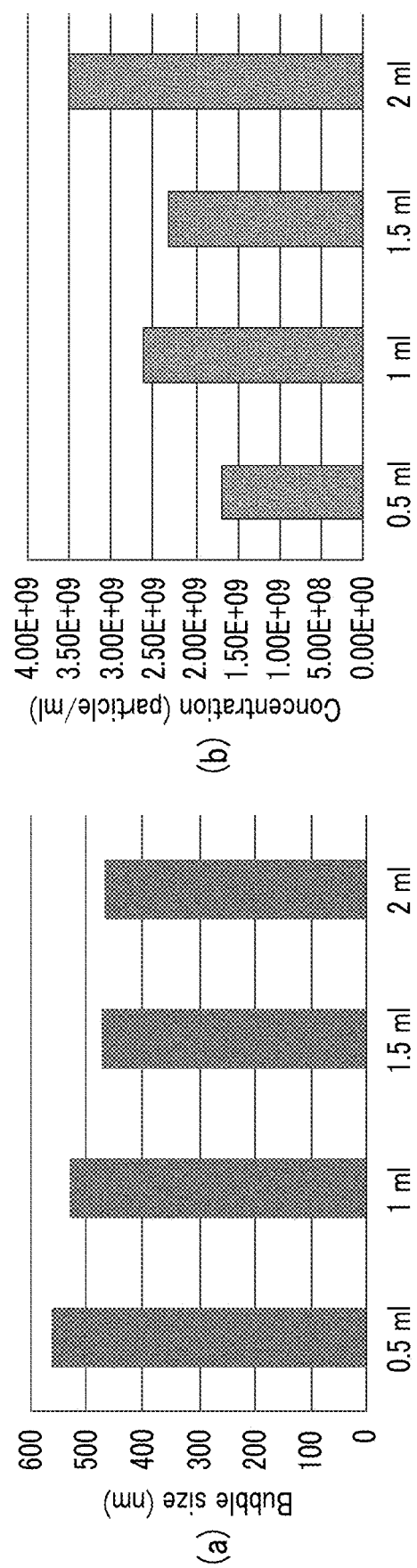
FIG. 22(a) is a graph showing a relationship between a volume of a gas sealed in a sealed vial and an average bubble diameter.
FIG. 22(b) is a graph showing a relationship between a volume of a gas sealed in a sealed vial and a content of bubbles.

In the same manner as in Example 1, a bubble diameter distribution of the bubble-containing liquid in each of the obtained bubble-containing containers was measured. FIG. 22 shows results obtained by analyzing a graph of the obtained bubble diameter distribution.

FIG. 22($a$) is a graph showing a relationship between a volume of a gas sealed in a sealed vial and an average diameter of bubbles.

FIG. 22($b$) is a graph showing a relationship between a volume of a gas sealed in a sealed vial and a content of bubbles.

As shown in FIG. 22($a$), even though the number of revolution at which each of the sealed vials was vibrated was the same, by increasing the internal pressure of the sealed vial, the average diameter of the generated bubbles was reduced. Specifically, in a case where the internal pressure of a sealed vial was 2 atm, the average diameter of the generated bubbles was smaller than in a case where the internal pressure of the sealed vial was 1.2 atm, by about 100 nm.

As shown in FIG. 22($b$), by increasing the internal pressure of the sealed vial, the content of the bubbles increased. Particularly, in a case where the internal pressure of a sealed vial was 2 atm, the content of the bubbles was greater than in a case where the internal pressure of the sealed vial was 1.2 atm, in equal to or more than 2.

It is considered that in a case where the internal pressure of the sealed vial is increased, the pressure of the shock waves which occur when the aqueous liquid collides with the vial may exert a big influence on the diameter and content of the generated bubbles. Therefore, even though the number of revolution at which each of the sealed vials is vibrated is the same, according to the internal pressure of the sealed vial, the average diameter of the generated bubbles changes. Furthermore, in a case where the internal pressure of the sealed vial increases, a large amount of gas is incorporated into the aqueous liquid. Consequently, due to the influence of the shock waves described above, the content of the bubbles generated in the aqueous liquid could be increased.

Example 3

(Method for Manufacturing Nanobubbles Containing GFP Gene)

[Preparation Step]

First, in the same manner as in the first embodiment described above, 120 µl of an albumin solution (ALBU-MINAR 25% manufactured by CSL Behring) and 12 ml of 25% phosphate-buffered saline were prepared. Furthermore, 2 µg of GFP genes were prepared. In addition, a 15 ml vial (height X: 50 mm, outer diameter R: 25 mm) was prepared. The vial had the same shape as that of the manufacturing container 20 shown in FIG. 4.

[Step of Injecting Aqueous Liquid into Container]

The entireties of the albumin solution, the 25% phosphate-buffered saline, and the GFP genes were injected into the prepared vial. Here, a height Y of a surface of an aqueous liquid obtained by mixing together the albumin solution, the 25% phosphate-buffered saline, and the GFP genes was 25 mm.

[Step of Sealing Container]

Then, by using perfluorobutane, purging was performed in a void in the vial into which the aqueous liquid was injected, and then a lid having the same shape as that of the lid 22 shown in FIG. 4 was inserted into the mouth of the vial. Thereafter, a syringe filled with perfluorobutane was prepared. An injection needle of the syringe was pierced into the rubber stopper of the lid, and 2 ml of perfluorobutane was further added into the vial from the syringe. In this way, a sealed vial having an internal pressure of 2 atm was obtained.

[Step of Vibrating Container]

Then, by using Precellys manufactured by bertin Technologies, the sealed vial was vibrated for 30 seconds at the number of revolution of 7,000 rpm. At this time, the sealed vial was caused to reciprocate in a vertical direction, and it was confirmed that the aqueous liquid repeatedly collided with the top and bottom surfaces of the vial. When the sealed vial was vibrated, a vibration width of the sealed vial was 40 mm in the longitudinal direction (vertical direction) and 20 mm in the transverse direction (horizontal direction). The conditions were set as described above such that an instantaneous relative speed between the vial and the aqueous liquid became equal to or higher than 40 km/h.

[Step of Allowing Container to Stand]

After being vibrated, the sealed vial was allowed to stand, thereby obtaining a bubble-containing container. The aqueous liquid (bubble-containing liquid) containing bubbles was taken out using a syringe, and by using a bubble measurement device (nanoparticle analysis system nanosight), the sizes of the bubbles were confirmed. As a result, an average diameter of the bubbles was 600 nm.

<Evaluation of Introduction of Fluorescent Protein Expression Gene into Cell>

0.2 µg of the aqueous liquid obtained in Example 3 was added to a petri dish in which cerebrovascular pericytes (manufactured by TAKARA BIO INC, product code: C-12980) were cultured, thereby obtaining a culture medium of the cerebrovascular pericytes. Pericytes are known as cells into which a gene is hardly introduced.

Four samples of the culture medium of the cerebrovascular pericytes were prepared. These samples were irradiated with ultrasonic waves having a frequency of 1.0 MHz (sine waves, pulse repetition frequency (PRF): 100 Hz, duty cycle (DC): 10%) for 60 seconds at the following power of irradiation.

[Power of Irradiation]

0.6 W/cm$^2$, 0.8 W/cm$^2$, 0.9 W/cm$^2$, 1.0 W/cm$^2$

Thereafter, the culture mediums of the cerebrovascular pericytes were cultured for 48 hours at 37° C., and then each of the samples obtained in this way was observed with a fluorescence microscope.

FIG. 23 shows fluorescent micrographs of a culture medium of cerebrovascular pericytes cultured for 48 hours at 37° C. FIG. 23($a$) is an image of a sample irradiated with ultrasonic waves at an irradiance of 0.6 W/cm$^2$, and FIG. 23($b$) is an image of a sample irradiated with ultrasonic waves at an irradiance of 0.8 W/cm$^2$. Furthermore, FIG. 24 shows fluorescent micrographs of a culture medium of cerebrovascular pericytes cultured for 48 hours at 37° C. FIG. 24($a$) is an image of a sample irradiated with ultrasonic waves at an irradiance of 0.9 W/cm$^2$, and FIG. 24($b$) is an image of a sample irradiated with ultrasonic waves at an irradiance of 1.0 W/cm$^2$.

As shown in FIGS. 23($a$) and 23($b$) and FIGS. 24($a$) and 24($b$), in any of the samples irradiated with ultrasonic waves at any power of irradiation, a region developing green was confirmed. This shows that a green fluorescent protein (GFP) is expressed in the cerebrovascular pericytes in each sample. Accordingly, it was understood that in any of the sample, the bubbles burst due to the irradiation of the ultrasonic waves, and hence the GFP genes contained in the bubbles were incorporated into the cerebrovascular pericytes.

Then, relationships between the type of the aqueous liquid 10 and the diameter and content of the bubbles 1 generated in the aqueous liquid 10 were investigated.

Example 4

(Method for Manufacturing Bubbles)

[Preparation Step]

First, as an aqueous liquid, 12 ml of distilled water was prepared. Furthermore, a 15 ml vial (height X: 50 mm, outer diameter R: 25 mm) was prepared. The vial has the same shape as that of the manufacturing container 20 shown in FIG. 4.

[Step of Injecting Aqueous Liquid into Container]

The distilled water (aqueous liquid) was injected into the prepared vial. A height Y of a surface of the aqueous liquid was 25 mm.

Then, by using perfluoropropane as a gas to be filled into the vial, [Step of sealing container] was performed. Thereafter, in the same manner as in the first embodiment, [Step of vibrating container] and [Step of allowing container to stand] were performed, thereby obtaining a bubble-containing container.

Example 5

A bubble-containing container was obtained in the same manner as in Example 4, except that the distilled water was changed to a 1 w/v % aqueous dextran solution.

Example 6

A bubble-containing container was obtained in the same manner as in Example 4, except that the distilled water was changed to 100% phosphate-buffered saline (PBS).

Example 7

A bubble-containing container was obtained in the same manner as in Example 4, except that the distilled water was changed to SOLDEM 3A infusion solution (manufactured by Terumo Corporation).

Example 8

A bubble-containing container was obtained in the same manner as in Example 4, except that the distilled water was changed to SOLDEM 1 infusion solution (manufactured by Terumo Corporation).

Example 9

A bubble-containing container was obtained in the same manner as in Example 4, except that the distilled water was changed to physiological saline (0.9 w/v % aqueous NaCl solution).

Example 10

A bubble-containing container was obtained in the same manner as in Example 4, except that the distilled water was changed to a 0.25 w/v % aqueous albumin solution.

Example 11

A bubble-containing container was obtained in the same manner as in Example 4, except that the distilled water was changed to a 20 w/v % aqueous glucose solution.

(Measurement of Bubble Diameter Distribution)

Figure 25:
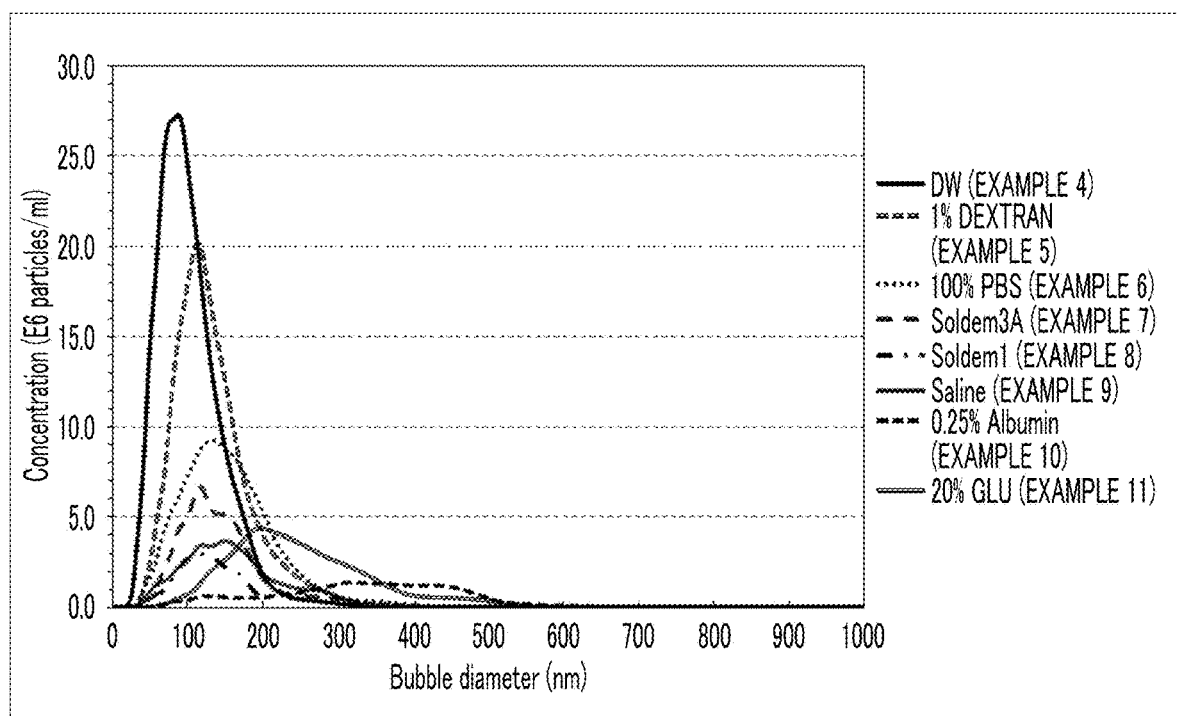
FIG. 25 is a graph showing bubble diameter distributions of bubbles obtained in Examples 4 to 11.

For each of the bubble-containing liquids of Examples 4 to 11 obtained as above, the bubble diameter distribution was measured in the same manner as in Example 1. FIG. 25 shows the results.

FIG. 25 is a graph showing bubble diameter distributions of the bubbles obtained in Examples 4 to 11.

As shown in FIG. 25, it was understood that the higher the concentration of water in the aqueous liquid is, the smaller the diameter of the generated bubbles 1 tends to be, and the larger the amount of the bubbles generated tends to be. Particularly, in Example 4 in which distilled water was used as the aqueous liquid, the average diameter of the bubbles was about 100 nm, and the content of the bubbles generated in the bubble-containing liquid was about $27 \times 10^6$ particles/ml. More specifically, in Example 4, the bubbles having a bubble diameter of about 100 nm were generated the most.

Furthermore, in Example 4, as a peak of the diameter of 100 nm, the bubbles having the bubble diameter of about 0 to 200 nm were generated.

In Example 7 in which the SOLDEM 3A infusion solution was used as the aqueous liquid and in Example 8 in which the SOLDEM 1 infusion solution was used as the aqueous liquid, the number of generated bubbles was smaller than in Example 4. However, in each of Examples 7 and 8, the bubble diameter distribution having a shape similar to that of Example 4 was obtained.

In Example 11 in which the 20 w/v % aqueous glucose solution was used as the aqueous liquid, the bubbles having the bubble diameter of about 200 nm were generated the most. The bubbles obtained in Example 11 had a broad bubble diameter distribution and the bubble diameter of about 100 to 400 nm. In Example 10 in which the 0.25% albumin was used as the aqueous liquid, the bubbles having the bubble diameter of about 100 to 500 nm were evenly generated.

In all of the bubble-containing liquids of Examples 4 to 11, bubbles having a size of equal to or larger than 500 nm substantially did not exist. Therefore, by using such bubble-containing liquids as an ultrasound contrast agent, a high-definition image with high resolution can be obtained.

Then, relationships between the type of the gas 3 and the diameter and content of the bubbles 1 generated in the aqueous liquid 10 were investigated.

Example 12

In Example 4, by changing the distilled water to physiological saline (0.9 w/v % aqueous NaCl solution), [Preparation step] and [Step of injecting aqueous liquid into container] were performed. Then, by using air as a gas to be filled into the vial, [Step of sealing container] was performed. Thereafter, in the same manner as in the first embodiment, [Step of vibrating container] and [Step of allowing container to stand] were performed, thereby obtaining a bubble-containing container.

Example 13

A bubble-containing container was obtained in the same manner as in Example 12, except that the air was changed to ethylene ($C_2H_4$).

Example 14

A bubble-containing container was obtained in the same manner as in Example 13, except that hydrogen was changed to ethylene ($C_2H_4$).

Example 15

A bubble-containing container was obtained in the same manner as in Example 13, except that hydrogen was changed to ethane ($C_2H_6$).

Example 16

A bubble-containing container was obtained in the same manner as in Example 13, except that hydrogen was changed to methane ($CH_4$).

Example 17

A bubble-containing container was obtained in the same manner as in Example 13, except that hydrogen was changed to nitrous oxide ($N_2O$).

(Measurement of Bubble Diameter Distribution)

Figure 26:
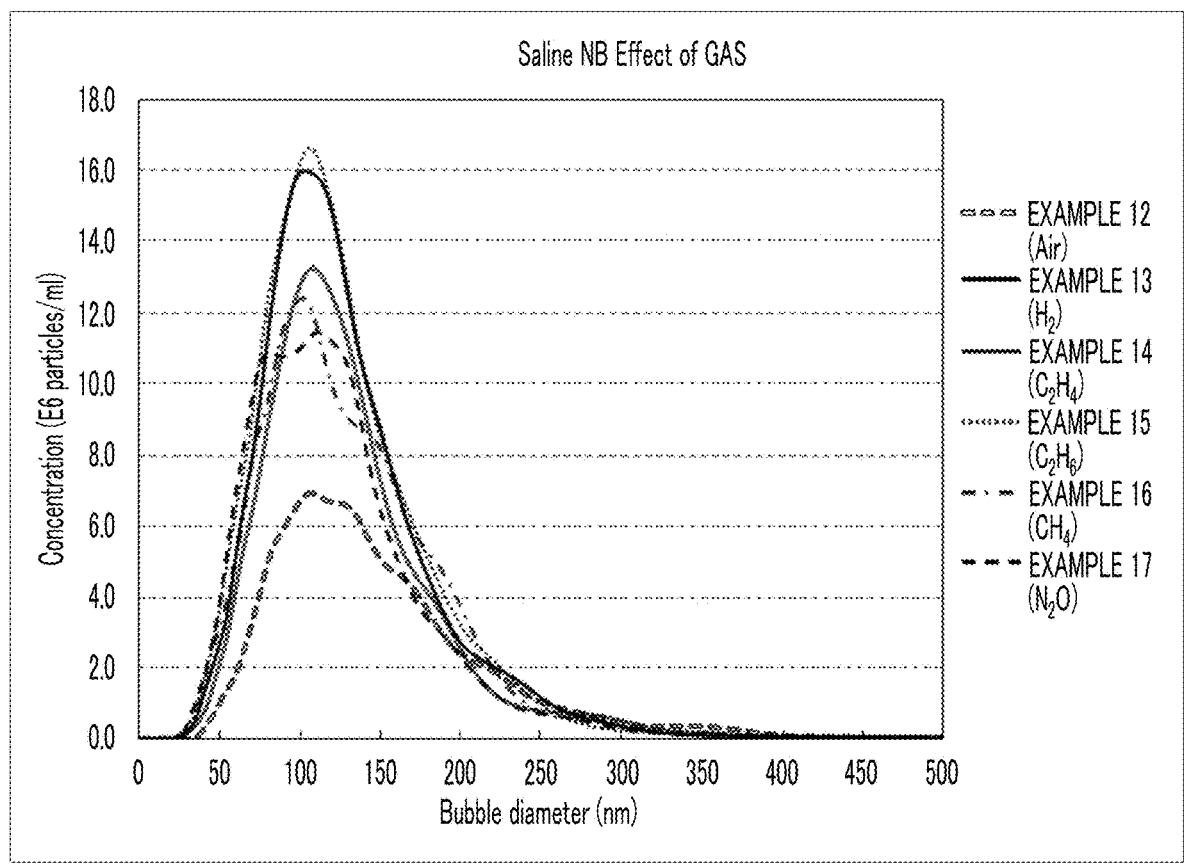
FIG. 26 is a graph showing bubble diameter distributions of bubbles obtained in Examples 12 to 17.

For each of the bubble-containing liquids of Examples 12 to 17 obtained as above, a bubble diameter distribution was measured in the same manner as in Example 1. FIG. 26 shows the results.

FIG. 26 is a graph showing bubble diameter distributions of bubbles obtained in Examples 12 to 17.

As shown in FIG. 26, by changing the type of the gas sealed in the vial, the amount of bubbles generated changed. In a case (Example 12) where the gas sealed in the vial was ethylene, the amount of bubbles generated was larger than in a case (Example 14) where the air was used as the gas sealed in the vial, by about 2 times. Particularly, it was understood that in Examples 13 and 15 in which hydrogen and ethane were used as the gas, respectively, the amount of generated bubbles increased.

Then, the diameter and content of the bubbles 1 generated using the manufacturing container 20 shown in FIG. 17 were investigated.

Example 18

(Method for Manufacturing Bubbles)

[Preparation Step]

First, in the same manner as in the first embodiment described above, 120 µl of an albumin solution (ALBUMINAR 25% manufactured by CSL Behring) and 12 ml of 25% phosphate-buffered saline were prepared. Furthermore, the manufacturing container 20 (length of top body portion: 23.82 mm, inner diameter of top body portion: 10.26 mm, length of bottom body portion: 20 mm, inner diameter of bottom body portion: 5.9 mm) shown in FIG. 17 was prepared.

[Step of Injecting Aqueous Liquid into Container]

The entireties of the albumin solution and the 25% phosphate-buffered saline were injected into the prepared manufacturing container. A height of a surface of an aqueous liquid obtained by mixing the albumin solution with the 25% phosphate-buffered saline was 25 mm from the bottom surface of the manufacturing container 20.

[Step of Sealing Container]

Then, a lid having the same shape as that of the lid 22 shown in FIG. 17 was inserted into the vial mouth (opening portion) of the manufacturing container 20 into which the aqueous liquid was injected. In this way, a sealed container (manufacturing container 20 sealed) having an internal pressure of 1 atm was obtained.

[Step of Vibrating Container]

Thereafter, two sealed containers described above were prepared. The weight portion 5 weighing 13.5 g was mounted on only one of the sealed containers (manufacturing containers 20). By using Precellys manufactured by bertin Technologies, these two manufacturing containers were vibrated for 30 seconds at the number of revolution of 6,500 rpm. At this time, the sealed containers were caused to reciprocate in a vertical direction, and it was confirmed that the aqueous liquid repeatedly collides with the top and bottom surfaces of the sealed containers. When the sealed containers were vibrated, a vibration width of the sealed containers was 40 mm in the longitudinal direction (vertical direction) and 20 mm in the transverse direction (horizontal direction). The conditions were set as described above such that an instantaneous relative speed between manufacturing container 20 and the aqueous liquid became equal to or higher than 40 km/h.

[Step of Allowing Container to Stand]

After being vibrated, the sealed containers were allowed to stand, thereby obtaining bubble-containing containers.

Example 19

In the same manner as in Example 18, an aqueous liquid formed of an albumin solution and 25% phosphate-buffered saline was injected into the manufacturing container 20 shown in FIG. 17.

Then, by filling the manufacturing container 20 with air in the same manner as in Example 12, [Step of sealing container] was performed. Thereafter, in the same manner as in Example 18, [Step of vibrating container] and [Step of allowing container to stand] were performed, thereby obtaining a bubble-containing container.

Example 20

A bubble-containing container was obtained in the same manner as in Example 19, except that the air was changed to perfluoropropane.

(Measurement of Bubble Diameter Distribution)

For each of the bubble-containing liquids of Examples 18 to 20 obtained as above, a bubble diameter distribution was measured in the same manner as in the first embodiment. Furthermore, a few drops of each of the bubble-containing liquids obtained in Examples 18 to 20 were added to a prepared slide by using a syringe, and it was observed with an optical microscope. FIGS. 27 and 28 show the results.

FIG. 27(*a*-1) shows a micrograph of the bubbles obtained using a container without the weight in Example 18 and a graph showing the bubble diameter distribution. FIG. 27(*a*-2) shows a micrograph of the bubbles obtained using the container with the weight in Example 18 and a graph showing the bubble diameter distribution. FIG. 27(*b*-1) shows a micrograph of the bubbles obtained using a container without the weight in Example 19 and a graph of the bubble diameter distribution. FIG. 27(*b*-2) shows a micrograph of the bubbles obtained using the container with the weight in Example 19 and a graph of the bubble diameter distribution.

FIG. 28(*a*-1) shows a micrograph of the bubbles obtained using a container without the weight in Example 20 and a graph of the bubble diameter distribution. FIG. 28(*a*-2) shows a micrograph of the bubbles obtained using the container with the weight in Example 20 and a graph of the bubble diameter distribution.

In the graphs of the bubble diameter distributions shown in each of FIGS. 27 and 28, the abscissa axis shows the measured bubble diameter. The diameter increases toward the right side from the left side on the abscissa axis. In the graph, the leftmost bar on the abscissa axis shows the amount of bubbles having an average diameter of equal to or less than 1 µm.

As shown in FIGS. 27 and 28, in all of Examples 18 to 20, in a case where the container with the weight was used, the amount of generated bubbles increased. Particularly, it was understood that bubbles having a small diameter (diameter: equal to or less than 1 µm) were generated in a markedly large amount. Furthermore, from the comparison between FIG. 27(*b*-2) and FIG. 28(*c*-2), it was understood that in the case where perfluoropropane was used as the gas sealed in the container, the bubbles having a smaller diameter were generated more than in a case where air was used as a gas. Accordingly, it was understood that by using the manufacturing container with the weight mounted on a portion thereof as shown in FIG. 17, the bubbles having the small diameter (bubbles having a diameter of equal to or less than 1 μm) could be efficiently manufactured.

INDUSTRIAL APPLICABILITY

According to the present invention, simply by vibrating a container at a predetermined number of revolution, a large amount of bubbles having a uniform size can be stably generated in an aqueous liquid. The bubble obtained in this way can be used in various fields such as medical care, food, seafood farming, and waste water treatment. Accordingly, the method for manufacturing bubbles of the present invention is industrially applicable.

What is claimed is:

1. A method for manufacturing bubbles, comprising:
   injecting an aqueous liquid into a container having a long shape to a predetermined height; and
   vibrating the container at a number of revolutions equal to or higher than 5,000 rpm such that the aqueous liquid repeatedly collides with an inner surface of the container,
   wherein the vibrating the container is performed by vibrating the container such that the container reciprocates in a longitudinal direction of the container, and
   provided that a height of the container is X (mm), a vibration width of the container in the longitudinal direction is in the range of 0.7X to 1.5X (mm).

2. The method for manufacturing bubbles according to claim 1,
   wherein the vibrating the container is performed in a state where an internal pressure of the container is higher than 1.0 atm.

3. The method for manufacturing bubbles according to claim 1,
   wherein the container has a long shape, and
   the vibrating the container is performed by vibrating the container such that the container reciprocates in a transverse direction of the container or rotates mainly in the transverse direction.

4. The method for manufacturing bubbles according to claim 3,
   wherein a vibration width of the container in a horizontal direction is in the range of 0.3X to 0.8X (mm).

5. The method for manufacturing bubbles according to claim 1 further comprising:
   injecting a predetermined gas into the container in a state where the container is sealed.

6. The method for manufacturing bubbles according to claim 1,
   wherein in a state where the container containing the aqueous liquid is allowed to stand horizontally, provided that a height of the container is X (mm) and a height of a surface of the aqueous liquid in the container is Y (mm), a relationship of 0.2≤Y/X≤0.7 is satisfied.

7. The method for manufacturing bubbles according to claim 1,
   wherein the container has a volume of 15 to 20 ml, and
   wherein when the aqueous liquid collides with the inner surface of the container, an instantaneous relative speed between the container and the aqueous liquid in the container becomes equal to or higher than 40 km/h.

8. The method for manufacturing bubbles, comprising:
   injecting an aqueous liquid into a container having a long shape to a predetermined height;
   vibrating the container at a number of revolutions equal to or higher than 5,000 rpm such that the aqueous liquid repeatedly collides with an inner surface of the container; and
   vibrating again the container at the number of revolutions equal to or higher than 5,000 rpm after an internal pressure of the container is changed, after the vibrating the container.

9. The method for manufacturing bubbles according to claim 8,
   wherein the vibrating again the container is performed such that the internal pressure is 1 to 10 atm higher than the internal pressure in the vibrating the container.

10. The method for manufacturing bubbles according to claim 8,
    wherein the vibrating again the container is performed at a number of revolutions different from the number of revolutions in the vibrating the container.

* * * * *